(12) United States Patent
Bradbury et al.

(10) Patent No.: US 10,130,617 B2
(45) Date of Patent: *Nov. 20, 2018

(54) CHEMICAL COMPOUNDS

(71) Applicant: AstraZeneca AB, Sodertalje (SE)

(72) Inventors: Robert Hugh Bradbury, Macclesfield (GB); David Buttar, Macclesfield (GB); Christopher De Savi, Waltham, MA (US); Craig Samuel Donald, Macclesfield (GB); Richard Albert Norman, Macclesfield (GB); Alfred Arthur Rabow, Macclesfield (GB); Gordon Stuart Currie, Macclesfield (GB); Heather Redfearn, Macclesfield (GB); Nadim Akhtar, Macclesfield (GB); Helen Elizabeth Williams, Macclesfield (GB); Matthew Osborne, Macclesfield (GB); Neda Yavari, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/445,000

(22) Filed: Feb. 28, 2017

(65) Prior Publication Data

US 2017/0326115 A1    Nov. 16, 2017

Related U.S. Application Data

(63) Continuation of application No. 14/840,342, filed on Aug. 31, 2015, now Pat. No. 9,616,050, which is a continuation of application No. 14/287,332, filed on May 27, 2014, now Pat. No. 9,155,727.

(60) Provisional application No. 61/915,685, filed on Dec. 13, 2013, provisional application No. 61/827,951, filed on May 28, 2013.

(51) Int. Cl.
| | | |
|---|---|---|
| *A61K 31/437* | (2006.01) | |
| *A61K 31/519* | (2006.01) | |
| *C07D 487/04* | (2006.01) | |
| *C07D 471/04* | (2006.01) | |
| *A61K 45/06* | (2006.01) | |
| *C07C 57/145* | (2006.01) | |

(52) U.S. Cl.
CPC .......... *A61K 31/437* (2013.01); *A61K 31/519* (2013.01); *A61K 45/06* (2013.01); *C07C 57/145* (2013.01); *C07D 471/04* (2013.01); *C07D 487/04* (2013.01); *C07B 2200/07* (2013.01); *C07B 2200/13* (2013.01)

(58) Field of Classification Search
CPC .. A61K 31/437; A61K 31/519; C07D 471/04; C07D 487/04
USPC ........................................... 514/292; 546/85
See application file for complete search history.

(56) References Cited

U.S. PATENT DOCUMENTS

| | | |
|---|---|---|
| 2003/0040527 A1 | 2/2003 | Yeh |
| 2007/0032385 A1 | 2/2007 | Dunetz |
| 2010/0003324 A1 | 1/2010 | Ellis |

FOREIGN PATENT DOCUMENTS

| | | |
|---|---|---|
| EP | 1637521 B1 | 6/2013 |
| WO | 1997/039748 A1 | 10/1997 |
| WO | 2000/001690 A1 | 1/2000 |
| WO | 2000/064888 A1 | 11/2000 |
| WO | 2003/059346 A1 | 7/2003 |
| WO | 2003/088970 A2 | 10/2003 |
| WO | 2003/099821 A1 | 12/2003 |
| WO | 2004/099150 A2 | 11/2004 |
| WO | 2005/016001 A1 | 2/2005 |
| WO | 2005/070930 A2 | 8/2005 |
| WO | 2006/037982 A2 | 5/2006 |
| WO | 2006/050212 A1 | 5/2006 |
| WO | 2006/055625 A2 | 5/2006 |
| WO | 2006/088949 A1 | 8/2006 |
| WO | 2007/133653 A2 | 11/2007 |
| WO | 2008/025965 A2 | 3/2008 |
| WO | 2008/124836 A2 | 10/2008 |
| WO | 2008/127714 A1 | 10/2008 |
| WO | 2008/127715 A1 | 10/2008 |

(Continued)

OTHER PUBLICATIONS

Cancer Genome Atlas Network 'Comprehensive Molecular Portraits of Human Breast Tumours', Nature (2012); vol. 490; 61-70.

(Continued)

*Primary Examiner* — Rita J Desai
(74) *Attorney, Agent, or Firm* — Meaghan L. Richmond

(57) ABSTRACT

The invention concerns compounds of Formula (I)

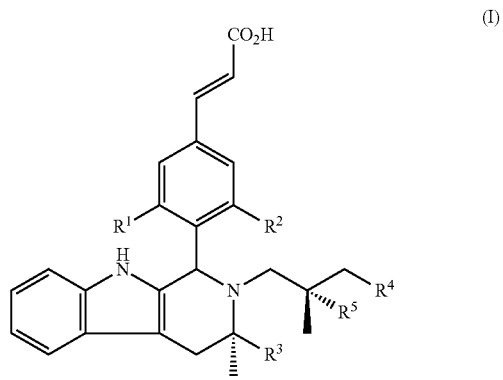

or pharmaceutically-acceptable salts thereof, wherein $R^1$ to $R^5$ have any of the meanings defined hereinbefore in the description; processes for their preparation, pharmaceutical compositions containing them and their use in the treatment of cell proliferative disorders.

13 Claims, 12 Drawing Sheets

(56) References Cited

FOREIGN PATENT DOCUMENTS

| WO | 2009/011836 A1 | 1/2009 |
|---|---|---|
| WO | 2010/083136 A1 | 7/2010 |
| WO | 2010/107485 A1 | 9/2010 |
| WO | 2010/138706 A1 | 12/2010 |
| WO | 2012/112961 A1 | 8/2012 |
| WO | 2012/112965 A1 | 8/2012 |
| WO | 2013/022740 A2 | 2/2013 |

OTHER PUBLICATIONS

Dahlman-Wright et al., 'International Union of Pharmacology. LXIV. Estrogen Receptors', Pharmacol. Rev. (2006); vol. 58; No. 4; 773-781.
Dondas et al., 'Solid phase sequential 1,3-dipolar cycloaddition—Pictet—Spengler reactions', Tetrahedron Letters (2000); vol. 41; 967-970.
Herlem et al., 'Oxydation Photochimique D'amines Tertiaires et C'alcaloides XI', Tetrahedron (1982); vol. 38; No. 2; 271-278 (English Language abstract included).
Kato et al., 'Activation of the Estrogen Receptor Through Phosphorylation by Mitogen-Activated Protein Kinase' Science (1995); vol. 270; 1491-1494.
Kumpaty et al., 'Study of the Cis to Trans Isomerization of 1-Phenyl-2,3-disubstituted Tetrahydro-β-carbolines at C(1). Evidence for the Carbocation-Mediated Mechanism' J. Org. Chem. (2009); vol. 74; 2771-2779.
Kushner et al., 'Estrogen receptor action through target genes with classical and alternative response elements', Pure Applied Chemistry (2003); vol. 75; No. 11-12; 1757-1769.
Li et al., 'Endocrine-Therapy-Resistant ESR1 Variants Revealed by Genomic Characterization of Breast-Cancer-Derived Xenografts', Cell Rep. (2013); vol. 4; 1116-1130.
Lonard et al., 'The 26S Proteasome is Required for Estrogen Receptor-α and Coactivator Turnover and for Efficient Estrogen Receptor-α Transactivation', Mol. Cell. (2000); vol. 5; 939-948.
Pike et al., 'Structural Insights into the Mode of Action of a Pure Antiestrogen', Structure (2001); vol. 9; 145-153.
Robinson et al., 'Activating ESR1 mutations in hormone-resistant metastatic breast cancer', Nature Genetics (2013); vol. 45; No. 12; 1446-1451.
Shen et al., 'The Preparation and Evaluation of 1-Substituted 1,2,3,4-Tetrahydro- and 3,4-Dihydro-β-carboline Derivatives as Potential Antitumor Agents', Chem & Pharm Bull (2005); vol. 53; No. 1; 32-36.
Stenoien et al., 'Ligand-Mediated Assembly and Real-Time Cellular Dynamics of Estrogen Receptor α-Coactivator Complexes in Living Cells', Mol. Cell Biol. (2001); vol. 21; No. 13; 4404-4412.
Toy et al., 'ESR1 Ligand-binding Domain Mutations in Hormone-Resistant Breast Cancer', Nat. Genetics (2013); vol. 45; No. 12; 1439-1445.
Tzukerman et al., 'Human Estrogen Receptor Transactivational Capacity is Determined by Both Cellular and Promoter Context and Mediated by Two Functionally Distinct Intramolecular Regions', Mol. Endocrinology (1994); vol. 8; 21-30.
Wakeling et al., 'A Potent Specific Pure Antiestrogen with Clinical Potential', Cancer Res. (1991); vol. 51; 3867-3873.
Wardell et al., 'The Turnover of Estrogen Receptor α by the Selective Estrogen Receptor Degrader (SERD) Fulvestrant is a Saturable Process that is not Required for Antagonist Efficacy', Biochem. Pharm. (2011); vol. 82; 122-130.
Warner et al., 'Nongenomic Effects of Estrogen: Why all the Uncertainty?', Steroids (2006); vol. 71; 91-95.
Weir et al., 'Development of a novel selective estrogen receptor degrader which shows efficacy in pre-clinical models of ndocrine resistance', SABCS conference (San Antonio Breast Cancer Symposium); Dec. 13, 2013; Poster.

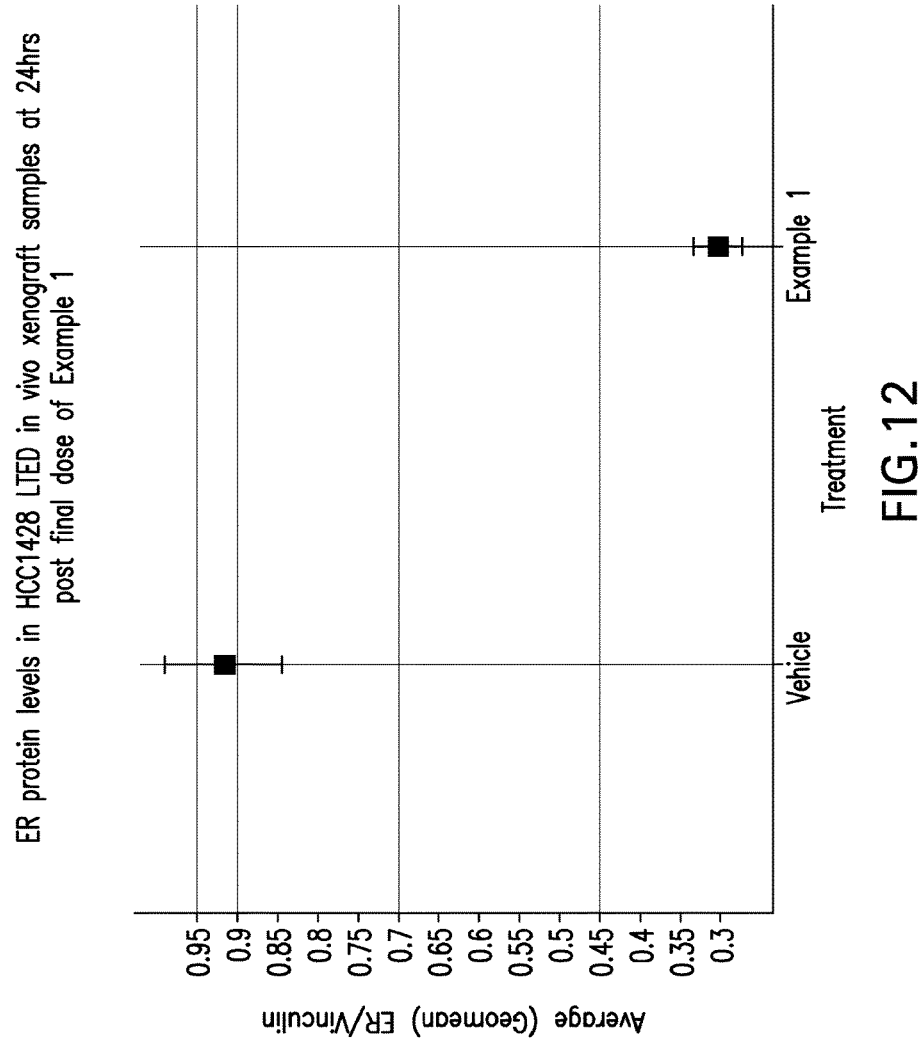

CHEMICAL COMPOUNDS

This application is a continuation of U.S. patent application Ser. No. 14/840,342, filed Aug. 31, 2015 which is a continuation of U.S. patent application Ser. No. 14/287,332, filed May 27, 2014, granted Oct. 13, 2015 as U.S. Pat. No. 9,155,727, which claims the benefit under 35 U.S.C. § 119(e) of Provisional Patent Application No. 61/827,951, filed on May 28, 2013, and Provisional Patent Application No. 61/915,685, filed on Dec. 13, 2013.

The invention concerns certain novel indole derivatives, or pharmaceutically-acceptable salts thereof, which possess anti-cancer activity and are accordingly potentially useful in methods of treatment of the human or animal body. The invention also concerns processes for the manufacture of said indole derivatives, pharmaceutical compositions containing them and their use in therapeutic methods, for example in the manufacture of medicaments for use in the prevention or treatment of cancers in a warm-blooded animal such as man, including use in the prevention or treatment of cancer.

The present invention also relates to indole derivatives that are selective down-regulators of the estrogen receptor.

Estrogen receptor alpha (ERα, ESR1, NR3A) and estrogen receptor beta (ERβ, ESR2, NR3b) are steroid hormone receptors which are members of large nuclear receptor family. Structured similarly to all nuclear receptors, ERa is composed of six functional domains (named A-F) (Dahlman-Wright, et al., *Pharmacol. Rev.,* 2006, 58:773-781) and is classified as a ligand-dependent transcription factor because after its association with the specific ligand, the female sex steroid hormone 17b estradiol (E2), the complex binds to genomic sequences, named Estrogen Receptor Elements (ERE) and interacts with co-regulators to modulate the transcription of target genes. The ERα gene is located on 6q25.1 and encodes a 595AA protein and multiple isoforms can be produced due to alternative splicing and translational start sites. In addition to the DNA binding domain (Domain C) and the ligand binding domain (Domain E) the receptor contains an N-terminal (A/B) domain, a hinge (D) domain that links the C and E domains and a C-terminal extension (F domain). While the C and E domains of ERa and ERb are quite conserved (96% and 55% amino acid identity respectively) conservation of the A/B, D and F domains is poor (below 30% amino acid identity). Both receptors are involved in the regulation and development of the female reproductive tract and in addition play roles in the central nervous system, cardiovascular system and in bone metabolism. The genomic action of ERs occurs in the nucleus of the cell when the receptor binds EREs directly (direct activation or classical pathway) or indirectly (indirect activation or non-classical pathway). In the absence of ligand, ERs are associated with heat shock proteins, Hsp90 and Hsp70, and the associated chaperone machinery stabilizes the ligand binding domain (LBD) making it accessible to ligand. Liganded ER dissociates from the heat shock proteins leading to a conformational change in the receptor that allows dimerisation, DNA binding, interaction with co-activators or co-repressors and modulation of target gene expression. In the non-classical pathway, AP-1 and Sp-1 are alternative regulatory DNA sequences used by both isoforms of the receptor to modulate gene expression. In this example, ER does not interact directly with DNA but through associations with other DNA bound transcription factors e.g. c-Jun or c-Fos (Kushner et al., Pure Applied Chemistry 2003, 75:1757-1769). The precise mechanism whereby ER affects gene transcription is poorly understood but appears to be mediated by numerous nuclear factors that are recruited by the DNA bound receptor. The recruitment of co-regulators is primarily mediated by two protein surfaces, AF2 and AF1 which are located in E-domain and the A/B domain respectively. AF1 is regulated by growth factors and its activity depends on the cellular and promoter environment whereas AF2 is entirely dependent on ligand binding for activity. Although the two domains can act independently, maximal ER transcriptional activity is achieved through synergistic interactions via the two domains (Tzukerman, et al., *Mol. Endocrinology,* 1994, 8:21-30). Although ERs are considered transcription factors they can also act through non-genomic mechanisms as evidenced by rapid ER effects in tissues following E2 administration in a timescale that is considered too fast for a genomic action. It is still unclear if receptors responsible for the rapid actions of estrogen are the same nuclear ERs or distinct G-protein coupled steroid receptors (Warner, et al., Steroids 2006 71:91-95) but an increasing number of E2 induced pathways have been identified e.g. MAPK/ERK pathway and activation of endothelial nitric oxide synthase and PI3K/Akt pathway. In addition to ligand dependent pathways, ERα has been shown to have ligand independent activity through AF-1 which has been associated with stimulation of MAPK through growth factor signalling e.g. insulin like growth factor 1 (IGF-1) and epidermal growth factor (EGF). Activity of AF-1 is dependent on phosphorylation of Ser118 and an example of cross-talk between ER and growth factor signalling is the phosphorylation of Ser 118 by MAPK in response to growth factors such as IGF-1 and EGF (Kato, et al., *Science,* 1995, 270:1491-1494).

A large number of structurally distinct compounds have been shown to bind to ER. Some compounds such as endogenous ligand E2, act as receptor agonists whereas others competitively inhibit E2 binding and act as receptor antagonists. These compounds can be divided into 2 classes depending on their functional effects. Selective estrogens receptor modulators (SERMs) such as tamoxifen have the ability to act as both receptor agonists and antagonists depending on the cellular and promoter context as well as the ER isoform targeted. For example tamoxifen acts as an antagonist in breast but acts as a partial agonist in bone, the cardiovascular system and uterus. All SERMs appear to act as AF2 antagonists and derive their partial agonist characteristics through AF1. A second group, fulvestrant being an example, are classified as full antagonists and are capable of blocking estrogen activity via the complete inhibition of AF1 and AF2 domains through induction of a unique conformation change in the ligand binding domain (LBD) on compound binding which results in complete abrogation of the interaction between helix 12 and the remainder of the LBD, blocking co-factor recruitment (Wakeling, et al., *Cancer Res.,* 1991, 51:3867-3873; Pike, et al., *Structure,* 2001, 9:145-153).

Intracellular levels of ERα are down-regulated in the presence of E2 through the ubiquitin/proteosome (Ub/26S) pathway. Polyubiquitinylation of liganded ERα is catalysed by at least three enzymes; the ubiquitin-activating enzyme E1 activated ubiquitin is conjugated by E2 with lysine residues through an isopeptide bond by E3 ubiquitin ligase and polyubiquitinated ERα is then directed to the proteosome for degradation. Although ER-dependent transcription regulation and proteosome-mediated degradation of ER are linked (Lonard, et al., *Mol. Cell,* 2000 5:939-948), transcription in itself is not required for ERα degradation and assembly of the transcription initiation complex is sufficient to target ERα for nuclear proteosomal degradation. This E2 induced degradation process is believed to necessary for its ability to rapidly activate transcription in response to requirements for cell proliferation, differentiation and metabolism (Stenoien, et al., *Mol. Cell Biol.,* 2001, 21:4404-4412). Fulvestrant is also classified as a selective estrogen receptor down-regulator (SERD), a subset of antagonists that can also induce rapid down-regulation of ERα via the 26S proteosomal pathway. In contrast a SERM such as tamoxifen can increase ERα levels although the effect on transcription is similar to that seen for a SERD.

Approximately 70% of breast cancers express ER and/or progesterone receptors implying the hormone dependence of these tumour cells for growth. Other cancers such as ovarian and endometrial are also thought to be dependent on ERα signalling for growth. Therapies for such patients can inhibit ER signalling either by antagonising ligand binding to ER e.g. tamoxifen which is used to treat early and advanced ER positive breast cancer in both pre and post menopausal setting; antagonising and down-regulating ERα e.g. fulvestrant which is used to treat breast cancer in women which have progressed despite therapy with tamoxifen or aromatase inhibitors; or blocking estrogen synthesis e.g. aromatase inhibitors which are used to treat early and advanced ER positive breast cancer. Although these therapies have had an enormously positive impact on breast cancer treatment, a considerable number of patients whose tumours express ER display de novo resistance to existing ER therapies or develop resistance to these therapies over time. Several distinct mechanism have been described to explain resistance to first-time tamoxifen therapy which mainly involve the switch from tamoxifen acting as an antagonist to an agonist, either through the lower affinity of certain co-factors binding to the tamoxifen-ERα complex being off-set by over-expression of these co-factors, or through the formation of secondary sites that facilitate the interaction of the tamoxifen-ERα complex with co-factors that normally do not bind to the complex. Resistance could therefore arise as a result of the outgrowth of cells expressing specific co-factors that drive the tamoxifen-ERα activity. There is also the possibility that other growth factor signalling pathways directly activate the ER receptor or co-activators to drive cell proliferation independently of ligand signalling.

More recently, mutations in ESR1 have been identified as a possible resistance mechanism in metastatic ER-positive patient derived tumour samples and patient-derived xenograft models (PDX) at frequencies varying from 17-25%. These mutations are predominantly, but not exclusively, in the ligand-binding domain leading to mutated functional proteins; examples of the amino acid changes include Ser463Pro, Val543Glu, Leu536Arg, Tyr537Ser, Tyr537Asn and Asp538Gly, with changes at amino acid 537 and 538 constituting the majority of the changes currently described. These mutations have been undetected previously in the genomes from primary breast samples characterised in the Cancer Genome Atlas database. Of 390 primary breast cancer samples positive for ER expression not a single mutation was detected in ESR1 (Cancer Genome Atlas Network, 2012 *Nature* 490: 61-70). The ligand binding domain mutations are thought to have developed as a resistance response to aromatase inhibitor endocrine therapies as these mutant receptors show basal transcriptional activity in the absence of estradiol. The crystal structure of ER, mutated at amino acids 537 and 538, showed that both mutants favoured the agonist conformation of ER by shifting the position of helix 12 to allow co-activator recruitment and thereby mimicking agonist activated wild type ER. Published data has shown that endocrine therapies such as Tamoxifen and Fulvestrant can still bind to ER mutant and inhibit transcriptional activation to some extent and that Fulvestrant is capable of degrading Try537Ser but that higher doses may be needed for full receptor inhibition (Toy et al., *Nat. Genetics* 2013, 45: 1439-1445; Robinson et al., *Nat. Genetics* 2013, 45: 144601451; Li, S. et al. *Cell Rep.* 4, 1116-1130 (2013). It is therefore feasible that certain compounds of the formula (I), or pharmaceutically-acceptable salts thereof will be capable of down-regulating and antagonising mutant ER although it is not known at this stage whether ESR1 mutations are associated with an altered clinical outcome.

Regardless of which resistance mechanism or combination of mechanisms takes place, many are still reliant on ER-dependent activities and that removal of the receptor through a SERD mechanism offers the best way of removing the ERα receptor from the cell. Fulvestrant is currently the only SERD approved for clinical use, yet despite its mechanistic properties, the pharmacological properties of the drug have limited its efficacy due to the current limitation of a 500 mg monthly dose which results in less than 50% turnover of the receptor in patient samples compared to the complete down-regulation of the receptor seen in in-vitro breast cell line experiments (Wardell, et al., Biochem. Pharm., 2011, 82:122-130). Hence there is a need for new ER targeting agents that have the required pharmaceutical properties and SERD mechanism to provide enhanced benefit in the early, metastatic and acquired resistance setting.

The compounds of the invention have been found to possess potent anti-tumour activity, being useful in inhibiting the uncontrolled cellular proliferation which arises from malignant disease. The compounds of the invention provide an anti-tumour effect by, as a minimum, acting as SERDs.

According to one aspect of the invention there is provided a compound of the Formula (I) or a pharmaceutically-acceptable salt thereof

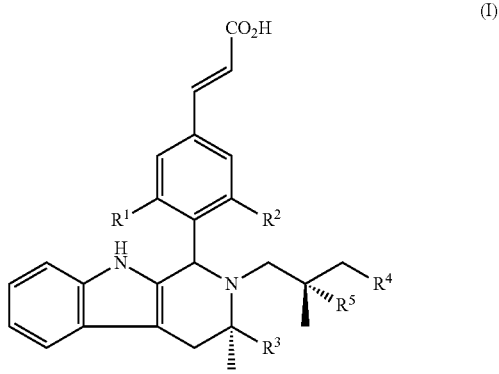

wherein:
R$^1$ and R$^2$ are each independently H or F;
R$^3$ is H or methyl; and
either:
a) R$^4$ is H and R$^5$ is F; or
b) R$^4$ is F and R$^5$ is H.

In another aspect of the invention, there is provided a compound of Formula (I) as defined above.

The compounds of formula (I) have one, two or three chiral centres and the invention encompasses pure chiral forms or mixtures thereof in any proportion. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques.

A particular enantiomer or diasteroeisomer of a compound described herein may be more active than other enantiomers or diastereoisomers of the same compound.

According to a further aspect of the invention there is provided a compound of the Formula (I), or a pharmaceutically-acceptable salt thereof, which is a single enantiomer being in an enantiomeric excess (% ee) of ≥95, ≥98% or ≥99%. Conveniently, the single enantiomer is present in an enantiomeric excess (% ee) of ≥99%.

According to a further aspect of the invention there is provided a pharmaceutical composition, which comprises a compound of the Formula (I), which is a single enantiomer being in an enantiomeric excess (% ee) of ≥95, ≥98% or ≥99% or a pharmaceutically-acceptable salt thereof, in association with a pharmaceutically-acceptable diluent or carrier. Conveniently, the single enantiomer is present in an enantiomeric excess (% ee) of ≥99%.

According to a further aspect of the invention there is provided a compound of the Formula (I), or a pharmaceutically-acceptable salt thereof, which is a single diastereoisomer being in an diastereomeric excess (% de) of ≥95, ≥98% or ≥99%. Conveniently, the single diastereoisomer is present in an diastereomeric excess (% de) of ≥99%.

According to a further aspect of the invention there is provided a pharmaceutical composition, which comprises a compound of the Formula (I), which is a single diastereoisomer being in an diastereomeric excess (% de) of ≥95, ≥98% or ≥99% or a pharmaceutically-acceptable salt thereof, in association with a pharmaceutically-acceptable diluent or carrier. Conveniently, the single diastereoisomer is present in an diastereomeric excess (% de) of ≥99%.

In one particular aspect, the compound of Formula (I) is a compound of Formula (IA):

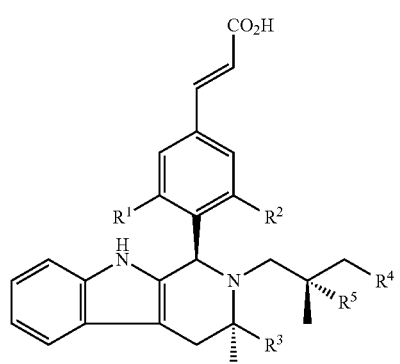

(IA)

In another aspect, the compound of Formula (I) is a compound of Formula (IB):

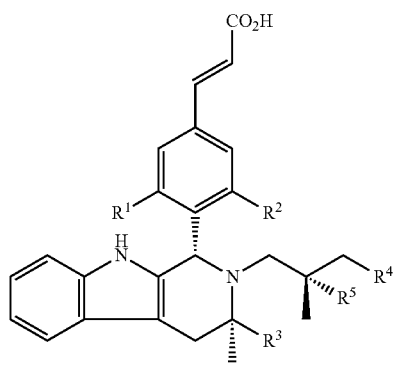

(IB)

Reference herein to compounds of Formula (I) is to be understood as referring to compounds of Formula (IA) and/or (IB) unless stated otherwise.

For Example, the compound of Example 1, (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid, is an example of a compound of Formula (IA).

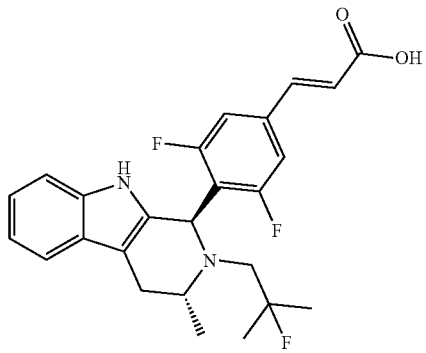 [SMILES: C[C@@H]1Cc2c([nH]c3ccccc23)[C@@H](c2c(F)cc(/C=C/C(=O)O)cc2F)N1CC(C)(C)F]

Its isomer, (E)-3-(3,5-difluoro-4-((1S,3R)-2-(2-fluoro-2-methylpropyl)-3-methyl-2,3,4,9-tetrahydro-1H-pyrido[3,4-b]indol-1-yl)phenyl)acrylic acid, is an example of a compound of Formula (IB).

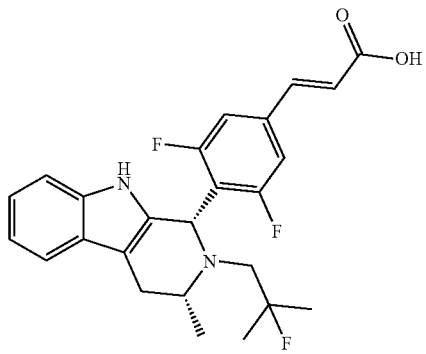 [SMILES: C[C@@H]1Cc2c([nH]c3ccccc23)[C@H](c2c(F)cc(/C=C/C(=O)O)cc2F)N1CC(C)(C)F]

Both of these two isomers are examples of (E)-3-(3,5-difluoro-4-((3R)-2-(2-fluoro-2-methylpropyl)-3-methyl-2,3,4,9-tetrahydro-1H-pyrido[3,4-b]indol-1-yl)phenyl)acrylic acid, which is an example of a compound of Formula (I).

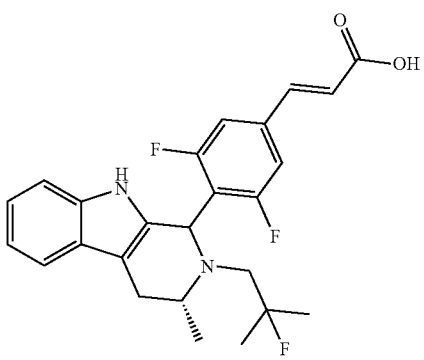 [SMILES: C[C@@H]1Cc2c([nH]c3ccccc23)C(c2c(F)cc(/C=C/C(=O)O)cc2F)N1CC(C)(C)F]

Some compounds of Formula (I) may be crystalline and may have more than one crystalline form. It is to be understood that the present invention encompasses any crystalline or amorphous form, or mixtures thereof, which form possesses properties useful in SERD activity, it being well known in the art how to determine efficacy of a crystalline or amorphous form for the SERD activity by the standard tests described hereinafter.

It is generally known that crystalline materials may be analysed using conventional techniques such as X-Ray Powder Diffraction (hereinafter XRPD) analysis, Differential Scanning Calorimetry (hereinafter DSC), Thermal Gravimetric Analysis (hereinafter TGA), Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

As an example, the compound of Example 7 exhibits crystallinity and one crystalline form has been identified.

Accordingly, a further aspect of the invention is Form A of (E)-3-(4-(2-((S)-3-fluoro-2-methylpropyl)-3,3-dimethyl-2,3,4,9-tetrahydro-1H-pyrido[3,4-b]indol-1-yl)phenyl) acrylic acid (Example 7).

According to a further aspect of the present invention, there is provided a crystalline form, Form A of Example 7 which has an X-ray powder diffraction pattern with at least one specific peak at about 2-theta=4.5°.

According to a further aspect of the present invention, there is provided a crystalline form, Form A of Example 7 which has an X-ray powder diffraction pattern with at least one specific peak at about 2-theta=10.8°.

According to a further aspect of the present invention, there is provided a crystalline form, Form A of Example 7 which has an X-ray powder diffraction pattern with at least two specific peaks at about 2-theta=4.5 and 10.8°.

According to a further aspect of the present invention, there is provided a crystalline form, Form A of Example 7 which has an X-ray powder diffraction pattern with at specific peaks at about 2-theta=4.5, 4.8, 6.1, 7.9, 9.9, 10.8, 13.4, 14.0, 14.3 and 18.5°.

According to the present invention there is provided crystalline form, Form A of Example 7 which has an X-ray powder diffraction pattern substantially the same as the X-ray powder diffraction pattern shown in FIG. 1.

According to a further aspect of the present invention, there is provided a crystalline form, Form A of Example 7 which has an X-ray powder diffraction pattern with at least one specific peak at about 2-theta=4.5° plus or minus 0.2° 2-theta.

According to a further aspect of the present invention, there is provided a crystalline form, Form A of Example 7 which has an X-ray powder diffraction pattern with at least one specific peak at about 2-theta=10.8° plus or minus 0.2° 2-theta.

According to a further aspect of the present invention, there is provided a crystalline form, Form A of Example 7 which has an X-ray powder diffraction pattern with at least two specific peaks at about 2-theta=4.5 and 10.8° plus or minus 0.2° 2-theta.

According to a further aspect of the present invention, there is provided a crystalline form, Form A of Example 7 which has an X-ray powder diffraction pattern with at specific peaks at about 2-theta=4.5, 4.8, 6.1, 7.9, 9.9, 10.8, 13.4, 14.0, 14.3 and 18.5° plus or minus 0.2° 2-theta.

Furthermore, Example 1 also shows crystallinity.

According to the present invention there is provided a crystalline form, Form B, of (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid which has an X-ray powder diffraction pattern with at least one specific peak at about 2-theta=8.4°.

According to the present invention there is provided a crystalline form, Form B, of (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid which has an X-ray powder diffraction pattern with at least one specific peak at about 2-theta=10.9°.

According to the present invention there is provided a crystalline form, Form B, of (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid which has an X-ray powder diffraction pattern with at least two specific peaks at about 2-theta=8.4° and 10.9°.

According to the present invention there is provided a crystalline form, Form B, of (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid which has an X-ray powder diffraction pattern with specific peaks at about 2-theta=8.4, 10.9, 18.3, 24.0 and 14.0°.

According to the present invention there is provided a crystalline form, Form B, of (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid which has an X-ray powder diffraction pattern with specific peaks at about 2-theta=8.4, 10.9, 18.3, 24.0, 14.0, 19.0, 14.4, 13.0, 15.3, 20.6°.

According to the present invention there is provided crystalline form, Form B of (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid which has an X-ray powder diffraction pattern substantially the same as the X-ray powder diffraction pattern shown in FIG. 2.

According to the present invention there is provided crystalline form, Form B, of (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid which has an X-ray powder diffraction pattern with at least one specific peak at 2-theta=8.4° plus or minus 0.2° 2-theta.

According to the present invention there is provided a crystalline form, Form B, of (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid which has an X-ray powder diffraction pattern with at least one specific peak at 2-theta=10.9° plus or minus 0.2° 2-theta.

According to the present invention there is provided a crystalline form, Form B, of (E)-3-(3,5-difluoro-4-((1R,3R)-

2-(2-fluoro-2-methylpropyl)-3-methyl-2,3,4,9-tetrahydro-1H-pyrido[3,4-b]indol-1-yl)phenyl)acrylic acid which has an X-ray powder diffraction pattern with at least two specific peaks at 2-theta=8.40 and 10.90 wherein said values may be plus or minus 0.2° 2-theta.

According to the present invention there is provided a crystalline form, Form B, of (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid which has an X-ray powder diffraction pattern with specific peaks at about 2-theta=8.4, 10.9, 18.3, 24.0 and 14.0° wherein said values may be plus or minus 0.2° 2-theta.

According to the present invention there is provided a crystalline form, Form B, of (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid which has an X-ray powder diffraction pattern with specific peaks at 2-theta=8.4, 10.9, 18.3, 24.0, 14.0, 19.0, 14.4, 13.0, 15.3, 20.6° wherein said values may be plus or minus 0.2° 2-theta.

When it is stated that the present invention relates to a crystalline form of Example 1 Form B, the degree of crystallinity is conveniently greater than about 60%, more conveniently greater than about 80%, preferably greater than about 90% and more preferably greater than about 95%. Most preferably the degree of crystallinity is greater than about 98%.

Furthermore, when it is stated that the present invention relates to a crystalline form of Example 1 Form B, the material is preferably substantially free of other crystalline forms or amorphous material. By "substantially free", we mean conveniently greater than about 60%, more conveniently greater than about 80%, preferably greater than about 90%, more preferably greater than about 95% and most preferably greater than about 98% of single polymorph.

It will be understood that 2-theta values of the X-ray powder diffraction patterns may vary slightly from one machine to another or from one sample to another, and so the values quoted are not to be construed as absolute.

It is known that an X-ray powder diffraction pattern may be obtained which has one or more measurement errors depending on measurement conditions (such as equipment or machine used). In particular, it is generally known that intensities in an X-ray powder diffraction pattern may fluctuate depending on measurement conditions. Therefore it should be understood that the crystalline Forms of the present invention described above, unless otherwise stated, are not limited to the crystals that provide X-ray powder diffraction patterns identical to the X-ray powder diffraction pattern shown in the relevant Figures, and any crystals providing X-ray powder diffraction patterns substantially the same as those shown in these Figures fall within the scope of the present invention. A person skilled in the art of X-ray powder diffraction is able to judge the substantial identity of X-ray powder diffraction patterns.

Persons skilled in the art of X-ray powder diffraction will also realise that the relative intensity of peaks can be affected by, for example, grains above 30 microns in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values (see Jenkins, R & Snyder, R. L. 'Introduction to X-Ray Powder Diffractometry' John Wiley & Sons 1996; Bunn, C. W. (1948), Chemical Crystallography, Clarendon Press, London; Klug, H. P. & Alexander, L. E. (1974), X-Ray Diffraction Procedures).

Generally, a measurement error of a diffraction angle in an X-ray powder diffractogram is approximately plus or minus 0.2° 2-theta, and such degree of a measurement error should be taken into account when considering the X-ray powder diffraction data. Furthermore, it should be understood that intensities might fluctuate depending on experimental conditions and sample preparation (preferred orientation).

Particular compounds of the invention are each of the Examples, each of which provides a further independent aspect of the invention. Further particular compounds of the invention are pharmaceutically-acceptable salt(s) of each of the Examples, each of which provides a further independent aspect of the invention.

According to a further aspect of the invention there is provided a compound of the Formula (I), which is obtainable by following any of the Examples as disclosed herein.

A further feature is any of the scopes defined herein with the proviso that specific Examples, such as Example 1, 2, 3 etc. are individually disclaimed.

It will be appreciated by those skilled in the art that certain compounds of Formula (I) contain asymmetrically substituted carbon atoms, and accordingly may exist in, and be isolated in, optically-active and racemic forms. Some compounds of Formula (I) may exhibit polymorphism. It is to be understood that the present invention encompasses any racemic, optically-active, polymorphic or stereoisomeric form, or mixtures thereof, which form possesses properties useful as SERDs, it being well known in the art how to prepare optically-active forms (for example, by resolution of the racemic form by recrystallization techniques, by synthesis from optically-active starting materials, by chiral synthesis, by enzymatic resolution, by biotransformation, or by chromatographic separation using a chiral stationary phase) and how to determine efficacy as SERDs by the standard tests described hereinafter.

It is to be understood that certain compounds of Formula (I) defined above may exhibit the phenomenon of tautomerism. It is to be understood that the present invention includes in its definition any such tautomeric form, or a mixture thereof, which possesses SERD activity and is not to be limited merely to any one tautomeric form utilised within the formulae drawings or named in the Examples. In general, just one of any such tautomeric forms is named in the Examples that follow hereinafter or is presented in any relevant formulae drawings that follow hereinafter.

The present invention is intended to include all isotopes of atoms occurring in the present compounds. Isotopes will be understood to include those atoms having the same atomic number but different mass numbers. For example, isotopes of hydrogen include tritium and deuterium. Isotopes of carbon include $^{13}C$ and $^{14}C$. A deuterated version of Example 1 is described in Example 10.

A suitable pharmaceutically-acceptable salt of a compound of the Formula (I) is, for example, an alkali or alkaline earth metal salt such as a sodium, calcium or magnesium salt, or an ammonium salt, or a salt with an organic base such as methylamine, dimethylamine, trimethylamine, piperidine, morpholine or tris-(2-hydroxyethyl)amine. Further suitable pharmaceutically-acceptable salts of a compound of the Formula (I) may be other metal salts, such as potassium, zinc, or other such metal cations known in the art. In one aspect of the invention, a pharmaceutically-acceptable salt of a compound of Formula (I) is a salt with a metal cation, an ammonium salt or a salt with an organic base.

A further suitable pharmaceutically-acceptable salt of a compound of the Formula (I) is, for example, a salt formed within the human or animal body after administration of a compound of the Formula (I).

A suitable pharmaceutically-acceptable salt of a compound of the Formula (I) may also be, for example, an acid-addition salt of a compound of the Formula (I), for example an acid-addition salt with a strong inorganic or organic acid such as hydrochloric, hydrobromic, sulphuric or trifluoroacetic acid. Other potential suitable pharmaceutically-acceptable salt of a compound of the Formula (I) may also be as described below for Example 1. In another aspect of the invention, a pharmaceutically-acceptable salt of a compound of Formula (I) is an acid-addition salt.

Experiments looking at formation of salts of the compounds of Formula (I) examined the potential for Example 1 ((E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid) to form crystalline salts. The following acids and bases were tried: acetic acid, adipic acid, benzene sulfonic acid, benzoic acid, cinnamic acid, citric acid, D,L-lactic acid, ethane disulfonic acid, ethane sulfonic acid, fumaric acid, hydrochloric acid, L-tartaric acid, maleic acid, malic acid, malonic acid, methane sulfonic acid, napadisylic acid, phosphoric acid, saccharin, succinic acid, sulphuric acid, toluene sulfonic acid, calcium acetate, diethylamine, ethanolamine, ethylenediamine, hydroxyethylpyrrolidine, magnesium acetate, meglumine, piperazine, potassium hydroxide, sodium hydroxide, t-butylamine, triethanolamine, tris(hydroxymethyl)aminomethane (Tris) and N,N-diethylethanolamine.

Of the above acids and bases, isolatable solid salts were not always obtainable, or not obtainable in crystalline form in the experimental conditions employed. Preferred salts of Example 1 include those which may be isolated in crystalline form, for example, benzene sulfonic acid salt (besylate salt), succinic acid salt (succinate salt) and maleic acid salt (maleate salt).

In one aspect, suitable salts of Example 1 may include besylate, succinate and maleate. In another aspect, a suitable salt of Example 1 may be the maleate salt, which is described in Example 11.

It is further to be understood that a suitable pharmaceutically-acceptable co-crystal of a compound of the Formula (I) also forms an aspect of the present invention. For the avoidance of doubt, the term co-crystal (or cocrystal) refers to a multicomponent system in which there exists a host API (active pharmaceutical ingredient) molecule or molecules and a guest (or co-former) molecule or molecules. In a co-crystal, both the API molecule and the guest (or co-former) molecule exist as a solid at room temperature when alone in their pure form (in order to distinguish the co-crystal from solvates or hydrates). Salts, in which significant or complete proton exchange occurs between the API molecule and the guest molecule, are excluded from this particular definition. In a co-crystal, the API and co-former molecules interact by hydrogen bonding and possibly other non-covalent interactions. Pharmaceutically acceptable co-formers include neutral molecules such as nicotinamide, resorcinol and xylenols, as well as ionisable molecules such as oxalic acid, 3,5-dihydroxybenzoic acid and isoquinoline (the extent of proton exchange determining whether a salt or co-crystal is formed). It may be noted that a co-crystal may itself form solvates, including hydrates.

It is further to be understood that a suitable pharmaceutically-acceptable solvate of a compound of the Formula (I) also forms an aspect of the present invention. A suitable pharmaceutically-acceptable solvate is, for example, a hydrate such as a hemi-hydrate, a mono-hydrate, a di-hydrate or a tri-hydrate or an alternative quantity thereof.

It is further to be understood that a suitable pharmaceutically-acceptable pro-drug of a compound of the Formula (I) also forms an aspect of the present invention. Accordingly, the compounds of the invention may be administered in the form of a pro-drug, which is a compound that is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in-vivo cleavable ester derivatives that may be formed at a carboxy group in a compound of the Formula (I).

Accordingly, the present invention includes those compounds of the Formula (I) as defined hereinbefore when made available by organic synthesis and when made available within the human or animal body by way of cleavage of a pro-drug thereof. Accordingly, the present invention includes those compounds of the Formula (I) that are produced by organic synthetic means and also such compounds that are produced in the human or animal body by way of metabolism of a precursor compound, that is a compound of the Formula (I) may be a synthetically-produced compound or a metabolically-produced compound.

A suitable pharmaceutically-acceptable pro-drug of a compound of the Formula (I) is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*. 8, 1-38 (1992);
e) H. Bundgaard, et al., *Journal of Pharmaceutical Sciences*, 77, 285 (1988);
f) N. Kakeya, et al., *Chem. Pharm. Bull.,* 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically-acceptable pro-drug of a compound of the Formula I that possesses a carboxy group is, for example, an in vivo cleavable ester thereof. An in vivo cleavable ester of a compound of the Formula I containing a carboxy group is, for example, a pharmaceutically-acceptable ester which is cleaved in the human or animal body to produce the parent acid. Suitable pharmaceutically-acceptable esters for carboxy include (1-6C)alkyl esters such as methyl, ethyl and tert-butyl, (1-6C)alkoxymethyl esters such as methoxymethyl esters, (1-6C)alkanoyloxymethyl esters such as pivaloyloxymethyl esters, 3-phthalidyl esters, (3-8C)cycloalkylcarbonyloxy-(1-6C)alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and (1-6C) alkoxycarbonyloxy-(1-6C)alkyl esters such as methoxycarbonyloxymethyl and 1-methoxycarbonyloxyethyl esters.

A suitable pharmaceutically-acceptable pro-drug of a compound of the Formula I which have a carboxy group is for example an in vivo cleavable amide such as a N—$C_{1-6}$alkyl and N,N-di-($C_{1-6}$alkyl)amide such as N-methyl, N-ethyl, N-propyl, N,N-dimethyl, N-ethyl-N-methyl or N,N-diethylamide.

The in vivo effects of a compound of the Formula (I) may be exerted in part by one or more metabolites that are formed within the human or animal body after administration of a compound of the Formula (I). As stated hereinbefore, the in vivo effects of a compound of the Formula (I) may also be exerted by way of metabolism of a precursor compound (a pro-drug).

Two isomeric active metabolites of Example 1 have been identified from in-vitro human systems as shown below (where the isomers are diastereomeric as a result of both configurations existing at the carbon marked with a *), and synthesis of both isomers is set out in Examples 14A and B herein:

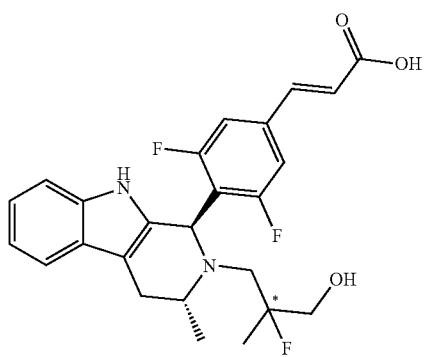 [SMILES: C[C@@H]1Cc2c([nH]c3ccccc23)[C@@H](c2c(F)cc(/C=C/C(=O)O)cc2F)N1CC(C)(F)CO]

Additionally, the following compound is believed to be an active metabolite in some species, such as in mouse:

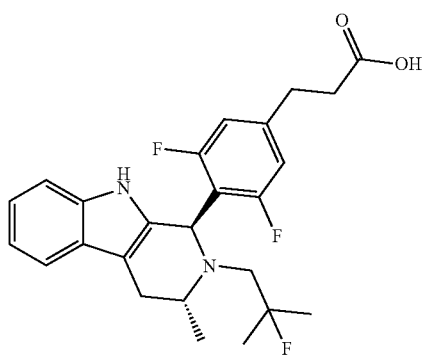 [SMILES: C[C@@H]1Cc2c([nH]c3ccccc23)[C@@H](c2c(F)cc(CCC(=O)O)cc2F)N1CC(C)(C)F]

Such active metabolites form further independent aspects of the invention.

For the avoidance of doubt it is to be understood that where in this specification a group is qualified by 'hereinbefore defined' or 'defined hereinbefore' the said group encompasses the first occurring and broadest definition as well as each and all of the particular definitions for that group.

Particular novel compounds of the invention include, for example, compounds of the Formula (I), or pharmaceutically-acceptable salts thereof, wherein, unless otherwise stated, each of $R^1$ and $R^2$, has any of the meanings defined hereinbefore or in the following statements:

In one aspect $R^1$ is hydrogen. In another aspect $R^1$ is fluoro.

In one aspect $R^2$ is hydrogen. In another aspect $R^2$ is fluoro.

In one aspect both $R^1$ and $R^2$ are hydrogen. In another aspect both $R^1$ and $R^2$ are fluoro. In another aspect $R^1$ is hydrogen and $R^2$ is fluoro.

In one aspect $R^3$ is hydrogen. In another aspect $R^3$ is methyl.

In one aspect $R^4$ is hydrogen and $R^5$ is fluoro. In another aspect $R^5$ is hydrogen and $R^4$ is fluoro.

Particular compounds of the invention are, for example, the compounds of the Formula (I) that are disclosed within the Examples that are set out hereinafter.

For example, a particular compound of the invention is a compound of the Formula (I) selected from any one of the following:—

(E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid;

(E)-3-(4-((1R,3R)-2-(2-fluoro-2-methylpropyl)-3-methyl-2,3,4,9-tetrahydro-1H-pyrido[3,4-b]indol-1-yl)phenyl)acrylic acid;

(E)-3-(3,5-difluoro-4-((1R,3R)-2-((S)-3-fluoro-2-methylpropyl)-3-methyl-2,3,4,9-tetrahydro-1H-pyrido[3,4-b]indol-1-yl)phenyl)acrylic acid;

(E)-3-(4-((1R,3R)-2-((S)-3-fluoro-2-methylpropyl)-3-methyl-2,3,4,9-tetrahydro-1H-pyrido[3,4-b]indol-1-yl)phenyl)acrylic acid;

(E)-3-(3,5-difluoro-4-(2-((S)-3-fluoro-2-methylpropyl)-3,3-dimethyl-2,3,4,9-tetrahydro-1H-pyrido[3,4-b]indol-1-yl)phenyl)acrylic acid;

(E)-3-(3,5-difluoro-4-(2-(2-fluoro-2-methylpropyl)-3,3-dimethyl-2,3,4,9-tetrahydro-1H-pyrido[3,4-b]indol-1-yl)phenyl)acrylic acid;

(E)-3-(4-(2-((S)-3-fluoro-2-methylpropyl)-3,3-dimethyl-2,3,4,9-tetrahydro-1H-pyrido[3,4-b]indol-1-yl)phenyl)acrylic acid;

(E)-3-(4-(2-(2-fluoro-2-methylpropyl)-3,3-dimethyl-2,3,4,9-tetrahydro-1H-pyrido[3,4-b]indol-1-yl)phenyl)acrylic acid;

(E)-3-(3-fluoro-4-(2-((S)-3-fluoro-2-methylpropyl)-3,3-dimethyl-2,3,4,9-tetrahydro-1H-pyrido[3,4-b]indol-1-yl)phenyl)acrylic acid;

or a pharmaceutically-acceptable salt thereof.

A further particular compound of the invention is a compound of the Formula (I) selected from any one of the following:—

(E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid;

(E)-3-(4-((1R,3R)-2-(2-fluoro-2-methylpropyl)-3-methyl-2,3,4,9-tetrahydro-1H-pyrido[3,4-b]indol-1-yl)phenyl)acrylic acid;

(E)-3-(3,5-difluoro-4-((1R,3R)-2-((S)-3-fluoro-2-methylpropyl)-3-methyl-2,3,4,9-tetrahydro-1H-pyrido[3,4-b]indol-1-yl)phenyl)acrylic acid;

(E)-3-(4-((1R,3R)-2-((S)-3-fluoro-2-methylpropyl)-3-methyl-2,3,4,9-tetrahydro-1H-pyrido[3,4-b]indol-1-yl)phenyl)acrylic acid;

(E)-3-(3,5-difluoro-4(1R)-(2-((S)-3-fluoro-2-methylpropyl)-3,3-dimethyl-2,3,4,9-tetrahydro-1H-pyrido[3,4-b]indol-1-yl)phenyl)acrylic acid;
(E)-3-(3,5-difluoro-4(1R)-(2-(2-fluoro-2-methylpropyl)-3,3-dimethyl-2,3,4,9-tetrahydro-1H-pyrido[3,4-b]indol-1-yl)phenyl)acrylic acid;
(E)-3-(4(1R)-(2-((S)-3-fluoro-2-methylpropyl)-3,3-dimethyl-2,3,4,9-tetrahydro-1H-pyrido[3,4-b]indol-1-yl)phenyl)acrylic acid;
(E)-3-(4(1R)-(2-(2-fluoro-2-methylpropyl)-3,3-dimethyl-2,3,4,9-tetrahydro-1H-pyrido[3,4-b]indol-1-yl)phenyl)acrylic acid;
(E)-3-(3-fluoro-4(1R)-(2-((S)-3-fluoro-2-methylpropyl)-3,3-dimethyl-2,3,4,9-tetrahydro-1H-pyrido[3,4-b]indol-1-yl)phenyl)acrylic acid; and
(E)-3-[4-[(1R,3R)-1-deuterio-2-(2-fluoro-2-methyl-propyl)-3-methyl-4,9-dihydro-3H-pyrido[3,4-b]indol-1-yl]-3,5-difluoro-phenyl]prop-2-enoic acid;
or a pharmaceutically-acceptable salt thereof.

A particular pharmaceutically-acceptable salt of the invention is (1R,3R)-1-{4-[(E)-2-carboxyethenyl]-2,6-difluorophenyl}-2-(2-fluoro-2-methylpropyl)-3-methyl-2,3,4,9-tetrahydro-1H-beta-carbolin-2-ium maleate.

Another aspect of the present invention provides a process for preparing a compound of the Formula (I), or a pharmaceutically-acceptable salt thereof. A suitable process is illustrated by the following representative process variants in which, unless otherwise stated, $R^1$ to $R^5$ have any of the meanings defined hereinbefore. Necessary starting materials may be obtained by standard procedures of organic chemistry. The preparation of such starting materials is described in conjunction with the following representative process variants and within the accompanying Examples. Alternatively, necessary starting materials are obtainable by analogous procedures to those illustrated which are within the ordinary skill of an organic chemist.

Compounds of formula (I) are conveniently made by hydrolysis of an ester derivative of formula (II), wherein $R^6$ is (1-6C) alkyl, such as methyl. Hydrolysis is conveniently carried out in the presence of base such as using sodium hydroxide in a suitable solvent (such as aqueous THF and MeOH (or another similar alcohol), or such as an aqueous alcohol for example aqueous isopropanol) and a suitable temperature, conveniently room temperature.

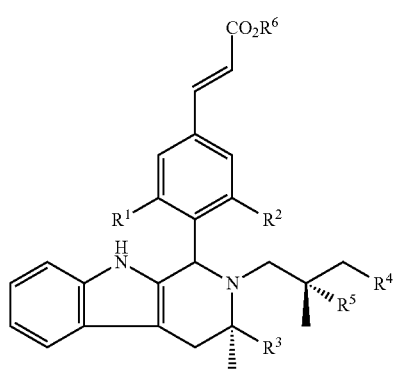

(II)

Compounds of formula (II) may be made by, for example:
a) reaction of a compound of formula (III) with a compound of formula (IV) under conditions known in the art as suitable for Pictet-Spengler reactions (such as in the presence of acid (such as acetic acid) and in a suitable solvent (for example toluene) and a suitable temperature (such as 80° C.)); or

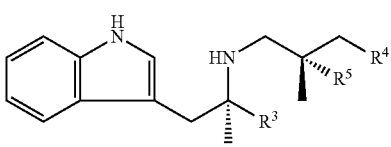

(III)

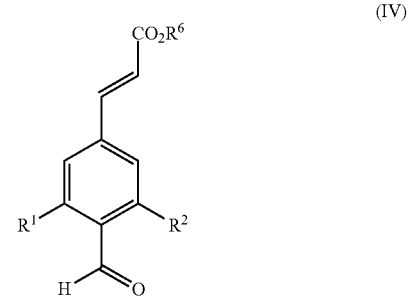

(IV)

b) by reaction of a compound of formula (V) with a compound of formula (VI), where LG is a leaving group known in the art such as halide or trifluoromethanesulfonate (triflate), conveniently triflate, in the presence of base (for example an amine base such as N-ethyl-N-isopropylpropan-2-amine) and a suitable polar solvent (such as dioxane) at a suitable temperature (such as from room temperature to 90° C.).

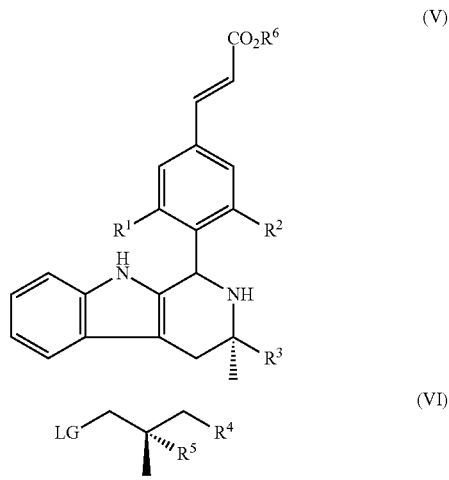

(V)

(VI)

Compounds of formula (III) may be prepared by reaction of a compound of formula (VII) with a compound of formula (VI) under conditions as described for the reaction of compounds of formulae (V) and (VI) above.

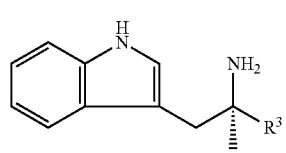

(VII)

Compounds of formula (IV) may be prepared by reaction of a compound of formula (VIII) with an alkyl acrylate ester (such as methyl acrylate when $R^6$ is methyl) under conditions known in the art for a Heck reaction; that is in the presence of an aryl phosphine (eg tri-o-tolylphosphine), a palladium catalyst (such as palladium (II) acetate and base (such as triethylamine) in a suitable solvent (such as DMA) and at a suitable temperature (eg 80° C.).

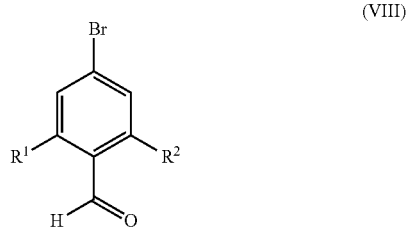

(VIII)

Compounds of formula (V) may be prepared by reaction of a compound of formula (VII) with a compound of formula (IV) using conditions similar to those described for the reaction of compounds of formulae (III) and (IV) above.

Compounds of formula (VI) where LG is triflate may be prepared as shown below in Schemes 1 and 2. Other compound of formula (VI) where LG is other than triflate may be prepared by similar methods known in the art.

Scheme 1

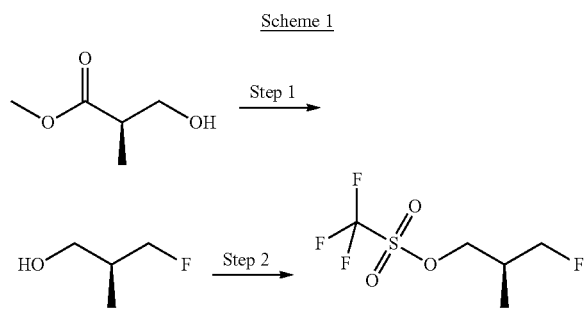

Step 1: Fluorinating agent, e.g. N,N-diethyl-1,1,2,3,3,3-hexafluoropropan-1-amine/DCM/RT, then reducing agent, e.g. lithium aluminium hydride/THF/RT
Step 2: Trifluoromethanesulfonic anhydride/base, e.g. 2,6-lutidine/DCM/0° C.

Scheme 2

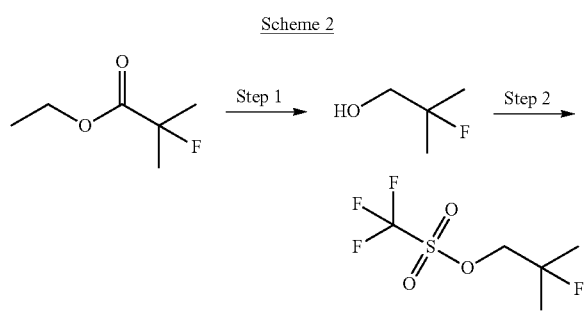

Step 1: Reducing agent, e.g. lithium aluminium hydride/ether/0° C.
Step 2: Trifluoromethanesulfonic anhydride/base, e.g. 2,6-lutidine/DCM/−10° C.

Compounds of formula (I) are chiral. It will be understood by the skilled person that stereoselective reactions may be used to obtain the desired isomers. Alternatively, stereochemistry may be adjusted by suitable means, such as by epimerisation from cis to trans isomers via acidification of an intermediate with protected amine group as illustrated in Example 4 herein (and described for example in J. Org. Chem. 2009, 74, 2771-2779).

In a further aspect of the invention there is provided a process for making a compound of formula (I) comprising hydrolysis of a compound of formula (II), conveniently in the presence of base.

It is to be understood that other permutations of the process steps in the process variants described above are also possible.

It is to be understood that any compound of Formula (I) obtained by any of the processes described hereinbefore can be converted into another compound of the Formula (I) if required.

When a pharmaceutically-acceptable salt of a compound of the Formula (I) is required it may be obtained by, for example, reaction of said compound with a suitable base.

When a pharmaceutically-acceptable pro-drug of a compound of the Formula (I) is required, it may be obtained using a conventional procedure. For example, an in vivo cleavable ester of compound of the Formula (I) may be obtained by, for example, reaction of a compound of the Formula (I) containing a carboxy group with a pharmaceutically-acceptable alcohol. Further information on pro-drugs has been provided hereinbefore.

It will also be appreciated that, in some of the reactions mentioned hereinbefore, it may be necessary or desirable to protect any sensitive groups in the compounds. The instances where protection is necessary or desirable, and suitable methods for protection, are known to those skilled in the art. Conventional protecting groups may be used in accordance with standard practice (for illustration see T.W. Green, Protective Groups in Organic Synthesis, John Wiley and Sons, 1991). Thus, if reactants include groups such as amino, carboxy or hydroxy, it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Certain of the intermediates (for example, compounds of the Formulae II, III, IV, V, VI, VII and VIII, particularly compounds of formula II, III and/or V) defined herein are novel and these are provided as a further feature of the invention.

Biological Assays—

The following assays were used to measure the effects of the compounds of the present invention.

ERα Binding Assay

The ability of compounds to bind to isolated Estrogen Receptor Alpha Ligand binding domain (ER alpha—LBD (GST)) was assessed in competition assays using a LanthaScreen™ Time-Resolved Fluorescence Resonance Energy Transfer (TR-FRET) detection end-point. For the LanthaScreen TR-FRET endpoint, a suitable fluorophore (Fluormone ES2, Product code P2645) and recombinant human Estrogen Receptor alpha ligand binding domain (Product code PV4543) were purchased from Invitrogen and used to measure compound binding. The assay principle is that ER alpha-LBD (GST) is added to a fluorescent ligand to form a receptor/fluorophore complex. A terbium-labelled anti-GST antibody (Product code PV3551) is used to indirectly label the receptor by binding to its GST tag, and competitive binding is detected by a test compounds' ability to displace the fluorescent ligand resulting in a loss of TR-FRET signal between the Tb-anti-GST antibody and the tracer. The assay was performed as follows with all reagent additions carried out using the Beckman Coulter BioRAPTR FRD microfluidic workstation:—

1. Acoustic dispense 120 nl of the test compound into a black low volume 384 well assay plates.
2. Prepare 1×ER alpha-LBD/Tb-antiGST Ab in ES2 screening buffer and incubate for 20 minutes.
3. Add 1× fluorophore to the ER alpha-LBD/Tb-antiGST Ab solution prior to use.
4. Dispense 12 µl of the 1×AR-LBD/Tb-anti-GST Ab/Fluorophore reagent into each well of the assay plate
5. Cover the assay plate to protect the reagents from light and evaporation, and incubate at room temperature for 1 hour.
6. Excite at 337 nm and measure the fluorescent emission signal of each well at 490 nm and 520 nm using the BMG PheraSTAR.

Compounds were dosed directly from a compound source microplate containing serially diluted compound (4 wells containing 10 mM, 0.1 mM, 1 µM and 10 nM final compound respectively) to an assay microplate using the Labcyte Echo 550. The Echo 550 is a liquid handler that uses acoustic technology to perform direct microplate-to-microplate transfers of DMSO compound solutions and the system can be programmed to transfer multiple small nL volumes of compound from the different source plate wells to give the desired serial dilution of compound in the assay which is then back-filled to normalise the DMSO concentration across the dilution range. In total 120 nL of compound plus DMSO is added to each well and compounds were tested in a 12-point concentration response format over a final compound concentration range of 100, 29.17, 10.42, 2.083, 1, 0.292, 0.104, 0.02083, 0.01, 0.002917, 0.001042, 0.0001 µM, respectively. TR-FRET dose response data obtained with each compound was exported into a suitable software package (such as Origin or Genedata) to perform curve fitting analysis. Competitive ER alpha binding was expressed as an $IC_{50}$ value. This was determined by calculation of the concentration of compound that was required to give a 50% reduction in tracer compound binding to ER alpha-LBD.

MCF-7 ER Down Regulation Assay

The ability of compounds to down-regulate Estrogen Receptor (ER) numbers was assessed in a cell based immuno-fluorescence assay using the MCF-7 human ductal carcinoma breast cell line. MCF-7 cells were revived directly from a cryovial (approx $5 \times 10^6$ cells) in Assay Medium (phenol red free Dulbecco's Modified Eagle's medium (DMEM) (Sigma D5921) containing 2 mM L-Glutamine and 5% (v/v) Charcoal/Dextran treated foetal calf serum Cells were syringed once using a sterile 18 G×1.5 inch (1.2×40 mm) broad gauge needle and cell density was measured using a Coulter Counter (Beckman). Cells were further diluted in Assay Medium to a density of $3.75 \times 10^4$ cells per ml and 40 µl per well added to transparent bottomed, black, tissue culture treated 384 well plates (Costar, No. 3712) using a Thermo Scientific Matrix WellMate or Thermo Multidrop. Following cell seeding, plates were incubated overnight at 37° C., 5% $CO_2$ (Liconic carousel incubator). Test data was generated using the LabCyte Echo® model 555 compound reformatter which is part of an automated workcell (Integrated Echo 2 workcell). 10 mM compound stock solutions of the test compounds were used to generate a 384 well compound dosing plate (Labcyte P-05525-CV1). 40 µl of each of the 10 mM compound stock solutions was dispensed into the first quadrant well and then 1:100 step-wise serial dilutions in DMSO were performed using a Hydra II (MATRIX UK) liquid handling unit to give 40 ul of diluted compound into quadrant wells 2 (0.1 mM), 3 (1 µM) and 4 (0.01 µM), respectively. 40 µl of DMSO added to wells in row P on the source plate allow for DMSO normalisation across the dose range. To dose the control wells 40 µl of DMSO was added to row O1 and 40 µl of 100 µM Faslodex® in DMSO was added to row O3 on the compound source plate. The Echo uses acoustic technology to perform direct microplate-to-microplate transfers of DMSO compound solutions to assay plates. The system can be programmed to transfer volumes as low as 2.5 nL in multiple increments between microplates and in so doing generates a serial dilution of compound in the assay plate which is then back-filled to normalise the DMSO concentration across the dilution range. Compounds were dispensed onto the cell plates with a compound source plate prepared as above producing a 12 pt duplicate 3 µM to 3 pM dose range with 3 fold dilutions and one final 10 fold dilution using the Integrated Echo 2 workcell. The maximum signal control wells were dosed with DMSO to give a final concentration of 0.3% and the minimum signal control wells were dosed with Faslodex® to give a final concentration of 100 nM accordingly. Plates were further incubated for 18-22 hours at 37° C., 5% $CO_2$ and then fixed by the addition of 20 µl of 11.1% (v/v) formaldehyde solution (in phosphate buffered saline (PBS)) giving a final formaldehyde concentration of 3.7% (v/v). Cells were fixed at room temperature for 20 mins before being washed two times with 250 µl PBS/Proclin (PBS with a Biocide preservative) using a BioTek platewasher, 40 µl of PBS/Proclin was then added to all wells and the plates stored at 4° C. The fixing method described above was carried out on the Integrated Echo 2 workcell. Immunostaining was performed using an automated AutoElisa workcell. The PBS/Proclin was aspirated from all wells and the cells permeabilised with 40 µl PBS containing 0.5% Tween™ 20 (v/v) for 1 hour at room temperature. The plates were washed three times in 250 µl of PBS/0.05% (v/v) Tween 20 with Proclin (PBST with a Biocide preservative) and then 20 µl of ERα (SP1) Rabbit monoclonal antibody (Thermofisher) 1:1000 in PBS/Tween™/3% (w/v) Bovine Serum Albumin was added. The plates were incubated overnight at 4° C. (Liconic carousel incubator) and then washed three times in 250 µl of PBS/0.05% (v/v) Tween™ 20 with Proclin (PBST). The plates were then incubated with 20 µl/well of a goat anti-rabbit IgG AlexaFluor 594 or goat anti-rabbit AlexaFluor 488 antibody (Molecular Probes) with Hoechst at 1:5000 in PBS/Tween™/3% (w/v) Bovine Serum Albumin for 1 hr at room temperature. The plates were then washed three times in 250 µl of PBS/0.05% (v/v) Tween™ 20 with Proclin (PBST with a Biocide preservative). 20 µl of PBS was added to each well and the plates covered with a black plate seal and stored at 4° C. before being read. Plates were read using a Cellomics Arrayscan reading the 594 nm (24 hr time point) or 488 nm (5 hr timepoint) fluorescence to measure the ERα receptor level in each well. The mean total intensity was normalized for cell number giving the total intensity per cell. The data was exported into a suitable software package (such as Origin) to perform curve fitting analysis. Down-regulation of the ERα receptor was expressed as an $IC_{50}$ value and was determined by calculation of the concentration of compound that was required to give a 50% reduction of the average maximum Total Intensity signal.

Although the pharmacological properties of the compounds of the Formula (I) vary with structural change as expected, in general activity possessed by compounds of the Formula (I) may be demonstrated at the following concentrations or doses in one or more of the above tests.

The following data were generated for the Examples (the data below may be a result from a single experiment or an average of multiple repeat experiments):

TABLE A

| Example | ER binding $IC_{50}$ value | ER down regulation $IC_{50}$ value |
|---------|---------------------------|-----------------------------------|
| 1 | <0.64 | 0.14 |
| 2 | 1 | 0.85 |
| 3 | 1 | 0.4 |
| 4 | 1.6 | 0.99 |
| 5 | 0.2 | 0.57 |
| 6 | <1.3 | 0.44 |
| 7 | 5 | 1.7 |
| 8 | 2.2 | 3 |
| 9 | <1.2 | 1.5 |

MCF-7 In-vivo Xenograft Study with Example 1 as Single Agent and in Combination with an mTOR Inhibitor.

MCF7 cells ($5 \times 10^6$ cells suspended in 100 µl of RPMI cell medium) were implanted subcutaneously in the hind flank of immuno-compromised (SCID) mice the day after each mouse was surgically implanted with a 0.5 mg/21 day oestrogen pellet (Innovative Research, USA). Tumours were measured twice weekly and changes in tumour volume and growth inhibition were determined by bilateral Vernier calliper measurement (length×width) where length was taken to be the longest diameter across the tumour and width the corresponding perpendicular. Tumour volume was calculated using the formula (length×width)×√(length×width)×π/6).

Tumours were measured 13 days after cell implantation to allow randomisation of mice into test groups. Treatment with compounds began the day after (i.e. 14 days after cell implantation).

The mTOR inhibitor AZD2014 was dosed to different groups of mice at 15 mg/kg once daily every day orally (p.o.) at a volume of 0.1 ml per 10 g. Example 1 was dosed at 5 mg/kg once daily orally at 0.1 ml/10 g. One group of animals was dosed with vehicle p.o. to act as a control. Nine mice per group were used for active agents for the control group.

The data obtained from this study are shown in FIG. 10.

The effect of a combination of a compound of Formula (I) with an inhibitor of PI3Kα/δ may be studied in a similar manner to the combination with the mTOR inhibitor above.

HCC1428 Long Term Estrogen Deprived (HCC1428 LTED) Xenograft Efficacy Study

After a suitable period of cell culture, HCC1428 LTED cells ($1 \times 10^6$) were implanted subcutaneously in the hind flank of female immuno-compromised NSG mice (Jackson Labs, USA) that had undergone overectomy. Tumours were measured twice weekly and changes in tumour volume and growth inhibition were determined by bilateral Vernier calliper measurement (length×width) where length was taken to be the longest diameter across the tumour and width the corresponding perpendicular. Tumour volume was calculated using the formula (length×width)×√(length×width)×(π/6). Tumours were measured once weekly after cell implantation until the average size reached 150 mm³ at which point the mice were placed into randomised test groups, each group containing 10 mice. Treatment with compounds began the day after (day 62 in this study) and once weekly tumour measurement continued. Example 1 was dosed 25 mg/kg once daily every day orally (p.o.) at a volume of 0.1 ml per 10 g. Another group of animals was dosed with vehicle p.o. to act as a control.

After 28 days of dosing, control treated tumours grew on average by 220 mm³ (using geometric mean values) while tumours from mice treated by Example 1 decreased in size by 46 mm³ representing a 121% inhibition of tumour growth (P<0.001 by unpaired t-test).

To measure the levels of estrogen receptor protein in xenograft tumours, tumours samples were harvested 24 hrs post final dose of vehicle or example 1 treatment and snap frozen in liquid nitrogen. For protein extraction, tumour fragments were added to 700 ul of Invitrogen Cell Extraction buffer (FNN0011) with added Sigma Phosphatase inhibitors (No. 2 (P5726) and 3 (P0044) 1 in 100 dilution) and Roche Complete (11836145001) protease inhibitor (1 tablet per 50 mls), 1 mM dithiothreitol (DTT) in 2 ml sample tubes on wt ice. Homogenisation of the sample was done using a Mixermill (level 27/sec) and 3×2 mins cycles of homogenisation. Samples were spun briefly to ascertain complete homogenisation of the tumours. Homogenate was sonicated for 10 seconds and then spun down at top speed (13000 rpm) centrifuge for 15 mins. Levels of protein in the supernatent were measured and approx 45 ug of protein were run on a 15 well Bis-Tris Gels (4-12% Gels) using standard methods. Following protein separation and transfer onto nitrocellulose filter, estrogen receptor 68 kDa: ThermoFisher SP1 #9101S antibody was added, diluted 1:400 in milk/PBS/T and incubated overnight at 4° C. The filter was washed in 3×5 mins in ~20 ml of TBS/T 0.05% and a secondary anti-rabbit detection antibody was diluted 1:2000 in 5% marvel in TBS/T and incubate for 1 hr at RT. Signal was detected using chemiluminescent SuperSignal West Dura extended Duration substrate and quantified using Syngene software. Vinculin protein levels were measured as a loading control using V931 Sigma diluted 1:10,000 in marvel and an anti-mouse detection antibody. The results in FIGS. 11 and 12 show that a 60% decrease in ER levels were observed upon treatment with Example 1 relative to vehicle control.

According to a further aspect of the invention there is provided a pharmaceutical composition, which comprises a compound of the Formula (I), or a pharmaceutically-acceptable salt thereof, as defined hereinbefore in association with a pharmaceutically-acceptable diluent or carrier.

Suitable pharmaceutically-acceptable excipients for a tablet formulation include, for example, inert diluents, granulating and disintegrating agents, binding agents, lubricating agents, preservative agents and anti-oxidants. A further suitable pharmaceutically-acceptable excipient may be a chelating-agent. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may alternatively be in the form of hard gelatin capsules in which the active ingredient is mixed with an inert solid diluent, or as soft gelatin capsules in which the active ingredient is mixed with water or an oil.

Aqueous suspensions generally contain the active ingredient in finely powdered form together with one or more suspending agents, dispersing or wetting agents. The aqueous suspensions may also contain one or more preservatives, anti-oxidants, colouring agents, flavouring agents, and/or sweetening agents.

Oily suspensions may be formulated by suspending the active ingredient in a vegetable oil or in a mineral oil. The oily suspensions may also contain a thickening agent. Sweetening agents such as those set out above, and flavouring agents may be added to provide a palatable oral preparation. These compositions may be preserved by the addition of an anti-oxidant.

Dispersible powders and granules suitable for preparation of an aqueous suspension by the addition of water generally contain the active ingredient together with a dispersing or wetting agent, suspending agent and one or more preservatives. Additional excipients such as sweetening, flavouring and colouring agents, may also be present.

The pharmaceutical compositions of the invention may also be in the form of oil-in-water emulsions. The oily phase may be a vegetable oil or a mineral oil or a mixture of any of these. The emulsions may also contain sweetening, flavouring and preservative agents.

Syrups and elixirs may be formulated with sweetening agents, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent system.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient. Dry powder inhalers may also be suitable.

For further information on formulation the reader is referred to Chapter 25.2 in Volume 5 of Comprehensive Medicinal Chemistry (Corwin Hansch; Chairman of Editorial Board), Pergamon Press 1990.

In one aspect of the invention, the pharmaceutical composition described above comprises the compound of Example 1 [(E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid], or a pharmaceutically acceptable salt thereof. Conveniently, the compound of Example 1 is present in its polymorph described herein as crystalline Form B.

The process for synthesising (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid as set out in Example 1, recommends that the process is carried out in the absence of light and under a nitrogen atmosphere in order to avoid the formation of a degradation product.

The degradation product referred to, which is (R,E)-3-(3,5-difluoro-4-(2-(2-fluoro-2-methylpropyl)-3-methyl-4,9-dihydro-3H-pyrido[3,4-b]indol-2-ium-1-yl)phenyl)acrylate, has the following structure:

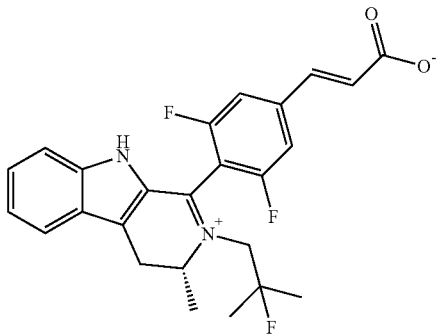

and is thought may be formed from Example 1 [(E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl) acrylic acid] by autooxidation in air via a free radical chain mechanism. For the avoidance of doubt, this degradation product is not believed to have significant SERD activity.

This compound could also be referred to as (E)-3-[3,5-difluoro-4-[(3R)-2-(2-fluoro-2-methyl-propyl)-3-methyl-4,9-dihydro-3H-pyrido[3,4-b]indol-2-ium-1-yl]phenyl]prop-2-enoate and a synthetic method for making it is given in Example 13.

The skilled person will appreciate that control of the formation of degradation products is essential to the safe production and storage of pharmaceuticals. Also, the skilled person will appreciate that certain compounds may degrade on storage, even after formulation into a pharmaceutical composition, and that such degradation may in some instances be controlled by the use of appropriate excipients in the pharmaceutical composition and/or by appropriate packaging of the final product. The skilled person will further appreciate that a final formulation which is developed for commercial use will need to be optimised for a number of characteristics, including chemical stability, but also including for instance physical stability and dissolution characteristics. Therefore such formulations will be developed in order to balance a number of different factors.

Suitably, compositions of (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid, or a pharmaceutically-acceptable salt thereof, include a compound which acts as an anti-oxidant.

Anti-oxidant compounds which are suitable for use in pharmaceutical compositions are known in the art, and include, for example, acetone sodium bisulfite; alpha lipoic acid; alpha tocopherol; ascorbic acid; ascorbyl palmitate; butylated hydroxyanisole; butylated hydroxytoluene; carotenes; citric acid monohydrate; dodecyl gallate; erythorbic acid; fumaric acid; glutathione; histidine; hypophosphorous acid; lactobionic acid; lipoic acid; malic acid; melatonin; methionine; d-mannose; monothioglycerol; octyl gallate; potassium metabisulfite; propionic acid; propyl gallate; sodium ascorbate; sodium bisulfite; sodium formaldehyde sulfoxylate; sodium metabisulfite; sodium sulfite; sodium thiosulfate; stannous chloride; sulfur dioxide; thymol; tocopherol; tocotrienols; ubiquinol; uric acid; vitamin E; and vitamin E polyethylene glycol succinate. Such compounds may exert their anti-oxidant effect by a variety of mechanisms, and one or more of these mechanisms may be more effective than others for any particular compound. Some anti-oxidants compounds, such as BHA, act as free-radical scavengers. Other anti-oxidants, such sodium metabisulfite and ascorbic acid are easily oxidised and so may be oxidised in preference to the active ingredient.

For example, where metal induced peroxide formation is involved in the oxidation mechanism, use of a chelating agent, such as for example EDTA (ethylenediaminetetraacetic acid), may be useful to remove any metal contaminants and thereby indirectly achieve a stabilising effect. Other metal-chelating agents are known in the art and include, for example, betadex sulfobutyl ether sodium; calcium acetate; citric acid monohydrate; cyclodextrins; disodium edetate; edetic acid; fumaric acid; galactose; glutamic acid; histidine; hydroxypropyl betadex; malic acid; pentetic acid; phytochelatin; poly(methyl vinyl ether/maleic anhydride); potassium citrate; sodium citrate dihydrate; sodium phosphate, dibasic; sodium phosphate, monobasic; tartaric acid; and trehalose.

For example, propyl gallate, sodium metabisulfite, ascorbic acid and butylated hydroxyanisole were included in exemplary formulations of Example 1. EDTA was also included. An example of such a formulation is provided as Example 12. Of these, compositions containing sodium metabisulfite appeared to be less stable than those with no anti-oxidant, after four weeks storage under a number of different heat and humidity conditions. Compositions containing ascorbic acid appeared to be the most stable after 4 weeks storage under a number of different heat and humidity conditions (as determined by Liquid Chromatography analysis, eg UHPLC).

Further suitable additives for formulations comprising the compound of Example 1, include using excipients with a low metal content, excipients with a low peroxide content, excipients such as mannitol which is a free-radical scavenger as well as a filler. The process of production of such a formulation may also impact stability. For example, for some active ingredients, ensuring intimate mixing of the active ingredient with stability-inducing excipients may be important in ensuring maximum stabilisation. Intimate mixing may be influenced by, for example, mixing speed, particle sizes and wet or dry mixing/granulation processes. An active ingredient may be granulated with an antioxidant and then mixed with other excipients. Antioxidants may also be added to any coating on the outside of a pharmaceutical composition.

In one aspect of the invention, there is provided a pharmaceutical composition comprising (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid or a pharmaceutically-acceptable salt thereof, in association with at least one pharmaceutically-acceptable diluents or carrier.

In one aspect of the invention, there is provided a pharmaceutical composition comprising (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid or a pharmaceutically-acceptable salt thereof, and also comprising an anti-oxidant. Suitably, ascorbic acid may be used as the anti-oxidant.

In one aspect of the invention, there is provided a pharmaceutical composition comprising (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid or a pharmaceutically-acceptable salt thereof, and also comprising a metal chelating agent. Suitably, EDTA may be used as a metal chelating agent.

In another aspect of the invention, there is provided a pharmaceutical composition comprising (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid or a pharmaceutically-acceptable salt thereof, an anti-oxidant and optionally further comprising a metal chelating agent.

In another aspect of the invention, there is provided a pharmaceutical composition comprising (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid or a pharmaceutically-acceptable salt thereof, in association with at least one pharmaceutically-acceptable diluent or carrier, wherein the composition contains less than 5% w/w of (R,E)-3-(3,5-difluoro-4-(2-(2-fluoro-2-methylpropyl)-3-methyl-4,9-dihydro-3H-pyrido[3,4-b]indol-2-ium-1-yl)phenyl)acrylate.

In another aspect of the invention, there is provided a pharmaceutical composition comprising (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid or a pharmaceutically-acceptable salt thereof, in association with at least one pharmaceutically-acceptable diluent or carrier, wherein the composition contains less than 2% w/w of (R,E)-3-(3,5-difluoro-4-(2-(2-fluoro-2-methylpropyl)-3-methyl-4,9-dihydro-3H-pyrido[3,4-b]indol-2-ium-1-yl)phenyl)acrylate.

In another aspect of the invention, there is provided a pharmaceutical composition comprising (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid or a pharmaceutically-acceptable salt thereof, in association with at least one pharmaceutically-acceptable diluent or carrier, wherein the composition contains less than 1% w/w of (R,E)-3-(3,5-difluoro-4-(2-(2-fluoro-2-methylpropyl)-3-methyl-4,9-dihydro-3H-pyrido[3,4-b]indol-2-ium-1-yl)phenyl)acrylate.

In another aspect of the invention, there is provided a pharmaceutical composition comprising (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid or a pharmaceutically-acceptable salt thereof, in association with at least one pharmaceutically-acceptable diluent or carrier, wherein the composition contains less than 0.5% w/w of (R,E)-3-(3,5-difluoro-4-(2-(2-fluoro-2-methylpropyl)-3-methyl-4,9-dihydro-3H-pyrido[3,4-b]indol-2-ium-1-yl)phenyl)acrylate.

In another aspect of the invention, there is provided a pharmaceutical composition comprising (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid or a pharmaceutically-acceptable salt thereof, in association with at least one pharmaceutically-acceptable diluents or carrier, wherein the composition contains less than 0.1% w/w of (R,E)-3-(3,5-difluoro-4-(2-(2-fluoro-2-methylpropyl)-3-methyl-4,9-dihydro-3H-pyrido[3,4-b]indol-2-ium-1-yl)phenyl)acrylate.

In another aspect of the invention, there is provided a pharmaceutical composition comprising (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid or a pharmaceutically-acceptable salt thereof, in association with at least one pharmaceutically-acceptable diluents or carrier, wherein the composition contains less than 0.05% w/w of (R,E)-3-(3,5-difluoro-4-(2-(2-fluoro-2-methylpropyl)-3-methyl-4,9-dihydro-3H-pyrido[3,4-b]indol-2-ium-1-yl)phenyl)acrylate.

In the above aspects, where the composition is described as containing less than 5% w/w, 2% w/w, 1% w/w, 0.5% w/w, 0.1% w/w or 0.05% w/w of (R,E)-3-(3,5-difluoro-4-(2-(2-fluoro-2-methylpropyl)-3-methyl-4,9-dihydro-3H-pyrido[3,4-b]indol-2-ium-1-yl)phenyl)acrylate then the skilled person will understand that this is intended to mean percentage weight for weight in comparison to the weight of (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid present in the composition.

The degradation product (R,E)-3-(3,5-difluoro-4-(2-(2-fluoro-2-methylpropyl)-3-methyl-4,9-dihydro-3H-pyrido[3,4-b]indol-2-ium-1-yl)phenyl)acrylate may therefore be used as a reference marker or reference standard in analytical techniques such as HPLC to monitor the stability of the compound of Example 1 or pharmaceutical compositions containing it.

The amount of active ingredient that is combined with one or more excipients to produce a single dosage form will necessarily vary depending upon the host treated and the particular route of administration. For example, oral administration to humans will generally require, for example, from 1 mg to 2 g of active agent (more suitably from 100 mg to 2 g, for example from 250 mg to 1.8 g, such as from 500 mg to 1.8 g, particularly from 500 mg to 1.5 g, conveniently from 500 mg to 1 g) to be administered compounded with an appropriate and convenient amount of excipients which may vary from about 3 to about 98 percent by weight of the total composition. It will be understood that, if a large dosage is required, multiple dosage forms may be required, for example two or more tablets or capsules, with the dose of active ingredient divided conveniently between them. Typically, unit dosage forms will contain about 10 mg to 0.5 g of a compound of this invention, although a unit dosage form may contain up to 1 g. Conveniently, a single solid dosage form may contain between 1 and 300 mg of active ingredient.

The size of the dose for therapeutic or prophylactic purposes of compounds of the present invention will naturally vary according to the nature and severity of the disease state, the age and sex of the animal or patient and the route of administration, according to well known principles of medicine.

In using compounds of the present invention for therapeutic or prophylactic purposes it will generally be administered so that a daily dose in the range, for example, 1 mg/kg to 100 mg/kg body weight is received, given if required in divided doses. In general, lower doses will be administered when a parenteral route is employed. Thus, for example, for intravenous administration, a dose in the range, for example, 1 mg/kg to 25 mg/kg body weight will generally be used. Similarly, for administration by inhalation, a dose in the range, for example, 1 mg/kg to 25 mg/kg body weight will be used. Oral administration is however preferred, particularly in tablet form.

In one aspect of the invention, compounds of the present invention or pharmaceutically-acceptable salts thereof, are administered as tablets comprising 10 mg to 100 mg of the compound of Formula (I) (or a pharmaceutically-acceptable salt thereof), wherein one or more tablets are administered as required to achieve the desired dose.

As stated above, it is known that signalling through ERα causes tumourigenesis by one or more of the effects of mediating proliferation of cancer and other cells, mediating angiogenic events and mediating the motility, migration and invasiveness of cancer cells. We have found that the compounds of the present invention possess potent anti-tumour activity which it is believed is obtained by way of antagonism and down-regulation of ERα that is involved in the signal transduction steps which lead to the proliferation and survival of tumour cells and the invasiveness and migratory ability of metastasising tumour cells.

Accordingly, the compounds of the present invention may be of value as anti-tumour agents, in particular as selective inhibitors of the proliferation, survival, motility, dissemination and invasiveness of mammalian cancer cells leading to inhibition of tumour growth and survival and to inhibition of metastatic tumour growth. Particularly, the compounds of the present invention may be of value as anti-proliferative and anti-invasive agents in the containment and/or treatment of solid tumour disease. Particularly, the compounds of the present invention may be useful in the prevention or treatment of those tumours which are sensitive to inhibition of ERα and that are involved in the signal transduction steps which lead to the proliferation and survival of tumour cells and the migratory ability and invasiveness of metastasising tumour cells. Further, the compounds of the present invention may be useful in the prevention or treatment of those tumours which are mediated alone or in part by antagonism and down-regulation of ERα, i.e. the compounds may be used to produce an ERα inhibitory effect in a warm blooded animal in need of such treatment.

According to a further aspect of the invention there is provided a compound of the Formula (I), or a pharmaceutically-acceptable salt thereof, as defined hereinbefore for use as a medicament in a warm-blooded animal such as man.

According to a further aspect of the invention, there is provided a compound of the Formula (I), or a pharmaceutically-acceptable salt thereof, as defined hereinbefore for use in the production of an anti-proliferative effect in a warm-blooded animal such as man.

According to a further aspect of the invention there is provided a compound of the Formula (I), or a pharmaceutically-acceptable salt thereof, as defined hereinbefore for use in a warm-blooded animal such as man as an anti-invasive agent in the containment and/or treatment of solid tumour disease.

According to a further aspect of the invention, there is provided the use of a compound of the Formula (I), or a pharmaceutically-acceptable salt thereof, as defined hereinbefore for the production of an anti-proliferative effect in a warm-blooded animal such as man.

According to a further aspect of the invention there is provided the use of a compound of the Formula (I), or a pharmaceutically-acceptable salt thereof, as defined hereinbefore in the manufacture of a medicament for use in the production of an anti-proliferative effect in a warm-blooded animal such as man.

According to a further aspect of the invention there is provided the use of a compound of the Formula (I), or a pharmaceutically-acceptable salt thereof, as defined hereinbefore in the manufacture of a medicament for use in a warm-blooded animal such as man as an anti-invasive agent in the containment and/or treatment of solid tumour disease.

According to a further aspect of the invention there is provided a method for producing an anti-proliferative effect in a warm blooded animal, such as man, in need of such treatment which comprises administering to said animal an effective amount of a compound of the Formula (I), or a pharmaceutically-acceptable salt thereof, as defined hereinbefore.

According to a further aspect of the invention there is provided a method for producing an anti-invasive effect by the containment and/or treatment of solid tumour disease in a warm blooded animal, such as man, in need of such treatment which comprises administering to said animal an effective amount of a compound of the Formula (I), or a pharmaceutically-acceptable salt thereof, as defined hereinbefore.

According to a further aspect of the invention, there is provided a compound of the Formula (I), or a pharmaceutically-acceptable salt thereof, as defined hereinbefore for use in the prevention or treatment of cancer in a warm blooded animal such as man.

According to a further aspect of the invention there is provided the use of a compound of the Formula (I), or a pharmaceutically-acceptable salt thereof, as defined hereinbefore in the manufacture of a medicament for use in the prevention or treatment of cancer in a warm blooded animal such as man.

According to a further aspect of the invention there is provided a method for the prevention or treatment of cancer in a warm blooded animal, such as man, in need of such treatment which comprises administering to said animal an effective amount of a compound of the Formula (I), or a pharmaceutically-acceptable salt thereof, as defined hereinbefore.

According to a further aspect of the invention, there is provided a compound of the Formula (I), or a pharmaceutically-acceptable salt thereof, as defined hereinbefore for use in the prevention or treatment of solid tumour disease in a warm blooded animal such as man.

According to a further aspect of the invention there is provided the use of a compound of the Formula (I), or a pharmaceutically-acceptable salt thereof, as defined hereinbefore in the manufacture of a medicament for use in the prevention or treatment of solid tumour disease in a warm blooded animal such as man.

According to a further aspect of the invention there is provided a method for the prevention or treatment of solid tumour disease in a warm blooded animal, such as man, in need of such treatment which comprises administering to said animal an effective amount of a compound of the Formula (I), or a pharmaceutically-acceptable salt thereof, as defined hereinbefore.

According to a further aspect of the invention there is provided a compound of the Formula (I), or a pharmaceutically-acceptable salt thereof, as defined hereinbefore for use in the prevention or treatment of those tumours which are sensitive to inhibition of ERα that are involved in the signal transduction steps which lead to the proliferation, survival, invasiveness and migratory ability of tumour cells.

According to a further aspect of the invention there is provided the use of a compound of the Formula (I), or a pharmaceutically-acceptable salt thereof, as defined hereinbefore in the manufacture of a medicament for use in the prevention or treatment of those tumours which are sensitive to inhibition of ERα that are involved in the signal transduction steps which lead to the proliferation, survival, invasiveness and migratory ability of tumour cells.

According to a further aspect of the invention there is provided a method for the prevention or treatment of those tumours which are sensitive to inhibition of ERα that are involved in the signal transduction steps which lead to the proliferation, survival, invasiveness and migratory ability of tumour cells which comprises administering to said animal an effective amount of a compound of the Formula (I), or a pharmaceutically-acceptable salt thereof, as defined hereinbefore.

According to a further aspect of the invention there is provided a compound of the Formula (I), or a pharmaceutically-acceptable salt thereof, as defined hereinbefore for use in providing an inhibitory effect on ERα.

According to a further aspect of the invention there is provided the use of a compound of the Formula (I), or a pharmaceutically-acceptable salt thereof, as defined hereinbefore in the manufacture of a medicament for use in providing an inhibitory effect on ERα.

According to a further aspect of the invention there is also provided a method for providing an inhibitory effect on ERα which comprises administering an effective amount of a compound of the Formula (I), or a pharmaceutically-acceptable salt thereof, as defined hereinbefore.

According to a further aspect of the invention there is provided a compound of the Formula (I), or a pharmaceutically-acceptable salt thereof, as defined hereinbefore for use in providing a selective inhibitory effect on ERα.

According to a further aspect of the invention there is provided the use of a compound of the Formula (I), or a pharmaceutically-acceptable salt thereof, as defined hereinbefore in the manufacture of a medicament for use in providing a selective inhibitory effect on ERα.

According to a further aspect of the invention there is also provided a method for providing a selective inhibitory effect on ERα which comprises administering an effective amount of a compound of the Formula (I), or a pharmaceutically-acceptable salt thereof, as defined hereinbefore.

Described herein are compounds that can bind to ERα ligand binding domain and are selective estrogen receptor degraders. In biochemical and cell based assays the compounds of the present invention are shown to be potent estrogen receptor binders and reduce cellular levels of ERα and may therefore be useful in the treatment of estrogen sensitive diseases or conditions (including diseases that have developed resistance to endocrine therapies), i.e. for use in the treatment of cancer of the breast and gynaecological cancers (including endometrial, ovarian and cervical) and cancers expressing ERα mutated proteins which may be de novo mutations or have arisen as a result of treatment with a prior endocrine therapy such as an aromatase inhibitor.

According to a further aspect of the invention there is provided a compound of the Formula (I), or a pharmaceutically-acceptable salt thereof, as defined herein before for use in the treatment of breast or gynaecological cancers.

According to a further aspect of the invention there is provided a compound of the Formula (I), or a pharmaceutically-acceptable salt thereof, as defined herein before for use in the treatment of cancer of the breast, endometrium, ovary or cervix.

According to a further aspect of the invention there is provided a compound of the Formula (I), or a pharmaceutically-acceptable salt thereof, as defined herein before for use in the treatment of cancer of the breast.

According to a further aspect of the invention there is provided a compound of the Formula (I), or a pharmaceutically-acceptable salt thereof, as defined herein before for use in the treatment of cancer of the breast, wherein the cancer has developed resistance to one or more other endocrine therapies.

According to a further aspect of the invention there is provided a method for treating breast or gynaecological cancers, which comprises administering an effective amount of a compound of the Formula (I), or a pharmaceutically-acceptable salt thereof, as defined hereinbefore.

According to a further aspect of the invention there is provided a method for treating cancer of the breast, endometrium, ovary or cervix, which comprises administering an effective amount of a compound of the Formula (I), or a pharmaceutically-acceptable salt thereof, as defined hereinbefore.

According to a further aspect of the invention there is provided a method for treating breast cancer, which comprises administering an effective amount of a compound of the Formula (I), or a pharmaceutically-acceptable salt thereof, as defined hereinbefore.

According to a further aspect of the invention there is provided a method for treating breast cancer, wherein the cancer has developed resistance to one or more other endocrine therapies, which comprises administering an effective amount of a compound of the Formula (I), or a pharmaceutically-acceptable salt thereof, as defined hereinbefore.

According to a further aspect of the invention there is provided the use of a compound of the Formula (I), or a pharmaceutically-acceptable salt thereof, as defined herein before in the manufacture of a medicament for use in the treatment of breast or gynaecological cancers.

According to a further aspect of the invention there is provided the use of a compound of the Formula (I), or a pharmaceutically-acceptable salt thereof, as defined herein before in the manufacture of a medicament for use in the treatment of cancer of the breast, endometrium, ovary or cervix.

According to a further aspect of the invention there is provided the use of a compound of the Formula (I), or a pharmaceutically-acceptable salt thereof, as defined herein before in the manufacture of a medicament for use in the treatment of breast cancer.

According to a further aspect of the invention there is provided the use of a compound of the Formula (I), or a pharmaceutically-acceptable salt thereof, as defined herein before in the manufacture of a medicament for use in the treatment of breast cancer, wherein the cancer has developed resistance to one or more other endocrine therapies.

In one feature of the invention, the cancer to be treated is breast cancer. In a further aspect of this feature, the breast cancer is Estrogen Receptor+ve (ER+ve). In one embodiment of this aspect, the compound of Formula (I) is dosed in combination with another anticancer agent, such as an anti-hormonal agent as defined herein.

According to a further aspect of the invention there is provided a compound of the Formula (I), or a pharmaceutically-acceptable salt thereof, as defined herein before for use in the treatment of ER+ve breast cancer.

According to a further aspect of the invention there is provided a method for treating ER+ve breast cancer, which comprises administering an effective amount of a compound of the Formula (I), or a pharmaceutically-acceptable salt thereof, as defined hereinbefore.

According to a further aspect of the invention there is provided the use of a compound of the Formula (I), or a pharmaceutically-acceptable salt thereof, as defined herein before in the manufacture of a medicament for use in the treatment of ER+ve breast cancer.

As stated hereinbefore, the in vivo effects of a compound of the Formula (I) may be exerted in part by one or more metabolites that are formed within the human or animal body after administration of a compound of the Formula (I).

The present invention therefore also contemplates a method for inhibiting ER-α in a patient, comprising administering to a patient an amount of a compound of Formula (I), or a pharmaceutically-acceptable salt thereof, effective in inhibiting ER-α in the patient.

The present invention therefore also contemplates a method for inhibiting ER-α in a patient, comprising administering to a patient an amount of a compound of Formula (I), or a pharmaceutically-acceptable salt thereof, effective in inhibiting ER-α in the patient.

In all of the above uses and methods, a suitable compound of the formula (I) is Example 1, or a pharmaceutically-acceptable salt thereof. In one aspect, Example 1 is in crystalline form B as described herein.

The anti-cancer treatment defined herein may be applied as a sole therapy or may involve, in addition to the compounds of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) antihormonal agents such as antioestrogens (for example tamoxifen, fulvestrant, toremifene, raloxifene, droloxifene and iodoxyfene), progestogens (for example megestrol acetate), aromatase inhibitors (for example as anastrozole, letrozole, vorazole and exemestane);
(iii) inhibitors of growth factor function and their downstream signalling pathways: included are Ab modulators of any growth factor or growth factor receptor targets, reviewed by Stem et al. *Critical Reviews in Oncology/Haematology*, 2005, 54, pp 11-29); also included are small molecule inhibitors of such targets, for example kinase inhibitors—examples include the anti-erbB2 antibody trastuzumab [Herceptin™], the anti-EGFR antibody panitumumab, the anti-EGFR antibody cetuximab [Erbitux, C225] and tyrosine kinase inhibitors including inhibitors of the erbB receptor family, such as epidermal growth factor family receptor (EGFR/erbB1) tyrosine kinase inhibitors such as gefitinib or erlotinib, erbB2 tyrosine kinase inhibitors such as lapatinib, and mixed erb1/2 inhibitors such as afatanib; similar strategies are available for other classes of growth factors and their receptors, for example inhibitors of the hepatocyte growth factor family or their receptors including c-met and ron; inhibitors of the insulin and insulin growth factor family or their receptors (IGFR, IR) inhibitors of the platelet-derived growth factor family or their receptors (PDGFR), and inhibitors of signalling mediated by other receptor tyrosine kinases such as c-kit, AnLK, and CSF-1R;
also included are modulators which target signalling proteins in the PI3-kinase signalling pathway, for example, inhibitors of PI3-kinase isoforms such as PI3K-α/β/γ and ser/thr kinases such as AKT, mTOR (such as AZD2014), PDK, SGK, PI4K or PIP5K; also included are inhibitors of serine/threonine kinases not listed above, for example raf inhibitors such as vemurafenib, MEK inhibitors such as selumetinib (AZD6244), Abl inhibitors such as imatinib or nilotinib, Btk inhibitors such as ibrutinib, Syk inhibitors such as fostamatinib, aurora kinase inhibitors (for example AZD1152), inhibitors of other ser/thr kinases such as JAKs, STATs and IRAK4, and cyclin dependent kinase inhibitors such as palbociclib; iv) modulators of DNA damage signalling pathways, for example PARP inhibitors (e.g. Olaparib), ATR inhibitors or ATM inhibitors; v) modulators of apoptotic and cell death pathways such as Bcl family modulators (e.g. ABT-263/Navitoclax, ABT-199);
(vi) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as sorafenib, axitinib, pazopanib, sunitinib and vandetanib (and compounds that work by other mechanisms (for example linomide, inhibitors of integrin αvβ3 function and angiostatin)];
(vii) vascular damaging agents, such as Combretastatin A4;
(viii) anti-invasion agents, for example c-Src kinase family inhibitors like (dasatinib, *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];
(ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies. Specific examples include monoclonal antibodies targeting PD-1 (e.g. BMS-936558) or CTLA4 (e.g. ipilimumab and tremelimumab);
(x) Antisense or RNAi based therapies, for example those which are directed to the targets listed.
(xi) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy.

According to this aspect of the invention there is provided a combination suitable for use in the treatment of cancer comprising compounds of the present invention as defined herein or a pharmaceutically acceptable salt thereof and another anti-tumour agent, in particular any one of the anti tumour agents listed under (i)-(xi) above. In particular, the anti-tumour agent listed under (i)-(xi) above is the standard of care for the specific cancer to be treated; the person skilled in the art will understand the meaning of "standard of care". In one aspect, the compound of the present invention is Example 1, or a pharmaceutically-acceptable salt thereof.

Therefore in a further aspect of the invention there is provided compounds of the present invention or a pharmaceutically acceptable salt thereof in combination with another anti-tumour agent, in particular an anti-tumour agent selected from one listed under (i)-(xi) herein above.

In a further aspect of the invention there is provided Example 1 [(E)-3-(3,5-Difluoro-4-((1R,3R)-2-(2-fluoro-2-methylpropyl)-3-methyl-2,3,4,9-tetrahydro-1H-pyrido[3,4-b]indol-1-yl)phenyl)acrylic acid] or a pharmaceutically acceptable salt thereof in combination with another anti-tumour agent, in particular an anti-tumour agent selected from one listed under (i)-(xi) herein above.

In a further aspect of the invention there is provided compounds of the present invention or a pharmaceutically acceptable salt thereof in combination with another anti-tumour agent, in particular an anti-tumour agent selected from one listed under (i) above.

In a further aspect of the invention there is provided a compound of the present invention as defined herein before or a pharmaceutically acceptable salt thereof and any one of the anti tumour agents listed under (i) above.

In a further aspect of the invention there is provided Example 1 or a pharmaceutically acceptable salt thereof in combination with any one of the anti-tumour agents listed under (i) above.

In a further aspect of the invention there is provided a combination suitable for use in the treatment of cancer comprising compounds of the present invention as defined hereinbefore or a pharmaceutically acceptable salt thereof and a taxoid, such as for example taxol or taxotere, conveniently taxotere. For example, a suitable compound of the invention in combination with a taxoid, such as for example taxol or taxotere, conveniently taxotere, is Example 1, or a pharmaceutically-acceptable salt thereof.

In a further aspect of the invention there is provided compounds of the present invention or a pharmaceutically acceptable salt thereof in combination with another anti-tumour agent, in particular an anti-tumour agent selected from one listed under (ii) herein above.

In a further aspect of the invention there is provided a combination suitable for use in the treatment of cancer comprising compounds of the present invention as defined herein before or a pharmaceutically acceptable salt thereof and any one of antihormonal agents listed under (ii) above, for example any one of the anti-oestrogens listed in (ii) above, or for example an aromatase inhibitor listed in (ii) above.

In a further aspect of the invention there is provided a combination suitable for use in the treatment of cancer comprising Example 1 or a pharmaceutically acceptable salt thereof and any one of antihormonal agents listed under (ii) above, for example any one of the anti-oestrogens listed in (ii) above, or for example an aromatase inhibitor listed in (ii) above.

In a further aspect of the invention there is provided a combination suitable for use in the treatment of cancer comprising Example 1 or a pharmaceutically acceptable salt thereof and an mTOR inhibitor, such as AZD2014 (see for example WO2008/023161).

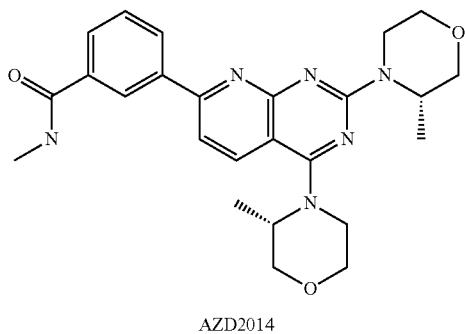 [SMILES: CNC(=O)c1cccc(-c2ccc3c(N4CCOC[C@@H]4C)nc(N4CCOC[C@@H]4C)nc3n2)c1]

AZD2014

In a further aspect of the invention there is provided a combination suitable for use in the treatment of cancer comprising Example 1, or a pharmaceutically-acceptable salt thereof and a PI3Kα-inhibitor, such as those PI3K α/δ inhibitors in our co-pending PCT application PCT/GB2014/050163. One example of a suitable PI3K α/δ inhibitor is Example 3 from PCT/GB2014/050163, which is the compound 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one, or a pharmaceutically-acceptable salt thereof. A process to make Example 3 of PCT/GB2014/050163 is set out in Reference Example 1 herein.

In a further aspect of the invention there is provided a combination suitable for use in the treatment of cancer comprising Example 1 or a pharmaceutically acceptable salt thereof and palbociclib.

In one aspect the above combination of a compound of formula (I) or a pharmaceutically acceptable salt thereof, particularly Example 1 or a pharmaceutically acceptable salt thereof, with an anti-tumour agent listed in (ii) above, or an mTOR inhibitor (such as AZD2014), or a PI3K-α inhibitor (such as those PI3K α/δ inhibitors in our co-pending PCT application PCT/GB2014/050163, particularly Example 3 therein) or palbociclib, is suitable for use in the treatment of breast or gynaecological cancers, such as cancer of the breast, endometrium, ovary or cervix, particularly breast cancer, such as ER+ve breast cancer.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination. Where a combination of two or more components is administered separately or sequential, it will be understood that the dosage regime for each component may be different to and independent of the other components. Conveniently, the compounds of the present invention are dosed once daily.

According to a further aspect of the invention there is provided a pharmaceutical composition which comprises a compound of Formula (I) or a pharmaceutically acceptable salt thereof in combination with an anti-tumour agent selected from one listed under (i)-(xi) herein above, in association with a pharmaceutically acceptable diluent or carrier.

According to a further aspect of the invention there is provided a pharmaceutical composition which comprises Example 1 [(E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid] or a pharmaceutically acceptable salt thereof in combination with an anti-tumour agent selected from one listed under (i)-(xi) herein above, in association with a pharmaceutically acceptable diluent or carrier.

According to a further aspect of the invention there is provided a pharmaceutical composition which comprises a compound of Formula (I) or a pharmaceutically acceptable salt thereof in combination with any one of antihormonal agents listed under (ii) above, for example any one of the anti-oestrogens listed in (ii) above, or for example an aromatase inhibitor listed in (ii) above in association with a pharmaceutically acceptable diluent or carrier.

In a further aspect of the invention there is provided a pharmaceutical composition which comprises Example 1 or a pharmaceutically acceptable salt thereof and any one of antihormonal agents listed under (ii) above, for example any one of the anti-oestrogens listed in (ii) above, or for example an aromatase inhibitor listed in (ii) above; in association with a pharmaceutically acceptable diluent or carrier.

In a further aspect of the invention there is provided a pharmaceutical composition comprising Example 1 or a pharmaceutically acceptable salt thereof and an mTOR inhibitor, such as AZD2014 (see for example WO2008/023161); in association with a pharmaceutically acceptable diluent or carrier.

In a further aspect of the invention there is provided a pharmaceutical composition comprising Example 1, or a pharmaceutically-acceptable salt thereof and a PI3Kα-inhibitor, such as those PI3K α/δ inhibitors in our co-pending PCT application PCT/GB2014/050163, in association with a pharmaceutically acceptable diluent or carrier. One example of a suitable PI3K α/δ inhibitor is Example 3 from PCT/GB2014/050163, as described hereinbefore.

In a further aspect of the invention there is provided a pharmaceutical composition comprising Example 1 or a pharmaceutically acceptable salt thereof and palbociclib in association with a pharmaceutically acceptable diluent or carrier.

In one aspect the above pharmaceutical compositions of a compound of formula (I) or a pharmaceutically acceptable salt thereof, particularly Example 1 or a pharmaceutically acceptable salt thereof, with an anti-tumour agent listed in (ii) above, or an mTOR inhibitor (such as AZD2014), or a PI3K-α inhibitor (such as those PI3K α/δ inhibitors in our co-pending PCT application PCT/GB2014/050163, particularly Example 3 therein) or palbociclib, is suitable for use in the treatment of breast or gynaecological cancers, such as cancer of the breast, endometrium, ovary or cervix, particularly breast cancer, such as ER+ve breast cancer.

According to a further aspect of the invention there is provided a pharmaceutical composition which comprises a compound of Formula (I) or a pharmaceutically acceptable salt thereof in combination with an anti-tumour agent selected from one listed under (i)-(xi) herein above, in association with a pharmaceutically acceptable diluent or carrier for use in treating cancer.

According to a further aspect of the invention there is provided a pharmaceutical composition which comprises a compound of Formula (I) or a pharmaceutically acceptable salt thereof in combination with any one of antihormonal agents listed under (ii) above, for example any one of the anti-oestrogens listed in (ii) above, or for example an aromatase inhibitor listed in (ii) above in association with a pharmaceutically acceptable diluent or carrier for use in treating cancer.

According to a further aspect of the invention there is provided a pharmaceutical composition which comprises Example 1 or a pharmaceutically acceptable salt thereof in combination with an anti-tumour agent selected from one listed under (i)-(xi) herein above, in association with a pharmaceutically acceptable diluent or carrier for use in treating cancer.

In a further aspect of the invention there is provided a pharmaceutical composition which comprises Example 1 or a pharmaceutically acceptable salt thereof and any one of antihormonal agents listed under (ii) above, for example any one of the anti-oestrogens listed in (ii) above, or for example an aromatase inhibitor listed in (ii) above; in association with a pharmaceutically acceptable diluent or carrier for use in treating cancer.

In a further aspect of the invention there is provided a pharmaceutical composition comprising Example 1 or a pharmaceutically acceptable salt thereof and an mTOR inhibitor, such as AZD2014 (see for example WO2008/023161); in association with a pharmaceutically acceptable diluent or carrier for use in treating cancer.

In a further aspect of the invention there is provided a pharmaceutical composition comprising Example 1, or a pharmaceutically-acceptable salt thereof and a PI3Kα-inhibitor, such as those PI3K α/δ inhibitors in our co-pending PCT application PCT/GB2014/050163, in association with a pharmaceutically acceptable diluent or carrier for use in treating cancer. One example of a suitable PI3K α/δ inhibitor is Example 3 from PCT/GB2014/050163, as described hereinbefore.

In a further aspect of the invention there is provided a pharmaceutical composition comprising Example 1 or a pharmaceutically acceptable salt thereof and palbociclib in association with a pharmaceutically acceptable diluent or carrier for use in treating cancer.

In one aspect the above pharmaceutical compositions of a compound of formula (I) or a pharmaceutically acceptable salt thereof, particularly Example 1 or a pharmaceutically acceptable salt thereof, with an anti-tumour agent listed in (ii) above, or an mTOR inhibitor (such as AZD2014), or a PI3K-α inhibitor (such as those PI3K α/δ inhibitors in our co-pending PCT application PCT/GB2014/050163, particularly Example 3 therein) or palbociclib, is suitable for use in the treatment of breast or gynaecological cancers, such as cancer of the breast, endometrium, ovary or cervix, particularly breast cancer, such as ER+ve breast cancer.

According to another feature of the invention there is provided the use of a compound of the Formula (I) or a pharmaceutically acceptable salt thereof in combination with an anti-tumour agent selected from one listed under (i)-(xi) herein above, in the manufacture of a medicament for use in the treatment of cancer in a warm-blooded animal, such as man.

According to another feature of the invention there is provided the use of Example 1 or a pharmaceutically acceptable salt thereof in combination with an anti-tumour agent selected from one listed under (i)-(xi) herein above, in the manufacture of a medicament for use in cancer in a warm-blooded animal, such as man.

According to a further aspect of the invention there is provided the use of a compound of Formula (I) or a pharmaceutically acceptable salt thereof in combination with any one of antihormonal agents listed under (ii) above, for example any one of the anti-oestrogens listed in (ii) above, or for example an aromatase inhibitor listed in (ii) above in the manufacture of a medicament for use in the treatment of cancer in a warm-blooded animal, such as man.

In a further aspect of the invention there is provided the use of Example 1 or a pharmaceutically acceptable salt thereof in combination with any one of antihormonal agents listed under (ii) above, for example any one of the anti-oestrogens listed in (ii) above, or for example an aromatase inhibitor listed in (ii) above; in the manufacture of a medicament for use in the treatment of cancer in a warm-blooded animal, such as man.

In a further aspect of the invention there is provided the use of Example 1 or a pharmaceutically acceptable salt thereof in combination with an mTOR inhibitor, such as AZD2014 (see for example WO2008/023161); in the manufacture of a medicament for use in the treatment of cancer in a warm-blooded animal, such as man.

In a further aspect of the invention there is provided the use of Example 1, or a pharmaceutically-acceptable salt thereof in combination with a PI3Kα-inhibitor, such as those PI3K α/δ inhibitors in our co-pending PCT application PCT/GB2014/050163, in the manufacture of a medicament for use in the treatment of cancer in a warm-blooded animal, such as man. One example of a suitable PI3K α/δ inhibitor is Example 3 from PCT/GB2014/050163, as described hereinbefore.

In a further aspect of the invention there is provided the use of Example 1 or a pharmaceutically acceptable salt thereof in combination with palbociclib in the manufacture of a medicament for use in the treatment of cancer in a warm-blooded animal, such as man.

In one aspect the above uses of a compound of formula (I) or a pharmaceutically acceptable salt thereof, particularly Example 1 or a pharmaceutically acceptable salt thereof, in combination with an anti-tumour agent listed in (ii) above, or an mTOR inhibitor (such as AZD2014), or a PI3K-α inhibitor (such as those PI3K α/δ inhibitors in our co-pending PCT application PCT/GB2014/050163, particularly Example 3 therein) or palbociclib, is suitable for use in the manufacture of a medicament for the treatment of breast or gynaecological cancers, such as cancer of the breast, endometrium, ovary or cervix, particularly breast cancer, such as ER+ve breast cancer.

Therefore in an additional feature of the invention, there is provided a method of treating cancer in a warm-blooded animal, such as man, in need of such treatment which comprises administering to said animal an effective amount of a compound of Formula (I) or a pharmaceutically acceptable salt thereof in combination with an anti-tumour agent selected from one listed under (i)-(xi) herein above.

According to a further aspect of the invention, there is provided a method of treating cancer in a warm-blooded animal, such as man, in need of such treatment which comprises administering to said animal an effective amount of Example 1 or a pharmaceutically acceptable salt thereof in combination with an anti-tumour agent selected from one listed under (i)-(xi) herein above.

According to a further aspect of the invention there is provided a method of treating cancer in a warm-blooded animal, such as man, in need of such treatment which comprises administering to said animal an effective amount of a compound of Formula (I) or a pharmaceutically acceptable salt thereof in combination with any one of antihormonal agents listed under (ii) above, for example any one of the anti-oestrogens listed in (ii) above, or for example an aromatase inhibitor listed in (ii) above.

In a further aspect of the invention there is provided a method of treating cancer in a warm-blooded animal, such as man, in need of such treatment which comprises administering to said animal an effective amount of Example 1 or a pharmaceutically acceptable salt thereof in combination with any one of antihormonal agents listed under (ii) above, for example any one of the anti-oestrogens listed in (ii) above, or for example an aromatase inhibitor listed in (ii) above.

In a further aspect of the invention there is provided a method of treating cancer in a warm-blooded animal, such as man, in need of such treatment which comprises administering to said animal an effective amount of Example 1 or a pharmaceutically acceptable salt thereof in combination with an mTOR inhibitor, such as AZD2014 (see for example WO2008/023161).

In a further aspect of the invention there provided a method of treating cancer in a warm-blooded animal, such as man, in need of such treatment which comprises administering to said animal an effective amount of Example 1, or a pharmaceutically-acceptable salt thereof in combination with a PI3Kα-inhibitor, such as those PI3K α/δ inhibitors in our co-pending PCT application PCT/GB2014/050163. One example of a suitable PI3K α/δ inhibitor is Example 3 from PCT/GB2014/050163, as described hereinbefore.

In a further aspect of the invention there is provided a method of treating cancer in a warm-blooded animal, such as man, in need of such treatment which comprises administering to said animal an effective amount of Example 1 or a pharmaceutically acceptable salt thereof in combination with palbociclib.

In one aspect the above methods of treating cancer, are methods for the treatment of breast or gynaecological cancers, such as cancer of the breast, endometrium, ovary or cervix, particularly breast cancer, such as ER+ve breast cancer.

According to a further aspect of the present invention there is provided a kit comprising a compound of Formula (I) or a pharmaceutically acceptable salt thereof in combination with an anti-tumour agent selected from one listed under (i)-(xi) herein above.

According to a further aspect of the present invention there is provided a kit comprising a compound of Formula (I) or a pharmaceutically acceptable salt thereof in combination with an anti-tumour agent selected from one listed under (i) or (ii) herein above.

According to a further aspect of the present invention there is provided a kit comprising:
a) a compound of Formula (I) or a pharmaceutically acceptable salt thereof in a first unit dosage form;
b) an anti-tumour agent selected from one listed under (i)-(xi) herein above in a second unit dosage form; and
c) container means for containing said first and second dosage forms.

According to a further aspect of the present invention there is provided a kit comprising:
a) a compound of Formula (I) or a pharmaceutically acceptable salt thereof in a first unit dosage form;
b) an anti-tumour agent selected from one listed under (i)-(ii) herein above in a second unit dosage form; and
c) container means for containing said first and second dosage forms.

According to a further aspect of the present invention there is provided a kit comprising Example 1 or a pharmaceutically acceptable salt thereof in combination with an anti-tumour agent selected from one listed under (i)-(xi) herein above.

According to a further aspect of the present invention there is provided a kit comprising Example 1 or a pharmaceutically acceptable salt thereof in combination with an anti-tumour agent selected from one listed under (i) or (ii) herein above.

According to a further aspect of the present invention there is provided a kit comprising:
a) Example 1 or a pharmaceutically acceptable salt thereof in a first unit dosage form;
b) an anti-tumour agent selected from one listed under (i)-(xi) herein above in a second unit dosage form; and
c) container means for containing said first and second dosage forms.

According to a further aspect of the present invention there is provided a kit comprising:
a) Example 1 or a pharmaceutically acceptable salt thereof in a first unit dosage form;
b) an anti-tumour agent selected from one listed under (i)-(ii) herein above in a second unit dosage form; and
c) container means for containing said first and second dosage forms.

According to a further aspect of the present invention there is provided a kit comprising:
a) Example 1 or a pharmaceutically acceptable salt thereof in a first unit dosage form;
b) an anti-tumour agent selected from AZD2014, a PI3Kα-inhibitor (such as those PI3K α/δ inhibitors in our co-pending PCT application PCT/GB2014/050163) and palbociclib in a second unit dosage form; and
c) container means for containing said first and second dosage forms.

In all of the above methods, uses and other aspects, where the compound of Example 1 is used, it is suitably used as crystalline Form B.

Combination therapy as described above may be added on top of standard of care therapy typically carried out according to its usual prescribing schedule.

Although the compounds of the Formula (I) are primarily of value as therapeutic agents for use in warm-blooded animals (including man), they are also useful whenever it is required to inhibit ER-α. Thus, they are useful as pharmacological standards for use in the development of new biological tests and in the search for new pharmacological agents.

Personalised Healthcare

Another aspect of the present invention is based on identifying a link between the status of the gene encoding ERα and potential susceptibility to treatment with a compound of Formula (I). In particular, ERα gene status may indicate that a patient is less likely to respond to existing hormone therapy (such as aromatase inhibitors), in part at least because some ERα mutations are though to arise as resistance mechanisms to existing treatments. A SERD, particularly a SERD which can be administered orally in potentially larger doses without excessive inconvenience, may then advantageously be used to treat patients with ERα mutations who may be resistant to other therapies. This therefore provides opportunities, methods and tools for selecting patients for treatment with a compound of Formula (I), particularly cancer patients. The present invention relates to patient selection tools and methods (including personalised medicine). The selection is based on whether the tumour cells to be treated possess wild-type or mutant ERα gene. The ERα gene status could therefore be used as a biomarker to indicate that selecting treatment with a SERD may be advantageous. For the avoidance of doubt, compounds of the formula (I) as described herein are thought to be similarly active against wild-type and mutant ERα genes, at least those mutations in ERα gene identified at the date of filing this application.

There is a clear need for biomarkers that will enrich for or select patients whose tumours will respond to treatment with a SERD, such as a compound of Formula (I). Patient selection biomarkers that identify the patients most likely to respond to one agent over another are ideal in the treatment of cancer, since they reduce the unnecessary treatment of patients with non-responding tumours to the potential side effects of such agents.

A biomarker can be described as "a characteristic that is objectively measured and evaluated as an indicator of normal biologic processes, pathogenic processes, or pharmacologic responses to a therapeutic intervention". A biomarker is any identifiable and measurable indicator associated with a particular condition or disease where there is a correlation between the presence or level of the biomarker and some aspect of the condition or disease (including the presence of, the level or changing level of, the type of, the stage of, the susceptibility to the condition or disease, or the responsiveness to a drug used for treating the condition or disease). The correlation may be qualitative, quantitative, or both qualitative and quantitative. Typically a biomarker is a compound, compound fragment or group of compounds. Such compounds may be any compounds found in or produced by an organism, including proteins (and peptides), nucleic acids and other compounds.

Biomarkers may have a predictive power, and as such may be used to predict or detect the presence, level, type or stage of particular conditions or diseases (including the presence or level of particular microorganisms or toxins), the susceptibility (including genetic susceptibility) to particular conditions or diseases, or the response to particular treatments (including drug treatments). It is thought that biomarkers will play an increasingly important role in the future of drug discovery and development, by improving the efficiency of research and development programs. Biomarkers can be used as diagnostic agents, monitors of disease progression, monitors of treatment and predictors of clinical outcome. For example, various biomarker research projects are attempting to identify markers of specific cancers and of specific cardiovascular and immunological diseases. It is believed that the development of new validated biomarkers will lead both to significant reductions in healthcare and drug development costs and to significant improvements in treatment for a wide variety of diseases and conditions.

In order to optimally design clinical trials and to gain the most information from these trials, a biomarker may be required. The marker may be measurable in surrogate and tumour tissues. Ideally these markers will also correlate with efficacy and thus could ultimately be used for patient selection.

Thus, the technical problem underlying this aspect of the present invention is the identification of means for stratification of patients for treatment with a compound of Formula (I). The technical problem is solved by provision of the embodiments characterized in the claims and/or description herein.

Tumours which contain wild type ERα are believed to be susceptible to treatment with a compound of formula (I), for example as a first-line treatment. Tumours may also respond to treatment with a compound of formula (I) as a second-line, third-line or subsequent therapy and this may be useful, in particular, where the tumours contain mutant ERα and may thus be resistant to existing therapies such as AIs. A higher dosage of a compound of formula (I) may be required in the resistant setting than in wild type tumours).

The invention provides a method of determining sensitivity of cells to a compound of Formula (I). The method comprises determining the status of ERα gene in said cells. A cell is defined as sensitive to a compound of Formula (I) if it inhibits the increase in cell number in a cell growth assay (either through inhibition of cell proliferation and/or through increased cell death). Methods of the invention are useful for predicting which cells are more likely to respond to a compound of Formula (I) by growth inhibition.

A sample "representative of the tumour" can be the actual tumour sample isolated, or may be a sample that has been further processed, e.g. a sample of PCR amplified nucleic acid from the tumour sample.

Definitions:

In this Personalised Healthcare section:

"Allele" refers to a particular form of a genetic locus, distinguished from other forms by its particular nucleotide or amino acid sequence.

"Amplification reactions" are nucleic acid reactions which result in specific amplification of target nucleic acids over non-target nucleic acids. The polymerase chain reaction (PCR) is a well known amplification reaction.

"Cancer" is used herein to refer to neoplastic growth arising from cellular transformation to a neoplastic phenotype. Such cellular transformation often involves genetic mutation.

"Gene" is a segment of DNA that contains all the information for the regulated biosynthesis of an RNA product, including a promoter, exons, introns, and other sequence elements which may be located within 5' or 3' flanking regions (not within the transcribed portions of the gene) that control expression.

"Gene status" refers to whether the gene is wild type or not (i.e. mutant).

"Label" refers to a composition capable of producing a detectable signal indicative of the presence of the target polynucleotide in an assay sample. Suitable labels include radioisotopes, nucleotide chromophores, enzymes, substrates, fluorescent molecules, chemiluminescent moieties, magnetic particles, bioluminescent moieties, and the like. As such, a label is any composition detectable by spectroscopic, photochemical, biochemical, immunochemical, electrical, optical or chemical means.

"Non-synonymous variation" refers to a variation (variance) in or overlapping the coding sequence of a gene that result in the production of a distinct (altered) polypeptide sequence. These variations may or may not affect protein function and include missense variants (resulting in substitution of one amino acid for another), nonsense variants (resulting in a truncated polypeptide due to generation of a premature stop codon) and insertion/deletion variants.

"Synonymous variation" refers to a variation (variance) in the coding sequence of a gene that does not affect sequence of the encoded polypeptide. These variations may affect protein function indirectly (for example by altering expression of the gene), but, in the absence of evidence to the contrary, are generally assumed to be innocuous.

"Nucleic acid" refers to single stranded or double stranded DNA and RNA molecules including natural nucleic acids found in nature and/or modified, artificial nucleic acids having modified backbones or bases, as are known in the art.

"Primer" refers to a single stranded DNA oligonucleotide sequence capable of acting as a point of initiation for synthesis of a primer extension product which is complementary to the nucleic acid strand to be copied. The length and sequence of the primer must be such that they are able to prime the synthesis of extension products. A typical primer contains at least about 7 nucleotides in length of a sequence substantially complementary to the target sequence, but somewhat longer primers are preferred. Usually primers contain about 15-26 nucleotides, but longer or shorter primers may also be employed.

"Polymorphic site" is a position within a locus at which at least two alternative sequences are found in a population.

"Polymorphism" refers to the sequence variation observed in an individual at a polymorphic site. Polymorphisms include nucleotide substitutions, insertions, deletions and microsatellites and may, but need not, result in detectable differences in gene expression or protein function. In the absence of evidence of an effect on expression or protein function, common polymorphisms, including non-synonomous variants, are generally considered to be included in the definition of wild-type gene sequence. A catalog of human polymorphisms and associated annotation, including validation, observed frequencies, and disease association, is maintained by NCBI (dbSNP: http://www.ncbi.nlm.nih.gov/projects/SNP/). Please note that the term "polymorphism" when used in the context of gene sequences should not be confused with the term "polymorphism" when used in the context of solid state form of a compound, that is the crystalline or amorphous nature of a compound. The skilled person will understand the intended meaning by its context.

"Probe" refers to single stranded sequence-specific oligonucleotides which have a sequence that is exactly complementary to the target sequence of the allele to be detected.

"Response" is defined by measurements taken according to Response Evaluation Criteria in Solid Tumours (RECIST) involving the classification of patients into two main groups: those that show a partial response or stable disease and those that show signs of progressive disease.

"Stringent hybridisation conditions" refers to an overnight incubation at 42° C. in a solution comprising 50% formamide, 5×SSC (750 mM NaCl, 75 mM trisodium citrate), 50 mM sodium phosphate (pH 7.6), 5×Denhardt's solution, 10% dextran sulphate, and 20 pg/ml denatured, sheared salmon sperm DNA, followed by washing the filters in 0.1×SSC at about 65° C.

"Survival" encompasses a patients' overall survival and progression-free survival.

"Overall survival" (OS) is defined as the time from the initiation of drug administration to death from any cause. "Progression-free survival" (PFS) is defined as the time from the initiation of drug administration to first appearance of progressive disease or death from any cause.

According to one aspect of the invention there is provided a method for selecting a patient for treatment with a compound of Formula (I), the method comprising providing a tumour cell containing sample from a patient; determining whether the ERα gene in the patient's tumour cell containing sample is wild type or mutant; and selecting a patient for treatment with a compound of Formula (I) based thereon.

The method may include or exclude the actual patient sample isolation step. Thus, according to one aspect of the invention there is provided a method for selecting a patient for treatment with a compound of Formula (I), the method comprising determining whether the ERα gene in a tumour cell containing sample previously isolated from the patient is wild type or mutant; and selecting a patient for treatment with a compound of Formula (I) based thereon.

In one embodiment, the patient is selected for treatment with a compound of Formula (I) if the tumour cell DNA has a mutant ERα gene. In other embodiments, a patient whose tumour cell DNA possesses a wild type ERα gene is selected for treatment with a compound of Formula (I).

For the purpose of this invention, a gene status of wild-type is meant to indicate normal or appropriate expression of the gene and normal function of the encoded protein.

In contrast, mutant status is meant to indicate expression of a protein with altered function, consistent with the known roles of mutant ERα genes in cancer (as described herein). Any number of genetic or epigenetic alterations, including but not limited to mutation, amplification, deletion, genomic rearrangement, or changes in methylation profile, may result in a mutant status. However, if such alterations nevertheless result in appropriate expression of the normal protein, or a functionally equivalent variant, then the gene status is regarded as wild-type. Examples of variants that typically would not result in a functional mutant gene status include synonomous coding variants and common polymorphisms (synonymous or non-synonymous). As discussed below, gene status can be assessed by a functional assay, or it may be inferred from the nature of detected deviations from a reference sequence.

In certain embodiments the wild-type or mutant status of the ERα gene is determined by the presence or absence of non-synonymous nucleic acid variations in the genes. Observed non-synonymous variations corresponding to known common polymorphisms with no annotated functional effects do not contribute to a gene status of mutant.

Other variations in the ERα gene that signify mutant status include splice site variations that decrease recognition of an intron/exon junction during processing of pre-mRNA to mRNA. This can result in exon skipping or the inclusion of normally intronic sequence in spliced mRNA (intron retention or utilization of cryptic splice junctions). This can, in turn, result in the production of aberrant protein with insertions and/or deletions relative to the normal protein. Thus, in other embodiments, the gene has a mutant status if there is a variant that alters splice site recognition sequence at an intron/exon junction.

For ESR1, reference sequences are available for the gene (GenBank accession number: NG_008493), mRNA (GenBank accession number: NM_000125), and protein (GenBank accession number: NP_000116 or Swiss-Prot accession: P03372). A person of skill in the art will be able to determine the ESR1 gene status, i.e. whether a particular ESR1 gene is wild type or mutant, based on comparison of DNA or protein sequence with wild type.

It will be apparent that the gene and mRNA sequences disclosed for ERα gene are representative sequences. In normal individuals there are two copies of each gene, a maternal and paternal copy, which will likely have some sequence differences, moreover within a population there will exist numerous allelic variants of the gene sequence. Other sequences regarded as wild type include those that possess one or more synonymous changes to the nucleic acid sequence (which changes do not alter the encoded protein sequence), non-synonymous common polymorphisms (e.g. germ-line polymorphisms) which alter the protein sequence but do not affect protein function, and intronic non-splice-site sequence changes.

There are numerous techniques available to the person skilled in the art to determine the gene status of ERα. The gene status can be determined by determination of the nucleic acid sequence. This could be via direct sequencing of the full-length gene or analysis of specific sites within the gene, e.g. commonly mutated sites.

Samples

The patient's sample to be tested for the gene status can be any tumour tissue or tumour-cell containing sample obtained or obtainable from the individual. The test sample is conveniently a sample of blood, mouth swab, biopsy, or other body fluid or tissue obtained from an individual. Particular examples include: circulating tumour cells, circulating DNA in the plasma or serum, cells isolated from the ascites fluid of ovarian cancer patients, lung sputum for patients with tumours within the lung, a fine needle aspirate from a breast cancer patient, urine, peripheral blood, a cell scraping, a hair follicle, a skin punch or a buccal sample.

It will be appreciated that the test sample may equally be a nucleic acid sequence corresponding to the sequence in the test sample, that is to say that all or a part of the region in the sample nucleic acid may firstly be amplified using any convenient technique e.g. polymerase chain reaction (PCR), before analysis. The nucleic acid may be genomic DNA or fractionated or whole cell RNA. In particular embodiments the RNA is whole cell RNA and is used directly as the template for labelling a first strand cDNA using random primers or poly A primers. The nucleic acid or protein in the test sample may be extracted from the sample according to standard methodologies (see Green & Sambrook, Eds., Molecular Cloning: A Laboratory Manual, (2012, 4th edition, Vol. 1-3, ISBN 9781936113422), Cold Spring Harbor Laboratory Press, Cold Spring Harbor, N.Y.).

The diagnostic methods of the invention can be undertaken using a sample previously taken from the individual or patient. Such samples may be preserved by freezing or fixed and embedded in formalin-paraffin or other media. Alternatively, a fresh tumour cell containing sample may be obtained and used.

The methods of the invention can be applied using cells from any tumour. Suitable tumours for treatment with a compound of Formula (I) have been described hereinbefore.

Methods for Detection of Nucleic Acids

The detection of mutant ERα nucleic acids can be employed, in the context of the present invention, to select drug treatment. Since mutations in these genes occur at the DNA level, the methods of the invention can be based on detection of mutations or variances in genomic DNA, as well as transcripts and proteins themselves. It can be desirable to confirm mutations in genomic DNA by analysis of transcripts and/or polypeptides, in order to ensure that the detected mutation is indeed expressed in the subject.

It will be apparent to the person skilled in the art that there are a large number of analytical procedures which may be used to detect the presence or absence of variant nucleotides at one or more positions in a gene. In general, the detection of allelic variation requires a mutation discrimination technique, optionally an amplification reaction (such as one based on polymerase chain reaction) and optionally a signal generation system. There are a multitude of mutation detection techniques available in the art and these may be used in combination with a signal generation system, of which there are numerous available in the art. Many methods for the detection of allelic variation are reviewed by Nollau et al., *Clin. Chem.*, 1997, 43, 1114-1120; Anderson SM. *Expert Rev Mol Diagn.*, 2011, 11, 635-642; Meyerson M. et al., *Nat Rev Genet.*, 2010, 11, 685-696; and in standard textbooks, for example "*Laboratory Protocols for Mutation Detection*", Ed. by U. Landegren, Oxford University Press, 1996 and "PCR", $2^{nd}$ Edition by Newton & Graham, BIOS Scientific Publishers Limited, 1997.

As noted above, determining the presence or absence of a particular variance or plurality of variances in the ERα gene in a patient with cancer can be performed in a variety of ways. Such tests are commonly performed using DNA or RNA collected from biological samples, e.g., tissue biopsies, urine, stool, sputum, blood, cells, tissue scrapings, breast aspirates or other cellular materials, and can be performed by a variety of methods including, but not limited to, PCR, hybridization with allele-specific probes, enzymatic mutation detection, chemical cleavage of mismatches, mass spectrometry or DNA sequencing, including minisequencing.

Suitable mutation detection techniques include amplification refractory mutation system (ARMS™), amplification refractory mutation system linear extension (ALEX™), competitive oligonucleotide priming system (COPS), Taqman, Molecular Beacons, restriction fragment length polymorphism (RFLP), and restriction site based PCR and fluorescence resonance energy transfer (FRET) techniques.

In particular embodiments the method employed for determining the nucleotide(s) within a biomarker gene is selected from: allele-specific amplification (allele specific PCR)—such as amplification refractory mutation system (ARMS), sequencing, allelic discrimination assay, hybridisation, restriction fragment length polymorphism (RFLP) or oligonucleotide ligation assay (OLA).

In particular embodiments, hybridization with allele specific probes can be conducted by: (1) allele specific oligonucleotides bound to a solid phase (e.g. glass, silicon, nylon membranes) with the labelled sample in solution, for example as in many DNA chip applications; or, (2) bound sample (often cloned DNA or PCR amplified DNA) and labelled oligonucleotides in solution (either allele specific or short so as to allow sequencing by hybridization). Diagnostic tests may involve a panel of variances, often on a solid support, which enables the simultaneous determination of more than one variance. Such hybridization probes are well known in the art (see, e.g., Green & Sambrook, Eds., Molecular Cloning: A Laboratory Manual, (2012, 4th edition, Vol. 1-3, ISBN 9781936113422), Cold Spring Harbor Laboratory Press, Cold Spring Harbor, N.Y.) and may span two or more variance sites.

Thus, in one embodiment, the detection of the presence or absence of at least one mutation provides for contacting ERα nucleic acid containing a putative mutation site with at least one nucleic acid probe. The probe preferentially hybridizes with a nucleic acid sequence including a variance site and containing complementary nucleotide bases at the variance site under selective hybridization conditions.

Hybridization can be detected with a detectable label using labels known to one skilled in the art. Such labels include, but are not limited to radioactive, fluorescent, dye, and enzymatic labels.

In another embodiment, the detection of the presence or absence of at least one mutation provides for contacting ERα nucleic acid containing a putative mutation site with at least one nucleic acid primer. The primer preferentially hybridizes with a nucleic acid sequence including a variance site and containing complementary nucleotide bases at the variance site under selective hybridization conditions.

Oligonucleotides used as primers for specific amplification may carry the complementary nucleotide base to the mutation of interest in the centre of the molecule (so that amplification depends on differential hybridization; see, e.g., Gibbs, et al., 1989. *Nucl. Acids Res.*, 17, 2437-248) or at the extreme 3'-terminus of one primer where, under appropriate conditions, mismatch can prevent, or reduce polymerase extension (see, e.g., Prossner, 1993, *Tibtech*, 11 238).

In yet another embodiment, the detection of the presence or absence of at least one mutation comprises sequencing at least one nucleic acid sequence and comparing the obtained sequence with the known wild type nucleic acid sequence.

Alternatively, the presence or absence of at least one mutation comprises mass spectrometric determination of at least one nucleic acid sequence.

In one embodiment, the detection of the presence or absence of at least one nucleic acid variance comprises performing a polymerase chain reaction (PCR). The target nucleic acid sequence containing the hypothetical variance is amplified and the nucleotide sequence of the amplified nucleic acid is determined. Determining the nucleotide sequence of the amplified nucleic acid comprises sequencing at least one nucleic acid segment. Alternatively, amplification products can be analyzed using any method capable of separating the amplification products according to their size, including automated and manual gel electrophoresis, and the like.

Mutations in genomic nucleic acid are advantageously detected by techniques based on mobility shift in amplified nucleic acid fragments. For instance, Chen et al., *Anal Biochem* 1996, 239, 61-9, describe the detection of single-base mutations by a competitive mobility shift assay. Moreover, assays based on the technique of Marcelino et al., *BioTechniques* 1999, 26, 1134-1148 are available commercially.

In a particular example, capillary heteroduplex analysis may be used to detect the presence of mutations based on mobility shift of duplex nucleic acids in capillary systems as a result of the presence of mismatches.

Generation of nucleic acids for analysis from samples generally requires nucleic acid amplification. Many amplification methods rely on an enzymatic chain reaction (such as a polymerase chain reaction, a ligase chain reaction, or a self-sustained sequence replication) or from the replication of all or part of the vector into which it has been cloned. Preferably, the amplification according to the invention is an exponential amplification, as exhibited by for example the polymerase chain reaction.

Many target and signal amplification methods have been described in the literature, for example, general reviews of these methods in Landegren, U., et al., *Science*, 1988 242, 229-237 and Lewis, R., *Genetic Engineering News* 1990, 10, 54-55. These amplification methods can be used in the methods of our invention, and include polymerase chain reaction (PCR), PCR in situ, ligase amplification reaction (LAR), ligase hybridisation, Qβ bacteriophage replicase, transcription-based amplification system (TAS), genomic amplification with transcript sequencing (GAWTS), nucleic acid sequence-based amplification (NASBA) and in situ hybridisation. Primers suitable for use in various amplification techniques can be prepared according to methods known in the art.

Polymerase Chain Reaction (PCR) PCR is a nucleic acid amplification method described inter alia in U.S. Pat. Nos. 4,683,195 and 4,683,202. PCR consists of repeated cycles of DNA polymerase generated primer extension reactions. The target DNA is heat denatured and two oligonucleotides, which bracket the target sequence on opposite strands of the DNA to be amplified, are hybridised. These oligonucleotides become primers for use with DNA polymerase. The DNA is copied by primer extension to make a second copy of both strands. By repeating the cycle of heat denaturation, primer hybridisation and extension, the target DNA can be amplified a million fold or more in about two to four hours. PCR is a molecular biology tool, which must be used in conjunction with a detection technique to determine the results of amplification. An advantage of PCR is that it increases sensitivity by amplifying the amount of target DNA by 1 million to 1 billion fold in approximately 4 hours. PCR can be used to amplify any known nucleic acid in a diagnostic context (Mok et al., *Gynaecologic Oncology*, 1994, 52: 247-252,).

An allele specific amplification technique such as Amplification Refractory Mutation System (ARMS™) (Newton et al., *Nucleic Acids Res.*, 1989, 17, 2503-2516) can also be used to detect single base mutations. Under the appropriate PCR amplification conditions a single base mismatch located at the 3'-end of the primer is sufficient for preferential amplification of the perfectly matched allele (Newton et al., 1989, supra), allowing the discrimination of closely related species. The basis of an amplification system using the primers described above is that oligonucleotides with a mismatched 3'-residue will not function as primers in the PCR under appropriate conditions. This amplification system allows genotyping solely by inspection of reaction mixtures after agarose gel electrophoresis.

Analysis of amplification products can be performed using any method capable of separating the amplification products according to their size, including automated and manual gel electrophoresis, mass spectrometry, and the like.

The methods of nucleic acid isolation, amplification and analysis are routine for one skilled in the art and examples of protocols can be found, for example, Green & Sambrook, Eds., Molecular Cloning: A Laboratory Manual, (2012, 4th edition, Vol. 1-3, ISBN 9781936113422), Cold Spring Harbor Laboratory Press, Cold Spring Harbor, N.Y.) Particularly useful protocol source for methods used in PCR amplification is *PCR (Basics: From Background to Bench)* by M. J. McPherson, S. G. Mailer, R. Beynon, C. Howe, Springer Verlag; 1st edition (Oct. 15, 2000), ISBN: 0387916008.

The present invention also provides predictive and diagnostic kits comprising degenerate primers to amplify a target nucleic acid in the ERα gene and instructions comprising; amplification protocol and analysis of the results. The kit may alternatively also comprise buffers, enzymes, and containers for performing the amplification and analysis of the amplification products. The kit may also be a component of a screening, or diagnostic kit comprising other tools such as DNA microarrays, or other supports. Preferably, the kit also provides one or more control templates, such as nucleic acids isolated from normal tissue sample, and/or a series of samples representing different variances in the reference genes.

In one embodiment, the kit provides two or more primer pairs, each pair capable of amplifying a different region of the reference (ERα) gene (each region a site of potential variance) thereby providing a kit for analysis of expression of several gene variances in a biological sample in one reaction or several parallel reactions.

Primers in the kits may be labelled, for example fluorescently labelled, to facilitate detection of the amplification products and consequent analysis of the nucleic acid variances. The kit may also allow for more than one variance to be detected in one analysis. A combination kit will therefore comprise of primers capable of amplifying different segments of the reference gene. The primers may be differentially labelled, for example using different fluorescent labels, so as to differentiate between the variances.

In another aspect, the invention provides a method of treating a patient suffering from cancer comprising: determining the mutant or wild type status of the ERα gene in the patient's tumour cells and if the ERα gene is mutant, administering to the patient an effective amount of a compound of Formula (I).

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. "Less effective" means that the treatment results in a therapeutically significant lower level of pharmacological effectiveness and/or a therapeutically greater level of adverse physiological effects.

According to another aspect of the invention there is provided the use of a compound of Formula (I) or a pharmaceutically-acceptable salt thereof to treat a cancer patient whose tumour cells have been identified as possessing a mutant ERα gene. In one embodiment the compound of Formula (I) is Example 1.

According to another aspect of the invention there is provided a compound of Formula (I) or a pharmaceutically-acceptable salt thereof for treating cancers with tumour cells identified as harbouring mutant ERα gene. In one embodiment the compound of Formula (I) is Example 1.

According to another aspect of the invention there is provided a method of treating cancers with tumour cells identified as harbouring mutant ERα gene comprising administering an effective amount of a compound of Formula (I) or a pharmaceutically-acceptable salt thereof. In one embodiment the compound of Formula (I) is Example 1.

In still further embodiments, the invention relates to pharmaceutical composition comprising a compound of Formula (I) for use in the prevention and treatment of cancer with tumour cells identified as harbouring a mutant ERα gene. In one embodiment the compound of Formula (I) is Example 1.

For all the aspects above, mutant forms of ERα determined/identified are at all positions across the gene.

For all the aspects above, using tumours such as breast cancer as an example, particular mutant forms of ERα determined/identified are those at positions Ser463Pro, Val543Glu, Leu536Arg, Tyr537Ser, Tyr537Asn and Asp538Gly.

BRIEF DESCRIPTION OF THE FIGURES

FIGS. 11 and 12 show the results of an HCC1428 long term estrogen deprived (LTED) xenograft efficacy study with Example 1.

EXAMPLES

Figure 1:
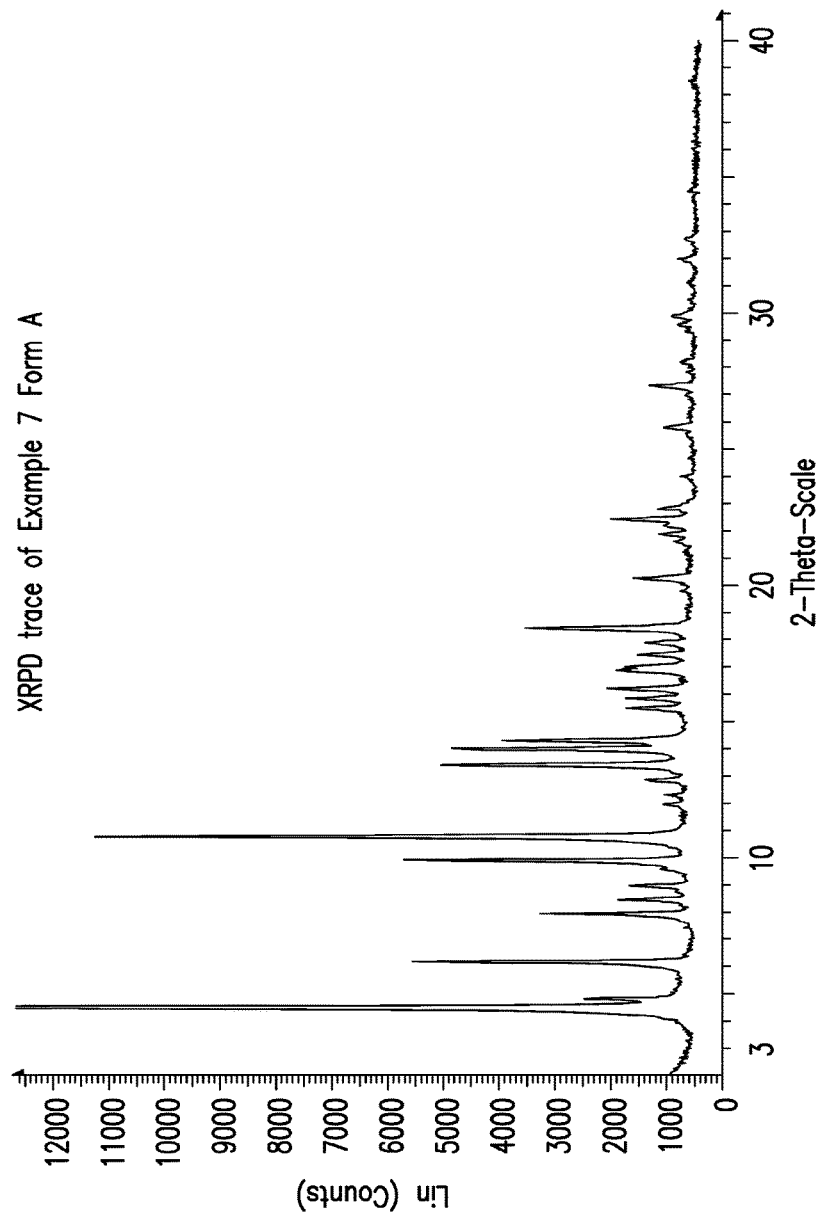
FIG. 1 shows an X-Ray Powder Diffraction Pattern of Example 7 Form A

The invention will now be illustrated in the following Examples in which, generally:
(i) operations were carried out at ambient temperature, i.e. in the range 17 to 25° C. and under an atmosphere of an inert gas such as nitrogen unless otherwise stated;
(ii) evaporations were carried out by rotary evaporation or utilising Genevac equipment or Biotage v10 evaporator in vacuo and work-up procedures were carried out after removal of residual solids by filtration;
(iii) flash chromatography purifications were performed on an automated Teledyne Isco CombiFlash® Rf or Teledyne Isco CombiFlash® Companion® using pre-packed RediSep Rf Gold™ Silica Columns (20-40 m, spherical particles), GraceResolv™ Cartridges (Davisil® silica) or Silicycle cartridges (40-63 m).
(iv) preparative chromatography was performed on a Gilson prep HPLC instrument with UV collection;
(v) chiral preparative chromatography was performed on a Gilson instrument with UV collection (233 injector/fraction collector, 333 & 334 pumps, 155 UV detector) or a Varian Prep Star instrument (2×SD1 pumps, 325 UV detector, 701 fraction collector) pump running with Gilson 305 injection;
(vi) yields, where present, are not necessarily the maximum attainable;
(vii) in general, the structures of end-products of the Formula I were confirmed by nuclear magnetic resonance (NMR) spectroscopy; NMR chemical shift values were measured on the delta scale [proton magnetic resonance spectra were determined using a Bruker Avance 500 (500 MHz) or Bruker Avance 400 (400 MHz) instrument]; measurements were taken at ambient temperature unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal
(viii) in general, end-products of the Formula I were also characterised by mass spectroscopy following liquid chromatography (LCMS or UPLC); UPLC was carried out using a Waters UPLC fitted with Waters SQ mass spectrometer (Column temp 40, UV=220-300 nm, Mass Spec=ESI with positive/negative switching) at a flow rate of 1 ml/min using a solvent system of 97% A+3% B to 3% A to 97% B over 1.50 mins (total runtime with equilibration back to starting conditions etc 1.70 min), where A=0.1% formic acid in water (for acid work) or 0.1% ammonia in water (for base work) B=acetonitrile. For acid analysis the column used was Waters Acquity HSS T3 1.8 μm 2.1×50 mm, for base analysis the column used was Waters Acquity BEH 1.7 m 2.1×50 mm; LCMS was carried out using a Waters Alliance HT (2795) fitted with a Waters ZQ ESCi mass spectrometer and a Phenomenex Gemini-NX (50×2.1 mm 5 μm) column at a flow rate of 1.1 ml/min 95% A to 95% B over 4 min with a 0.5 min hold. The modifier is kept at a constant 5% C (50:50 acetonitrile:water 0.1% formic acid) or D (50:50 acetonitrile:water 0.1% ammonium hydroxide (0.88 SG) depending on whether it is an acidic or basic method.

(ix) ion exchange purification was generally performed using a SCX-2 (Biotage, Propylsulfonic acid functionalized silica. Manufactured using a trifunctional silane. Non end-capped) cartridge.

(x) intermediates purity was assessed by thin layer chromatographic, mass spectral, HPLC (high performance liquid chromatography) and/or NMR analysis;

(xi) For XRPD analysis of Example 7, samples were mounted on zero background silicon wafers and analysed using the PANalytical CubiX Pro diffractometer (1=1.5418 Å). Samples were spun to improve counting statistics. Data was collected in reflection geometry in theta-2theta configuration over the scan range 2° to 40° 2-theta with 25 second exposure per 0.025067° increment. X-rays were generated by a copper long-fine focus tube operated at 45 kV and 40 mA. Persons skilled in the art of X-ray powder diffraction will realise that the relative intensity of peaks can be affected by, for example, grains above 30 microns in size and non-unitary aspect ratios that may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values;

(xii) For XRPD analysis of Example 1, The X-ray powder diffractogram was determined by mounting a sample of the crystalline material on a Panalytical single silicon crystal (SSC) wafer mount and spreading out the sample into a thin layer with the aid of a microscope slide. The sample was spun at 30 revolutions per minute (to improve counting statistics) and irradiated with X-rays generated by a copper long-fine focus tube operated at 45 kV and 40 mA with a wavelength of 1.5418 angstroms. The X-ray beam was passed through a 0.04 rad soller slit, then an automatic variable divergence slit set at 20 mm and finally a 20 mm beam mask. The reflected radiation was directed through a 20 mm antiscatter slit and a 0.04 rad soller slit. The sample was exposed for 1.905 seconds per 0.0025067° 2-theta increment (continuous scan mode) over the range 2 degrees to 40 degrees 2-theta in theta-theta mode. The running time was 3 minutes and 36 seconds. The instrument was equipped X-Celerator detector. Control and data capture was by means of a Dell Pentium 4HT Workstation operating with X'Pert Industry software.

(xiii) Differential Scanning Calorimetry: Analytical Instrument: TA Instruments Q1000 DSC. Typically less than 5 mg of material contained in a standard aluminium pan fitted with a lid was heated over the temperature range 25° C. to 300° C. at a constant heating rate of 10° C. per minute. A purge gas using nitrogen was used-flow rate 50 ml per minute.

(xiv) Thermogravimetric Analysis Analytical Instrument: TA Instruments Q5000 TGA. Typically less than 10 mg of material is placed on a 100 μl platinum pan and heated over the temperature range 30° C. to 150° C. at a constant heating rate of 10° C. per minute.

(xv) the following abbreviations have been used:—
aq. aqueous
CDCl₃ deutero-chloroform
Conc. concentrated
DCM dichloromethane
DMA N,N-dimethylacetamide
DMSO dimethyl sulphoxide
DSC differential scanning calorimetry,
EtOH ethanol
EtOAc ethyl acetate
IPA/iPrOH isopropyl alcohol
MeCN acetonitrile
MTBE methyltertbutyl ether
rt/RT room temperature
sat. saturated
sol. solution
THF tetrahydrofuran
TFA trifluoroacetic acid
TGA Thermogravimetric analysis Example 1

(E)-3-(3,5-Difluoro-4-((1R,3R)-2-(2-fluoro-2-methylpropyl)-3-methyl-2,3,4,9-tetrahydro-1H-pyrido[3,4-b]indol-1-yl)phenyl)acrylic acid

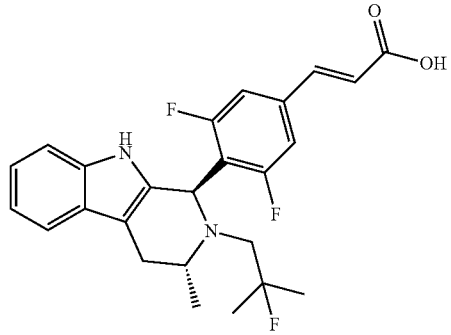 [SMILES: C[C@@H]1Cc2c([nH]c3ccccc23)[C@@H](c2c(F)cc(/C=C/C(=O)O)cc2F)N1CC(C)(C)F]

The following processes should be carried out under an atmosphere of nitrogen in the absence of light as a light degradation product [(R,E)-3-(3,5-difluoro-4-(2-(2-fluoro-2-methylpropyl)-3-methyl-4,9-dihydro-3H-pyrido[3,4-b]indol-2-ium-1-yl)phenyl)acrylate] may be formed.

(E)-Methyl 3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylate (350 g, 766.69 mmol) was charged to a 5 L fixed vessel. Isopropyl alcohol (2.80 L) was added to the vessel. Sodium hydroxide (5M, 460 ml, 2.30 mol) was added in one portion and the mixture was stirred at 21° C. for 16 hrs. The dark solution was screened through a filter to remove particulates. The filtrate was returned to the reactor vessel. The filter and filtrate collection vessel were washed with isopropanol (700 ml) and the washings were added to the reactor vessel. The reaction mixture was agitated and water (1.75 L) was added. Concentrated hydrochloric acid (37% w/w, 165 ml, 1.92 mol) was charged to the vessel. Further hydrochloric acid (21.5 ml) was added to the vessel to adjust the pH between 4.0 and 4.5. The solution was heated to 50° C. Water (1.92 L) added to the vessel over 1 hour maintaining the internal temperature between 50-53° C. The jacket temperature was raised to 70° C. to maintain the reactor temperature in this range during the addition. Within 10 minutes of completion of the water addition, the mixture self seeded and started to crystallise. The mixture was held at 50-52° C. for 1.5 hours (jacket set temperature 58° C.). The resulting yellow suspension was cooled to 5° C. (jacket temperature) over 6 hours. The slurry was held at 5° C. (jacket temperature) for 11 hrs. The resultant yellow solid was isolated by filtration. The cake was pasted with a spatula to prevent cracking of the cake. The vessel was washed with water (1.05 L). The washings were used to wash the cake. The cake was pulled dry in air then dried in vacuo to constant weight over 4 days (oven temperature=30° C.). (E)-3-(3,5-Difluoro-4-((1R,3R)-2-(2-fluoro-2-methylpropyl)-3-methyl-2,3,4,9-tetrahydro-1H-pyrido[3,4-b]indol-1-yl)phenyl)acrylic acid was thus isolated as a yellow crystalline solid, "Form B" (319.45 g, 94%). $^1$H NMR (500 MHz, DMSO, 27° C.) 1.05 (3H, d), 1.08-1.28 (6H, m), 2.35 (1H, dd), 2.58 (1H, dd), 2.8-2.97 (2H, m), 3.47-3.57 (1H, m), 5.22 (1H, s), 6.67 (1H, d), 6.91-7.06 (2H, m), 7.19 (1H, d), 7.41 (1H, d), 7.46 (2H, d), 7.54 (1H, d), 10.58 (1H, s), 12.62 (1H, s).

An alternative method for synthesising Example 1, which results in formation of Form B crystalline material, is as follows:

The following processes should be carried out under an atmosphere of nitrogen in the absence of light as a light degradation product (as described above) may be formed. (E)-methyl 3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylate (50.0 g; 109.53 mmol) was stirred in isopropyl alcohol (450 ml). Sodium hydroxide (68.34 g, 65.72 ml, 328.58 mmol) was added in one portion and the mixture stirred at 20° C. for 16 hrs. The reaction mixture was diluted with water (250 ml), the pH adjusted to pH4 with conc. hydrochloric acid (27.28 ml, 317.63 mmol) and the mixture heated to 50° C. Further water (225 ml) was added over 30 minutes, maintaining the temperature above 45° C. During the addition, the material began to crystallise. The mixture was cooled from 50° C. to 5° C. over 5 hours then the suspension was held at 0° C. for a further 11 hours. The yellow solid was isolated by filtration. The filter cake was washed with water (100 ml), dried on the filter for a further 20 minutes then dried in a vacuum oven for 16 hours to constant weight (30° C., air bleed) to give the title compound (46.52 g) as a crystalline solid (Form B).

$^1$H NMR (500 MHz, DMSO, 27° C.) 1.02-1.09 (3H, m), 1.17 (6H, dd), 2.37 (1H, dd), 2.59 (1H, dd), 2.8-2.98 (2H, m), 3.47-3.58 (1H, m), 5.24 (1H, s), 6.68 (1H, d), 6.9-7.06 (2H, m), 7.20 (1H, d), 7.38-7.51 (3H, m), 7.55 (1H, d), 10.59 (1H, s), 12.60 (1H, br).

Crystalline form B may also be isolated from ethanol/water mixtures and ethanol/MTBE mixtures.

In a further aspect of the invention there is provided crystalline form B of Example 1, isolated from isopropanol/water mixture.

In a further aspect of the invention, there is provided a process for isolation of crystalline form B of Example 1 which comprises hydrolysis of (E)-methyl 3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylate in isopropyl alcohol and base, followed by acidification and isolation of crystalline product from aqueous isopropanol.

Figure 2:
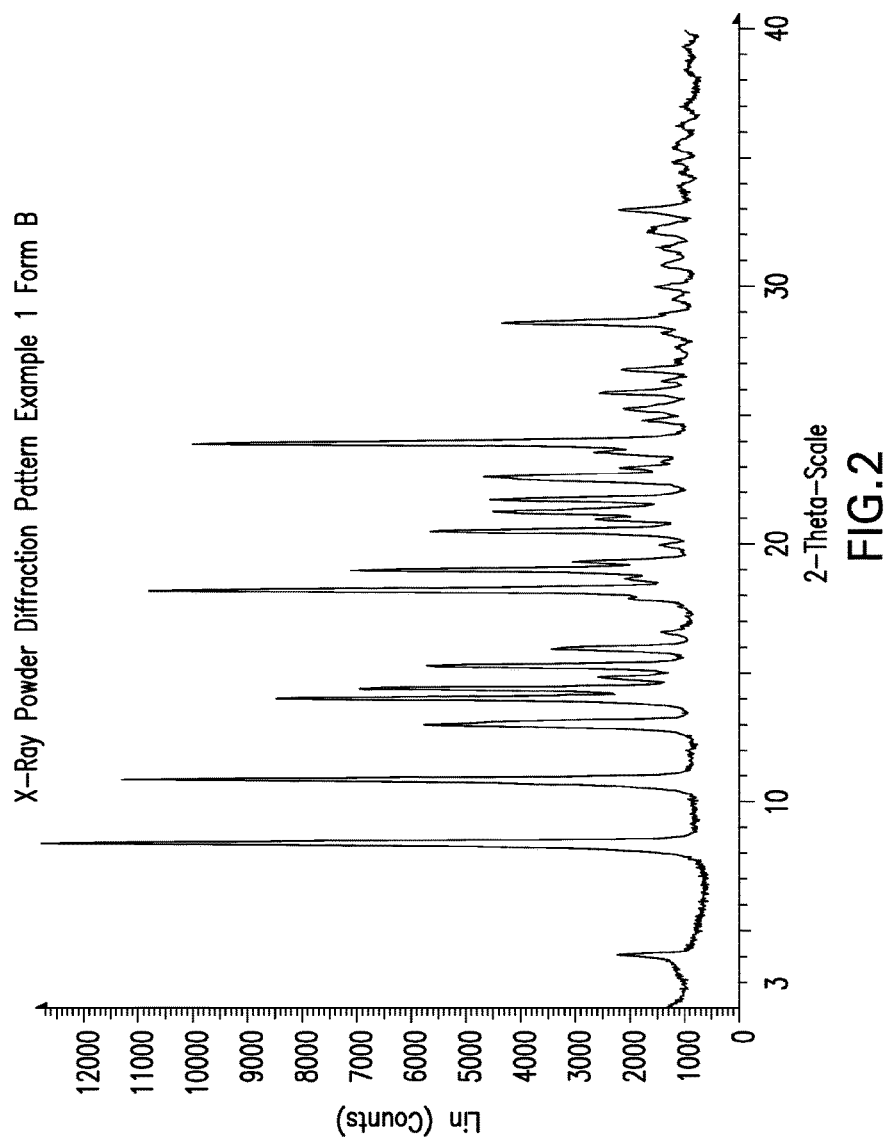
FIG. 2 shows an X-Ray Powder Diffraction Pattern of Example 1 Form B

Example 1 Form B is characterised in providing at least one of the following 20 values measured using CuKα radiation: 8.4 and 10.9. Example 1 Form B is characterised in providing an X-ray powder diffraction pattern, substantially as shown in FIG. 2. Ten X-Ray powder diffraction peaks are shown in Table A:

TABLE A

Ten X-Ray Powder Diffraction peaks for Example 1 Form B

| Angle 2-Theta (2θ) | Intensity % |
|---|---|
| 8.4 | 100 |
| 10.9 | 88.5 |
| 18.3 | 84.5 |
| 24.0 | 78.5 |
| 14.0 | 66.4 |
| 19.0 | 55.9 |
| 14.4 | 54.3 |
| 13.0 | 45 |
| 15.3 | 44.7 |
| 20.6 | 44.2 |

Figure 3:
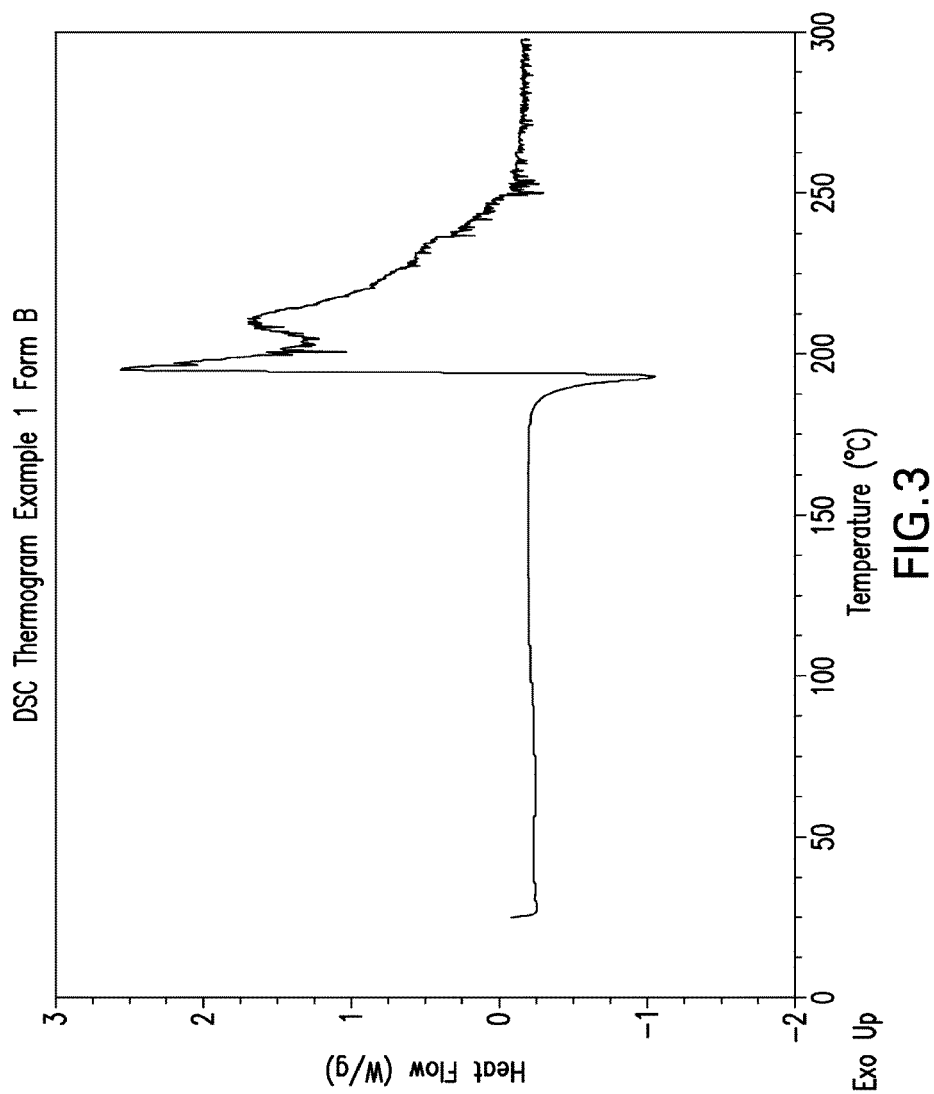
FIG. 3 shows DSC Thermogram of Example 1 Form B

DSC analysis of Example 1 Form B shows it to be a high melting solid with an endotherm showing onset of melting at 188.6° C. (FIG. 3). Example 1 shows degradation through the melt which may lead to variation in melting onset, thus the value of 188.6° C. should not be taken as absolute.

Two solvated forms of Example 1 have also been observed.

Figure 4:
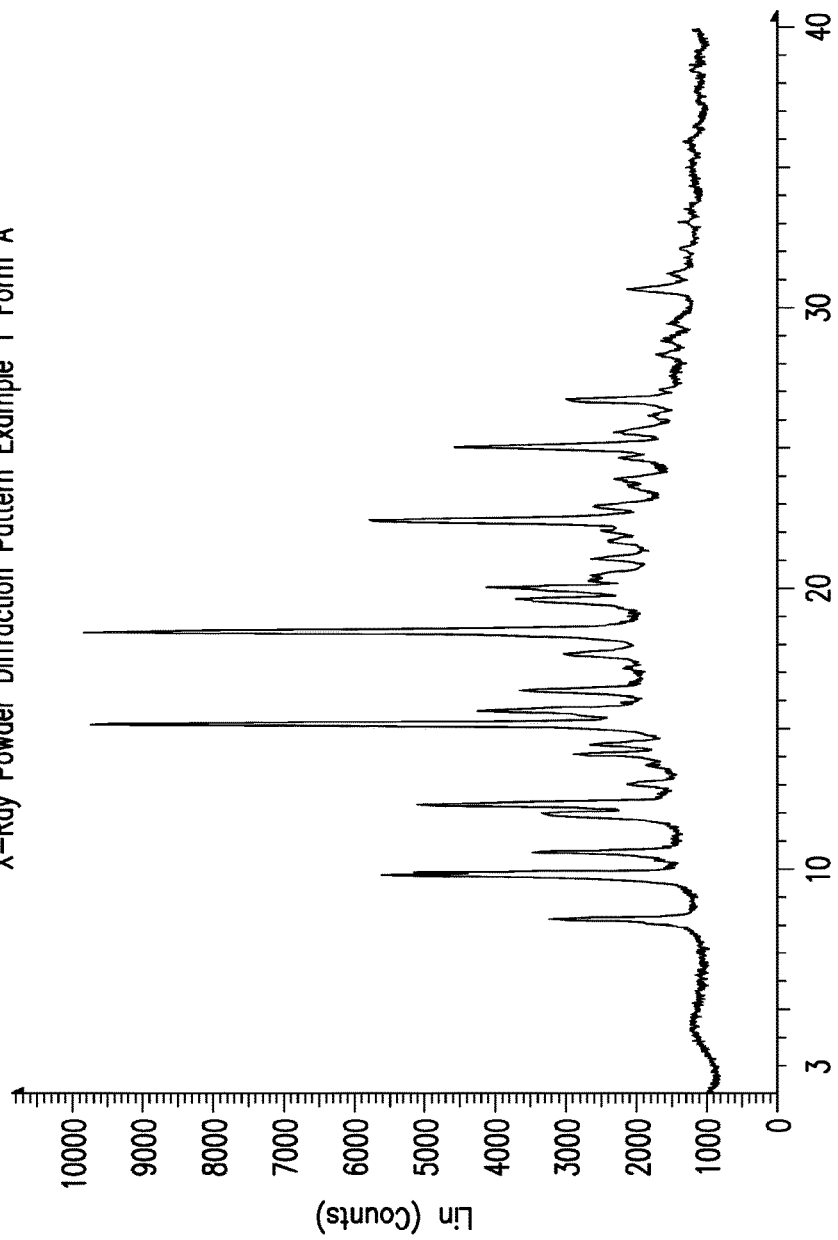
FIG. 4 shows X-Ray Powder Diffraction Pattern of Example 1 Form A
Figure 5:
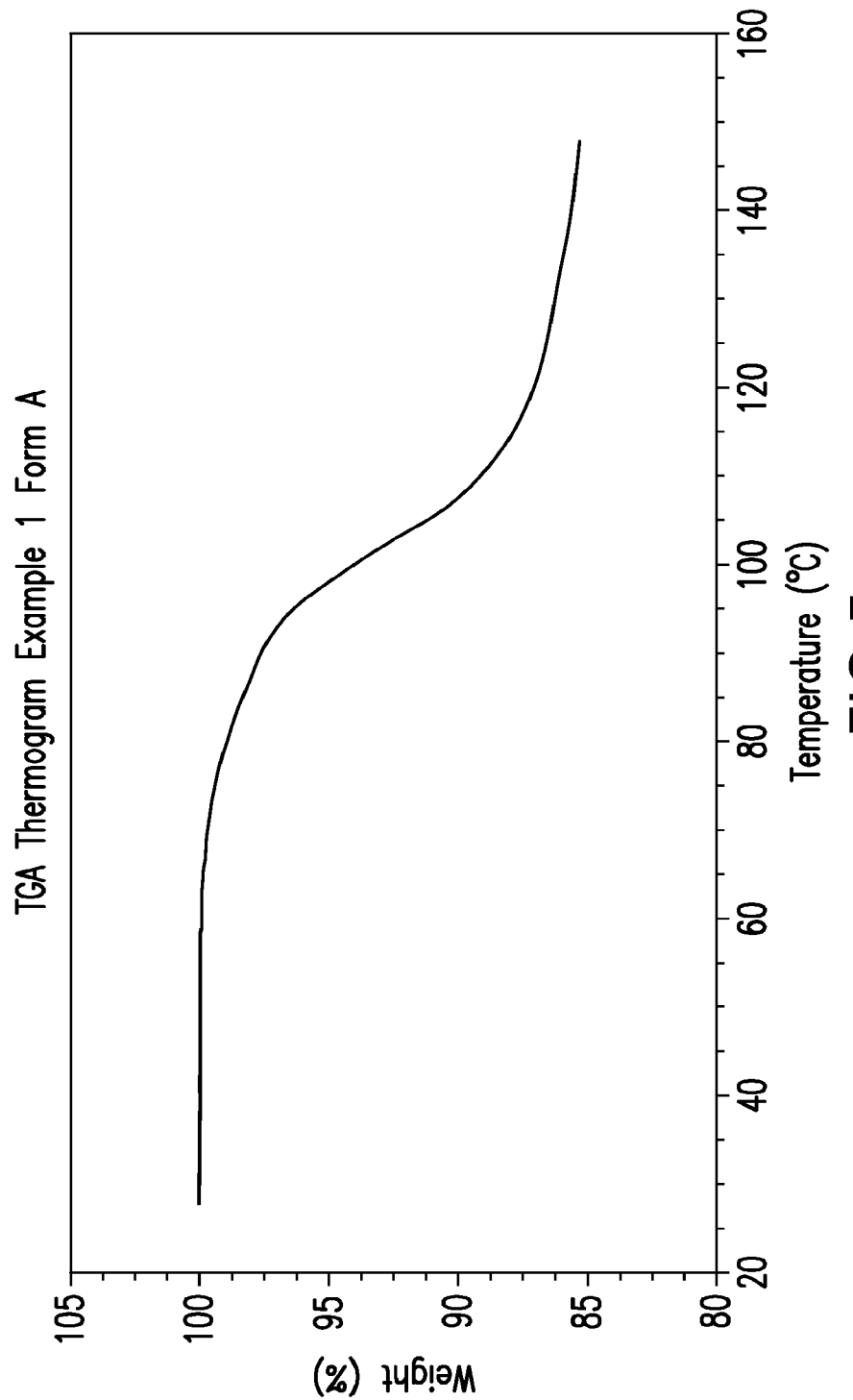
FIG. 5 shows TGA Thermogram of Example 1 Form A

Form A is a methyl tertiary butyl ether mono-solvate. The X-ray powder diffraction pattern is shown in FIG. 4. TGA shows an associated weight loss of 14.7% w/w between 55-150° C. (FIG. 5). A theoretical loss for a mono methyl tertiary butyl ether solvate is calculated to be 16.6%.

Figure 6:
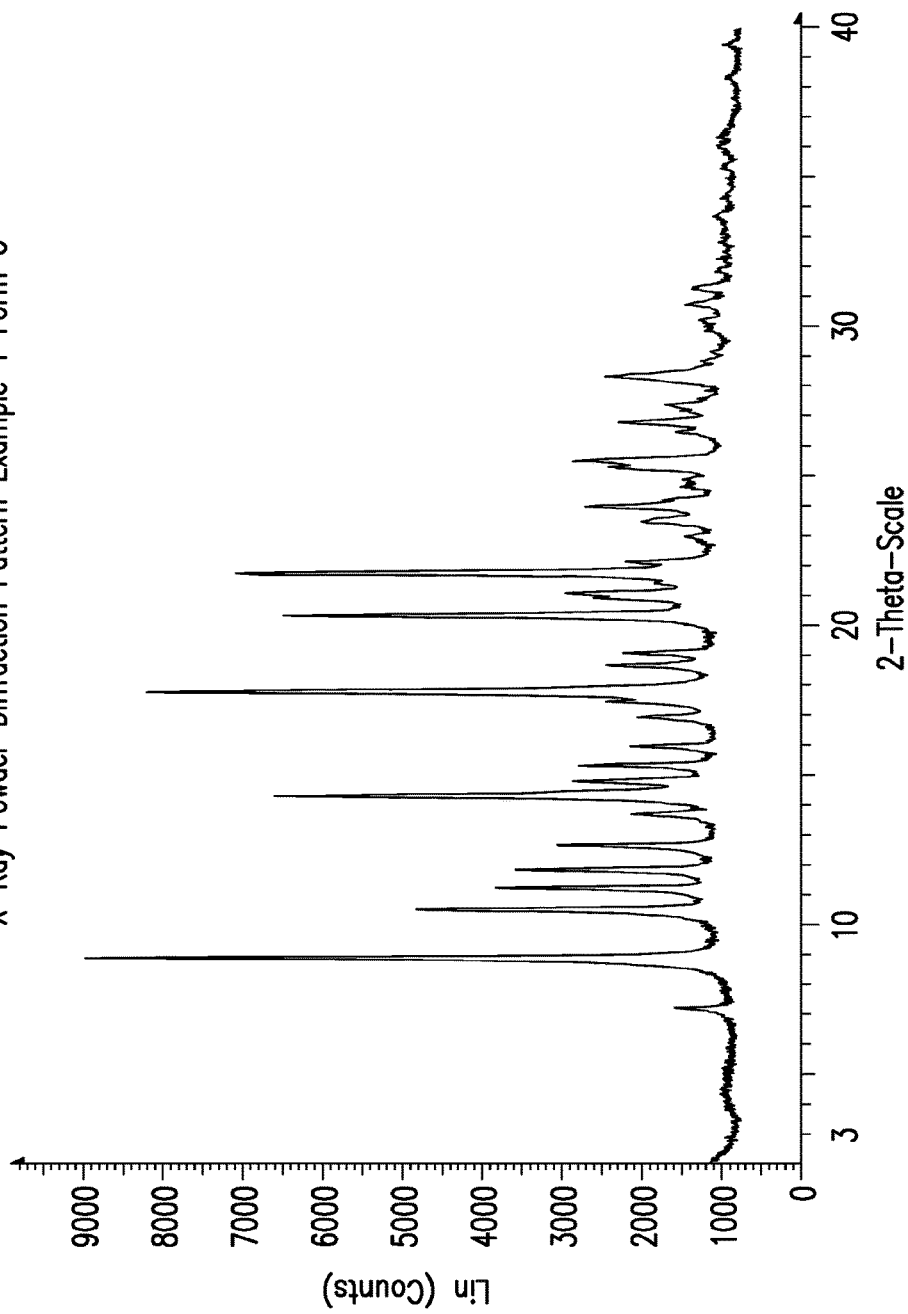
FIG. 6 shows X-Ray Powder Diffraction Pattern of Example 1 Form C
Figure 7:
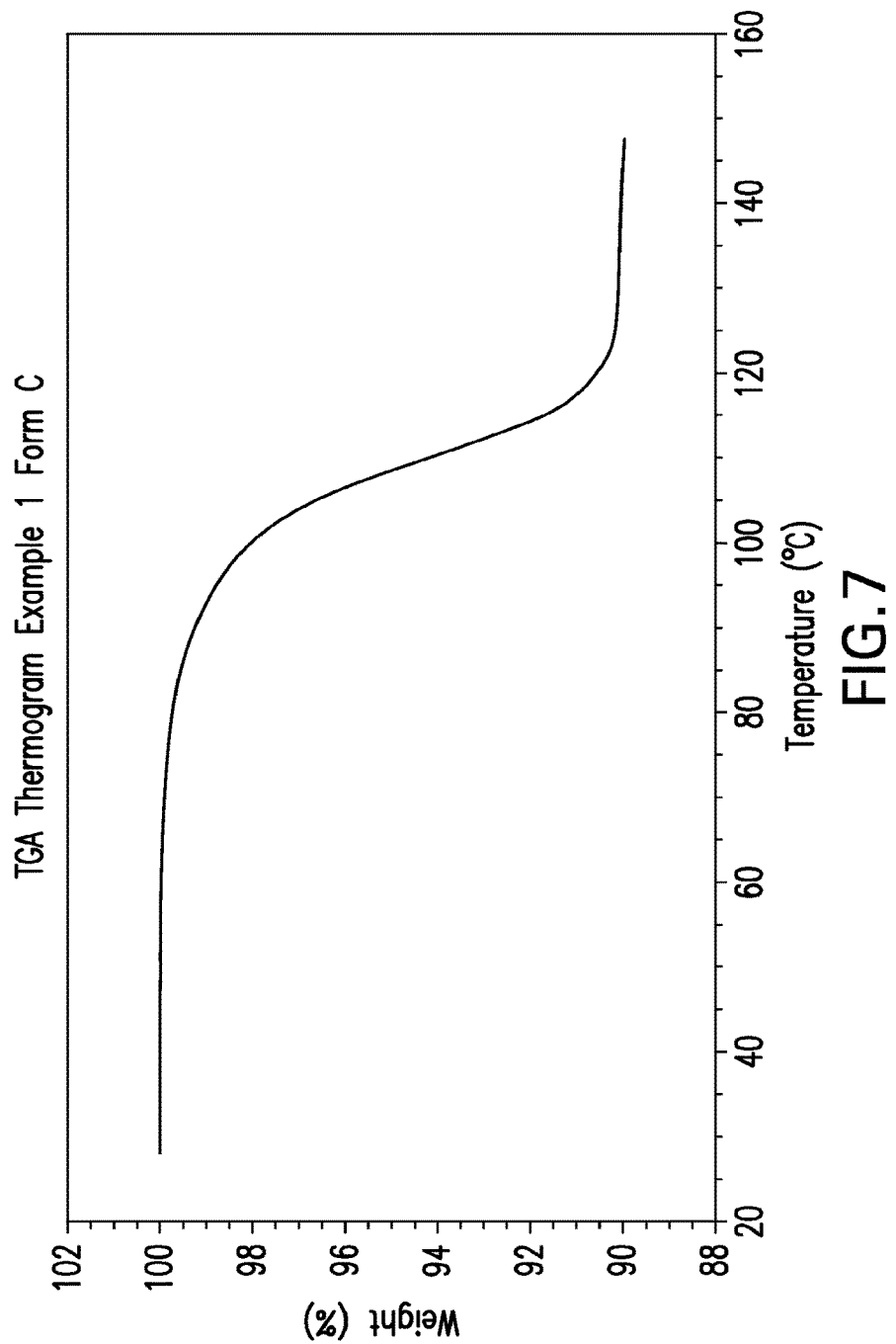
FIG. 7 shows TGA Thermogram of Example 1 Form C

Form C is an Acetone mono-solvate, the X-ray powder diffraction pattern is shown in FIG. 6. TGA shows an associated weight loss of 10.0% w/w 50-150° C. %. (FIG. 7). The theoretical loss for a mono-acetone solvate is calculated to be 11.0%.

The (E)-methyl 3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylate used as starting material was prepared as follows:—

Preparation of 2-fluoro-2-methylpropyl trifluoromethanesulfonate

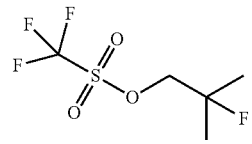

Under an atmosphere of nitrogen, 2-fluoro-2-methylpropan-1-ol (1000 g, 10.86 moles) was charged to a 20 L vessel. DCM (8.5 L) was added to the vessel. The mixture was agitated and cooled to 1° C. 2,6-Lutidine (1395 g, 13.02 moles) was added to the mixture. A solution of trifluoromethanesulfonic anhydride (3220 g; 11.41 moles) in DCM (1 L) was added over 1 hour maintaining the temperature of the reaction mixture below 5° C. (the jacket set temperature was lowered to −20° C. during the addition). The addition vessel was and lines were washed with DCM (0.5 L) and the washings were added to the vessel in one portion. The mixture was agitated at 0° C. for 1 hour affording a red solution.

A solution of concentrated hydrochloric acid (1.23 L, 37% w/w, 16.3 moles) was added to water (7 L). The dilute hydrochloric acid solution was added to the red solution and the stirred mixture was warmed to 25° C. The layers were allowed to separate and the upper aqueous layer was discarded. The organic layer was washed with water (2×5 L). The organic solution was concentrated under reduced pressure to afford a red oil. The red oil was purified by distillation using a wiped film evaporator (4.5 mbar, jacket temperature 50° C., condenser temperature 4° C.) to afford 2-fluoro-2-methylpropyl trifluoromethanesulfonate (1.69 Kg, 69%) as a pale red oil. $^1$H NMR (500 MHz, DMSO-d6, 27° C.) δ 1.40 (6H, d), 4.79 (2H, d).

Preparation of (R)—N-(1-(1H-indol-3-yl)propan-2-yl)-2-fluoro-2-methylpropan-1-amine

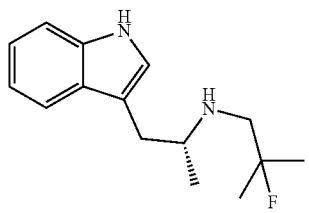 [SMILES: C[C@H](Cc1c[nH]c2ccccc12)NCC(C)(C)F]

(2R)-1-(1H-Indol-3-yl)propan-2-amine (3.81 kg, 21.21 moles) was added to a 100 L glass lined jacketed vessel under an atmosphere of nitrogen. 1,4-dioxane (23 L) was added, and the agitator was switched on. Diisopropylethylamine (5.55 L; 31.82 moles) was added to the stirred suspension followed by (2-fluoro-2-methyl-propyl)trifluoromethanesulfonate (5.55 kg, 23.77 moles). 1,4-Dioxane (4 L) was added to the vessel, and the mixture was heated to 75° C. Heating was continued for 24 hours before cooling the mixture to 25° C. Water (30.5 L) was added to the vessel, followed by toluene (30.5 L). After 40 minutes the agitator was switched off and the layers were allowed to separate. The aqueous layer was removed and water (30.5 L) was added to the organic solution. The mixture was agitated for 15 minutes before allowing the layers to separate. The aqueous layer was removed from the vessel. The organic solution was concentrated by vacuum distillation (jacket temperature 65° C., 110 mbar pressure) until approximately 27 L of distillate had been removed. The remaining solution in the vessel was cooled to afford (R)—N-(1-(1H-indol-3-yl)propan-2-yl)-2-fluoro-2-methylpropan-1-amine as a solution in toluene (33% w/w) (15.4 Kg, 97%). $^1$H NMR (500 MHz, DMSO, 27° C.) 0.98 (3H, d), 1.26 (3H, d), 1.30 (3H, d), 2.57-2.75 (3H, m), 2.81 (1H, dd), 2.84-2.92 (1H, m), 6.97 (1H, t), 7.06 (1H, t), 7.11-7.22 (1H, multiplet obscured by toluene signals), 7.34 (1H, d), 7.52 (1H, d), 10.80 (1H, s).

Preparation of sodium {2,6-difluoro-4-[(1E)-3-methoxy-3-oxoprop-1-en-1-yl]phenyl}(hydroxy)methanesulfonate

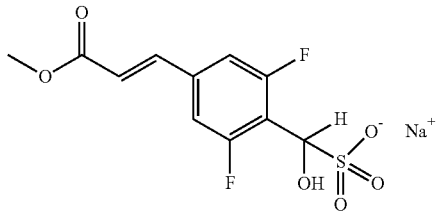

2,6-Difluoro-4-bromobenzaldehyde (1000 g, 4.39 mol) and 1,1-bis(di-tert-butylphosphino) ferrocene palladium dichloride (57.2 g; 87.76 mmol) were charged to a 20 L vessel. Tetra-n-butylammonium chloride (122 g, 438.97 mmol) was added followed by dimethylacetamide (5 L). The vessel was purged with a stream of nitrogen gas. Diisopropylethylamine (1.5 L, 8.78 mol) was added to the vessel followed by methyl acrylate (0.435 L, 4.82 mol). The mixture was agitated and heated to 60° C. The mixture was held at this temperature for 20 hours. Ethyl acetate (10 L) was added to the mixture and the heating was switched off. Water (5 L) was added to the vessel. The stirred mixture was cooled to 25° C. and stirring was continued for 10 minutes. Agitation was stopped and the layers were allowed to separate. The aqueous layer was removed and discarded. The organic layer was washed sequentially with hydrochloric acid (2.2M, 6 L) and water (5 L). Phosphonics SPM32 Scavenger (1050 g, 1050 mol) was added to the vessel and the mixture was stirred for 3 days at 25° C. The solid material was removed by filtration. The cake was washed with ethanol (5 L) and the combined filtrates were concentrated under reduced pressure to afford a solid. The solid was dissolved in ethanol (9 L) and the solution was agitated in a 20 L vessel. The solution was heated to 50° C. A solution of sodium bisulfite (460 g, 4.42 mol) in water (2.5 L) was added over 30 minutes. A thick slurry resulted which was stirred for 4 hours at 50° C. The slurry was cooled to 20° C. over 2 hours. The solid was isolated by filtration and the vessel and filter cake were washed with MTBE (2×3 L). The resulting solid was dried in vacuo to afford sodium {2,6-difluoro-4-[(1E)-3-methoxy-3-oxoprop-1-en-1-yl]phenyl)}(hydroxy)methanesulfonate (1035 g, 71%) as a light brown solid. $^1$H NMR (500 MHz, DMSO, 27° C.) δ 3.73 (3H, s), 5.32 (1H, d), 5.94 (1H, d), 6.76 (1H, d), 7.40 (2H, d), 7.60 (1H, d).

Preparation of (E)-methyl 3-(3,5-difluoro-4-formylphenyl)acrylate

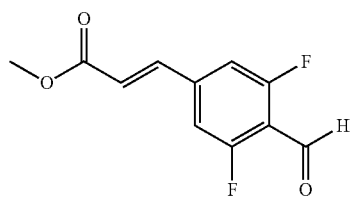 [SMILES: COC(=O)/C=C/c1cc(F)c(C=O)c(F)c1]

Under an atmosphere of nitrogen, sodium {2,6-difluoro-4-[(1E)-3-methoxy-3-oxoprop-1-en-1-yl]phenyl}(hydroxy)

methanesulfonate (1.211 kg, 3.52 mol) was to a 100 L vessel followed by potassium carbonate (0.974 kg, 7.05 mol). Water (9.1 L) was added and the agitator was started. Ethyl acetate (9.1 L) was added. The mixture was agitated at 25° C. for 5 hours. The agitator was stopped and the mixture was allowed to stand for 14 hours at 25° C. The lower aqueous phase was removed and discarded. The upper organic phase was concentrated under reduced pressure to afford a pale brown solid. The solid was dried in vacuo to afford (E)-methyl 3-(3,5-difluoro-4-formylphenyl)acrylate as a brown solid (608 g, 76%). $^1$H NMR (500 MHz, DMSO, 27° C.) δ 3.77 (3H, s), 6.94 (1H, d), 7.66 (1H, d), 7.71 (2H, d), 10.20 (1H, s).

Preparation of (E)-methyl 3-(3,5-difluoro-4-((1R, 3R)-2-(2-fluoro-2-methylpropyl)-3-methyl-2,3,4,9-tetrahydro-1H-pyrido[3,4-b]indol-1-yl)phenyl)acrylate

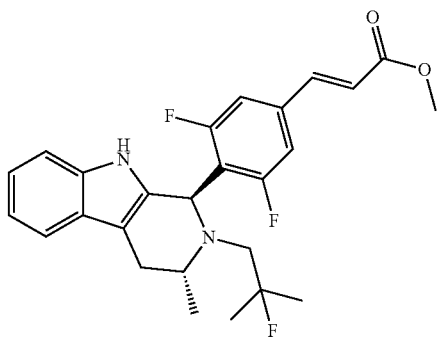 [SMILES: COC(=O)/C=C/c1cc(F)c([C@@H]2c3[nH]c4ccccc4c3C[C@@H](C)N2CC(C)(C)F)c(F)c1]

Under an atmosphere of nitrogen, (E)-Methyl 3-(3,5-difluoro-4-formylphenyl)acrylate (0.606 kg, 2.65 mol) and (R)—N-(1-(1H-indol-3-yl)propan-2-yl)-2-fluoro-2-methylpropan-1-amine (33% w/w solution in toluene, 2.0 kg, 2.65 mol) were charged to a 20 L vessel followed by toluene (4.22 L). Acetic acid (304 ml, 5.31 mol) was added to the vessel. The mixture was agitated and heated to 80° C. The mixture was agitated at 80° C. overnight before being cooled to 20° C. A solution of potassium carbonate (0.916 kg, 6.63 mol) in water (3.3 L) was added to the mixture. The mixture was stirred for 10 minutes before the agitator was switched off and the layers were allowed to separate. The aqueous layer was removed and discarded. Water (3.3 L) was charged to the reactor. The mixture was agitated for 10 minutes then allowed to stand for 10 minutes. The lower aqueous phase was removed and the organic layer was allowed to stand at room temperature overnight. The batch was heated to 80° C. Heptane (4.61 L) was added to the hot solution over 35 minutes. The stirred mixture was held at approximately 80° C. for 1 hour. The mixture was cooled to 30° C. over 2 hours during which time the product crystallised. The slurry was stirred at 30° C. for 2.5 hours. The solid was isolated by filtration. The reactor vessel walls were washed with heptane and the washings were used to wash the filter cake. The solid was dried in vacuo to afford (E)-methyl 3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylate as a pink solid (0.763 kg, 61%). $^1$H NMR (400 MHz, DMSO, 27° C.) δ 1.06 (3H, d), 1.13 (3H, d), 1.21 (3H, d), 2.35 (1H, dd), 2.58 (1H, dd), 2.8-2.98 (2H, m), 3.44-3.61 (1H, m), 3.74 (3H, s), 5.24 (1H, s), 6.80 (1H, d), 6.9-7.05 (2H, m), 7.19 (1H, d), 7.41 (1H, d), 7.50 (2H, d), 7.63 (1H, d), 10.58 (1H, s). m/z: ES+ [M+H]+ 457.

Alternative Preparation of Example 1: (E)-3-(3,5-Difluoro-4-((1R,3R)-2-(2-fluoro-2-methylpropyl)-3-methyl-2,3,4,9-tetrahydro-1H-pyrido[3,4-b]indol-1-yl)phenyl)acrylic acid

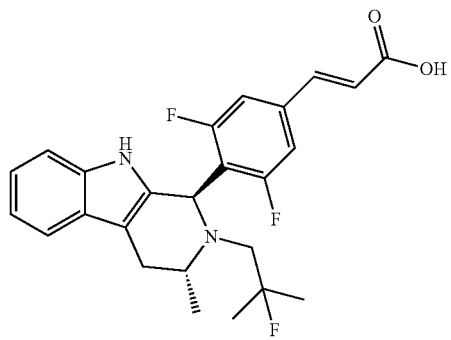 [SMILES: C[C@@H]1Cc2c([nH]c3ccccc23)[C@@H](c2c(F)cc(/C=C/C(=O)O)cc2F)N1CC(C)(C)F]

7.5M Sodium hydroxide (32.9 ml, 247.10 mmol) was added to a solution of (E)-methyl 3-(3,5-difluoro-4-((1R, 3R)-2-(2-fluoro-2-methylpropyl)-3-methyl-2,3,4,9-tetrahydro-1H-pyrido[3,4-b]indol-1-yl)phenyl)acrylate (11.28 g, 24.71 mmol) in THF (143 ml) and methanol (71.4 ml). The reaction was stirred at room temperature for 4 h. The pH of the aqueous was adjusted to ~6.5 by addition of 2N HCl solution, then the solution was extracted with diethyl ether (3×150 ml). The combined organics were dried over Na$_2$SO$_4$ and concentrated. The crude product was purified by flash silica chromatography, elution gradient 0 to 20% methanol in DCM which afforded a yellow solid. Attempted trituration with acetone/heptane failed due to higher than expected solubility. The solvents were removed to give a yellow solid which was triturated in isohexane (50 ml) with a few drops of diethyl ether, the resulting solid was filtered off and dried to give crude product (11.14 g) as a yellow powder. The solid was dissolved in ethanol (100 ml), under nitrogen and in the dark. The solution was then evaporated to 5 mBar using a vacuum pump at 62° C. in the dark. This procedure was repeated twice and the resulting yellow glass scratched with a spatula into a fine powder and subjected to 5 mBar using a vacuum pump at 62° C. for 60 min, to afford a yellow powder. The powder was then left in a vacuum oven over P2O5 at 62° C. at 300 mBar overnight to afford the title product (9.77 g, 89%) as a pale yellow solid. $^1$H NMR (400 MHz, DMSO, 27° C.) δ 1.07-1.16 (3H, m), 1.18-1.29 (6H, m), 2.39 (1H, dd), 2.62 (1H, dd), 2.92 (2H, dd), 3.56 (1H, d), 5.26 (1H, s), 6.70 (1H, d), 7.02 (2H, dd), 7.22 (1H, d), 7.47 (3H, dd), 7.58 (1H, d), 10.60 (1H, s), 12.60 (1H, s). m/z: ES+(ElectroSpray+) [M+H]+ 443.

The (E)-methyl 3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylate used as starting material was prepared as follows:—

Preparation of 2-fluoro-2-methylpropan-1-ol

Lithium aluminium hydride (3.37 g, 88.56 mmol) was added portionwise over 15 min to a cooled solution of ethyl 2-fluoro-2-methylpropanoate (9.9 g, 73.80 mmol) in diethyl ether (184 ml) at 0° C. The reaction was stirred for 1 hr, then water (3.3 ml), followed by 15% NaOH solution (3.3 ml) and water (6.7 ml) were added sequentially. The suspension was stirred for 15 min, then filtered and the solids washed with diethyl ether. The filtrate was evaporated to give 2-fluoro-2-methylpropan-1-ol (5.90 g, 87%) as a colourless oil. $^1$H NMR (400 MHz, CDCl$_3$, 27° C.) δ 1.37 (6H, d), 3.56 (2H, d), OH not observed.

Alternative Preparation of 2-fluoro-2-methylpropyl trifluoromethanesulfonate

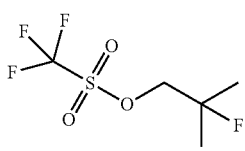

Trifluoromethanesulfonic anhydride (12.06 ml, 71.24 mmol), followed by 2,6-lutidine (11.42 ml, 81.42 mmol) were added to a solution of 2-fluoro-2-methylpropan-1-ol (6.25 g, 67.85 mmol) in DCM (146 ml) at −10° C. The reaction was stirred for 1 hr, then washed with 2N HCl (2×100 ml) and saturated NaHCO$_3$ solution (2×100 ml). The organic phase was then dried over Na$_2$SO$_4$ and concentrated to give 2-fluoro-2-methylpropyl trifluoromethanesulfonate (12.89 g, 85%) as a red oil.
$^1$H NMR (400 MHz, CDCl$_3$, 27° C.) δ 1.46 (6H, d), 4.41 (2H, d).
This intermediate may be purified by vacuum distillation. Analysis by DSC showed the material had the potential to self heat. For reasons of process safety a wiped film evaporator or similar may be preferable to a batch distillation.

Alternative Preparation of (R)—N-(1-(1H-indol-3-yl)propan-2-yl)-2-fluoro-2-methylpropan-1-amine

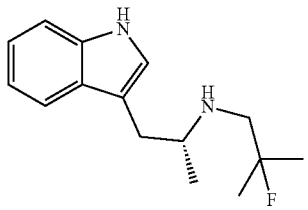 [SMILES: C[C@H](Cc1c[nH]c2ccccc12)NCC(C)(C)F]

2-Fluoro-2-methylpropyl trifluoromethanesulfonate (8.04 g, 35.87 mmol) was added to a solution of (R)-1-(1H-indol-3-yl)propan-2-amine (5.00 g, 28.70 mmol) and N-ethyl-N-isopropylpropan-2-amine (7.44 ml, 43.04 mmol) in dioxane (50 ml). The reaction was heated to 90° C. for 3 h. After cooling to room temperature, the reaction was diluted with EtOAc (200 ml) and washed with saturated. NaHCO$_3$ solution (2×100 ml). The aqueous phase was extracted with EtOAc (150 ml), then the combined organics were dried over MgSO$_4$ and concentrated. The crude product was purified by flash silica chromatography, elution gradient 100% EtOAc. Pure fractions were evaporated to dryness to afford (R)—N-(1-(1H-indol-3-yl)propan-2-yl)-2-fluoro-2-methylpropan-1-amine (6.49 g, 91%) as a brown oil. $^1$H NMR (400 MHz, CDCl$_3$, 27° C.) δ 1.14 (3H, d), 1.31 (3H, d), 1.37 (3H, d), 1.94 (1H, s), 2.63-2.87 (3H, m), 2.92 (1H, dd), 3.07 (1H, h), 7.07 (1H, d), 7.08-7.15 (1H, m), 7.16-7.24 (1H, m), 7.37 (1H, d), 7.62 (1H, d), 8.04 (1H, s). m/z: ES+ [M+H]+ 249

Alternative Preparation of (E)-methyl 3-(3,5-difluoro-4-formylphenyl)acrylate

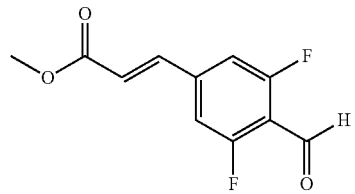 [SMILES: COC(=O)/C=C/c1cc(F)c(C=O)c(F)c1]

4-Bromo-2,6-difluorobenzaldehyde (9.99 g, 45.20 mmol) and methyl acrylate (6.14 ml, 67.81 mmol) were taken up in thoroughly degassed DMA (100 ml) and tri-o-tolylphosphine (1.376 g, 4.52 mmol), palladium(II) acetate (0.507 g, 2.26 mmol) and triethylamine (12.60 ml, 90.41 mmol) added. The reaction was stirred and heated to 80° C. for 6 hours. The reaction mixture was cooled and filtered through a layer of celite, and washed with methanol (50 ml). The crude product was pre-absorbed onto silica and purified by suction chromatography eluting with 0-10% diethyl ether/dichloromethane. Fractions containing the desired product were evaporated and triturated with diethyl ether (50 ml) to afford a yellow solid which was triturated with water (50 ml) and dried under high vacuum at 50° C. to afford (E)-methyl 3-(3,5-difluoro-4-formylphenyl)acrylate (8.85 g, 87%) as a yellow solid. $^1$H NMR (400 MHz, DMSO, 27° C.) δ 3.75 (3H, s), 6.93 (1H, d), 7.52-7.81 (3H, m), 10.18 (1H, s). No mass ion observed in LCMS.

Alternative Preparation of (E)-methyl 3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylate

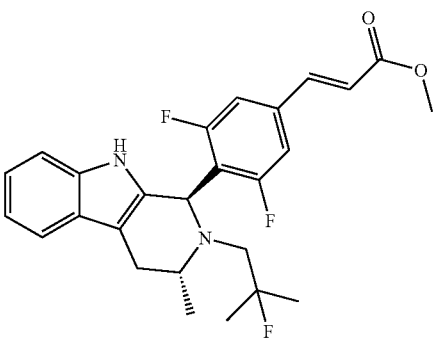 [SMILES: COC(=O)/C=C/c1cc(F)c([C@@H]2c3[nH]c4ccccc4c3C[C@@H](C)N2CC(C)(C)F)c(F)c1]

(E)-Methyl 3-(3,5-difluoro-4-formylphenyl)acrylate (6.58 g, 29.09 mmol) was added to a suspension of (R)—N-(1-(1H-indol-3-yl)propan-2-yl)-2-fluoro-2-methylpropan-1-amine (6.02 g, 24.24 mmol) in toluene (51.1 ml) and acetic acid (2.78 ml, 48.48 mmol). The reaction was heated to 80° C. for 5 hours. The reaction mixture was purified by ion exchange chromatography, using an SCX-2 column. The desired product was eluted from the column using 7M NH₃/methanol and pure fractions were evaporated to dryness to afford a brown solid. The crude product was purified by flash silica chromatography, elution gradient 0 to 30% EtOAc in heptane. Pure fractions were evaporated to dryness to afford the title product (7.52 g, 68.0%) as a yellow solid. ¹H NMR (400 MHz, DMSO, 100° C.) δ 1.10 (3H, d), 1.12-1.31 (6H, m), 2.28-2.72 (2H, m), 2.84-3.09 (2H, m), 3.52-3.69 (1H, m), 3.76 (3H, s), 5.30 (1H, s), 6.64 (1H, d), 6.9-7.11 (2H, m), 7.21 (1H, d), 7.32 (2H, d), 7.42 (1H, d), 7.58 (1H, d), 10.14 (1H, s). m/z: ES+ [M+H]+ 457

Example 2

(E)-3-(4-((1R,3R)-2-(2-Fluoro-2-methylpropyl)-3-methyl-2,3,4,9-tetrahydro-1H-pyrido[3,4-b]indol-1-yl)phenyl)acrylic acid

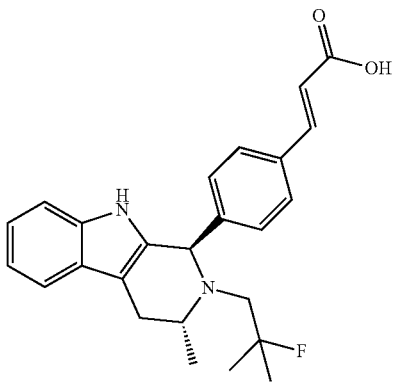 [SMILES: C[C@@H]1Cc2c([nH]c3ccccc23)[C@@H](c2ccc(/C=C/C(=O)O)cc2)N1CC(C)(C)F]

7.5M Sodium hydroxide solution (0.983 ml, 7.37 mmol) was added to a solution of (E)-methyl 3-(4-((1R,3R)-2-(2-fluoro-2-methylpropyl)-3-methyl-2,3,4,9-tetrahydro-1H-pyrido[3,4-b]indol-1-yl)phenyl)acrylate (310 mg, 0.74 mmol) in methanol (5 ml). The mixture was stirred at 20° C. for 2 hours. The reaction mixture was purified by ion exchange chromatography, using an SCX-2 column. Fractions containing the desired product were eluted from the column using 7M NH₃/methanol and pure fractions were evaporated to dryness to afford a yellow solid. The crude product was purified by preparative HPLC (Waters SunFire column, 5 µ silica, 50 mm diameter, 100 mm length), using decreasingly polar mixtures of water (containing 0.1% formic acid) and MeCN as eluents. Fractions containing the desired compound were evaporated to dryness and then loaded onto SCX-2 column and eluted with 7N ammonia in methanol to afford the title product (63.0 mg, 21.02%) as a yellow solid. ¹H NMR (400 MHz, DMSO, 30° C.) δ 1.06 (3H, d), 1.30 (3H, d), 1.47 (3H, d), 2.53-2.64 (2H, m), 2.79 (2H, s), 3.10 (1H, d), 5.08 (1H, s), 6.47 (1H, d), 6.98 (1H, t), 7.06 (1H, t), 7.19-7.37 (3H, m), 7.44 (1H, d), 7.56 (1H, d), 7.63 (2H, d), 10.81 (1H, s), 12.30 (1H, s). m/z: ES+ [M+H]+ 407.

The (E)-methyl 3-(4-((1R,3R)-2-(2-fluoro-2-methylpropyl)-3-methyl-2,3,4,9-tetrahydro-1H-pyrido[3,4-b]indol-1-yl)phenyl)acrylate used as starting material was prepared as follows:—

Preparation of (E)-methyl 3-(4-formylphenyl)acrylate

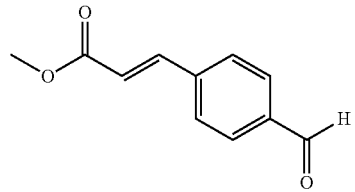

4-Bromobenzaldehyde (30 g, 162.15 mmol) and methyl acrylate (20.94 g, 243.22 mmol) were taken up in thoroughly degassed DMA (300 ml) and treated with tri-o-tolylphosphine (4.94 g, 16.21 mmol), palladium(II) acetate (1.820 g, 8.11 mmol) and triethylamine (45.2 ml, 324.29 mmol) and heated to 110° C. for 16 hours. The reaction appeared complete after this time. The reaction mixture was poured into water (4 L) and the resulting precipitate was filtered and dried. The solid was chromatographed on silica, eluting with 100% heptane to 30% EtOAc in heptane. Relevant fractions were combined and evaporated to dryness to afford a yellow solid product which was triturated with heptane, filtered and washed with cold heptane. The solid was dried to afford (E)-methyl 3-(4-formylphenyl)acrylate (25.6 g, 83%) as a yellow crystalline product. ¹H NMR (400 MHz, DMSO, 30° C.) δ 3.75 (3H, s), 6.79 (1H, d), 7.72 (1H, d), 7.93 (4H, s), 10.03 (1H, s). No mass ion observed in LCMS.

Preparation of (E)-methyl 3-(4-((1R,3R)-2-(2-fluoro-2-methylpropyl)-3-methyl-2,3,4,9-tetrahydro-1H-pyrido[3,4-b]indol-1-yl)phenyl)acrylate

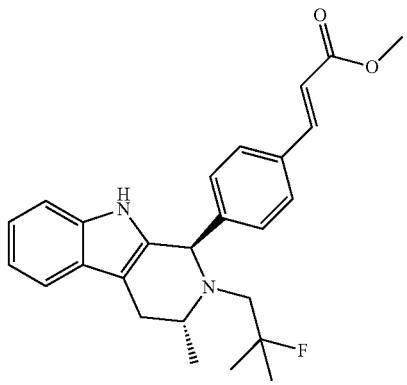 [SMILES: COC(=O)/C=C/c1ccc([C@@H]2c3[nH]c4ccccc4c3C[C@@H](C)N2CC(C)(C)F)cc1]

(R)—N-(1-(1H-indol-3-yl)propan-2-yl)-2-fluoro-2-methylpropan-1-amine (obtained as described in Example 1, preparation of starting materials) (450 mg, 1.81 mmol) and (E)-methyl 3-(4-formylphenyl)acrylate (345 mg, 1.81 mmol) were dissolved in toluene (15 ml), acetic acid (5 ml) and molecular sieves were added. The reaction was stirred at 110° C. for 16 hours under nitrogen then cooled to room temperature. The crude product was purified by ion exchange chromatography, using an SCX-2 column. The desired product was eluted from the column using 7M NH₃/methanol and pure fractions were evaporated to dryness to afford crude product. The crude product was purified by flash silica chromatography, elution gradient 0 to 30%

EtOAc in heptane. Pure fractions were evaporated to dryness to afford (E)-methyl 3-(4-((1R,3R)-2-(2-fluoro-2-methylpropyl)-3-methyl-2,3,4,9-tetrahydro-1H-pyrido[3,4-b]indol-1-yl)phenyl)acrylate (317 mg, 41.6%) as a yellow solid. $^1$H NMR (400 MHz, CDCl$_3$, 30° C.) δ 1.09 (3H, d), 1.30 (3H, d), 1.47 (3H, d), 2.48-2.78 (4H, m), 3.30 (1H, m), 3.79 (3H, s), 5.09 (1H, s), 6.40 (1H, d), 7.12 (1H, td), 7.17 (1H, td), 7.29 (1H, d), 7.34 (2H, d), 7.43 (2H, d), 7.54 (1H, d), 7.66 (2H, m). m/z: ES+ [M+H]+ 421.

Example 3

(E)-3-(3,5-Difluoro-4-((1R,3R)-2-((S)-3-fluoro-2-methylpropyl)-3-methyl-2,3,4,9-tetrahydro-1H-pyrido[3,4-b]indol-1-yl)phenyl)acrylic acid

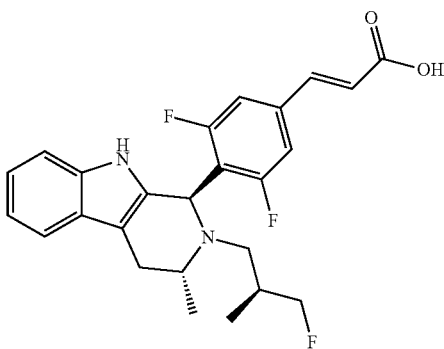 [SMILES: C[C@H](CF)CN1[C@H](c2c(F)cc(/C=C/C(=O)O)cc2F)c2[nH]c3ccccc3c2C[C@H]1C]

2M Sodium hydroxide (3.0 ml, 6.00 mmol) was added to a solution of (E)-methyl 3-(3,5-difluoro-4-((1R,3R)-2-((S)-3-fluoro-2-methylpropyl)-3-methyl-2,3,4,9-tetrahydro-1H-pyrido[3,4-b]indol-1-yl)phenyl)acrylate (275 mg, 0.60 mmol) in THF (1.5 ml)/methanol (1.5 ml). The reaction was stirred at room temperature for 3 h. EtOAc (15 ml) and water (15 ml) were added, then the pH of the aqueous was adjusted to ~7 by addition of 2N HCl. The layers were separated and the aqueous was extracted with EtOAc (15 ml). The combined organics were dried over Na$_2$SO$_4$ and concentrated. The crude product was purified by flash silica chromatography, elution gradient 0 to 10% methanol in DCM. Pure fractions were evaporated to dryness to afford the title product (250 mg, 94%) as a pale yellow solid. $^1$H NMR (400 MHz, DMSO, 30° C.) δ 0.77 (3H, d), 1.06 (3H, d), 1.93 (1H, m), 2.18 (1H, dd), 2.58 (1H, dd), 2.65 (1H, dd), 2.84 (1H, dd), 3.35 (1H, dd), 4.32 (1H, d), 4.44 (1H, d), 5.16 (1H, s), 6.67 (1H, d), 6.93-7.04 (2H, m), 7.21 (1H, d), 7.42 (1H, d), 7.46 (2H, m), 7.54 (1H, d), 10.57 (1H, s), 12.51 (1H, s). m/z: ES+ [M+H]+ 443.

The (E)-methyl 3-(3,5-difluoro-4-((1R,3R)-2-((S)-3-fluoro-2-methylpropyl)-3-methyl-2,3,4,9-tetrahydro-1H-pyrido[3,4-b]indol-1-yl)phenyl)acrylate used as starting material was prepared as follows:—

Preparation of (S)-3-fluoro-2-methylpropan-1-ol

N,N-Diethyl-1,1,2,3,3,3-hexafluoropropan-1-amine (18.25 ml, 100.57 mmol) was added dropwise to a solution of (R)-methyl 3-hydroxy-2-methylpropanoate (9.25 ml, 83.81 mmol) in DCM (77 ml) (reaction warms to ~40° C.). The reaction was stirred for 1 h at ambient temperature, then warmed to reflux for 4 h, before cooling to room temperature overnight. The reaction mixture was poured onto ice, and the layers separated. The aqueous was extracted with DCM (2×150 ml), then the combined organics were dried and carefully concentrated. The residue was dissolved in THF (200 ml) and cooled in an ice-bath. Lithium aluminium hydride (6.45 g, 167.61 mmol) was added in portions over 15 min. The reaction was stirred at 0° C. for 1 h and warmed to room temperature for a further 1 h. After cooling in an ice-bath, the reaction was quenched by addition of water (7 ml), followed by 15% NaOH (7 ml), and finally water (21 ml). MgSO$_4$ was added until a granular solid was formed. The solid was filtered through celite and the solids washed with diethyl ether (50 ml). The filtrate was washed with 2N HCl (2×100 ml), then the organic phase was dried over Na$_2$SO$_4$ and concentrated. The crude product was purified by flash silica chromatography, elution gradient 0 to 10% EtOAc in DCM. Pure fractions were evaporated to dryness to afford (S)-3-fluoro-2-methylpropan-1-ol (6.42 g, 83%) as a straw coloured oil. $^1$H NMR (400 MHz, CDCl$_3$, 30° C.) δ 0.97 (3H, dd), 1.96-2.14 (1H, m), 3.64 (2H, d), 4.3-4.42 (1H, m), 4.42-4.54 (1H, m), OH not observed.

Preparation of (S)-3-fluoro-2-methylpropyl trifluoromethanesulfonate

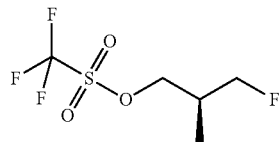

To a stirred solution of (S)-3-fluoro-2-methylpropan-1-ol (7.9 g, 85.77 mmol) in DCM (140 ml) at 0° C. was added trifluoromethanesulfonic anhydride (17.31 ml, 102.92 mmol) dropwise followed by dropwise addition of 2,6-dimethylpyridine (11.95 ml, 102.92 mmol). The reaction mixture was stirred at 0° C. for 45 min and room temperature for 30 min. The reaction mixture was diluted with DCM (60 ml), and washed sequentially with 1M HCl (3×100 ml), saturated sodium bicarbonate solution (100 ml) and saturated brine (50 ml). The organic layer was dried over Na$_2$SO$_4$, filtered and evaporated to near dryness. The solution was filtered through a plug of silica and washed through with DCM (50 ml) and evaporated to give (S)-3-fluoro-2-methylpropyl trifluoromethanesulfonate (14.38 g, 74.8%) as a brown oil. $^1$H NMR (400 MHz, CDCl$_3$, 27° C.) δ 1.09 (3H, dd), 2.24-2.44 (1H, m), 4.30 (0.5H, dd), 4.37-4.46 (1H, m), 4.52 (2.5H, tt).

Preparation of (S)—N—((R)-1-(1H-indol-3-yl)propan-2-yl)-3-fluoro-2-methylpropan-1-amine

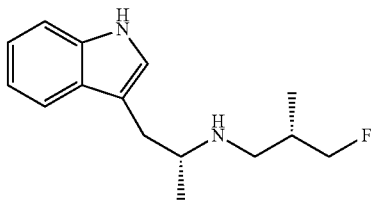 [SMILES: C[C@H](CF)CN[C@H](C)Cc1c[nH]c2ccccc12]

(S)-3-Fluoro-2-methylpropyl trifluoromethanesulfonate (666 mg, 2.97 mmol) was added to a solution of (R)-1-(1H-indol-3-yl)propan-2-amine (470 mg, 2.7 mmol) and N-ethyl-N-isopropylpropan-2-amine (0.700 ml, 4.05 mmol) in 1,4-dioxane (6.05 ml). The reaction was stirred at room temperature for 1 h. The reaction mixture was diluted with EtOAc (20 ml) and washed with water (20 ml). The aqueous was extracted with EtOAc (2×20 ml), then the combined organics were dried (MgSO$_4$) and concentrated. The crude product was purified by flash silica chromatography, elution gradient 0 to 10% methanol in DCM. Pure fractions were evaporated to dryness to afford (S)—N—((R)-1-(1H-indol-3-yl)propan-2-yl)-3-fluoro-2-methylpropan-1-amine (590 mg, 88%) as a brown oil. $^1$H NMR (400 MHz, CDCl$_3$, 30° C.) δ 0.86 (3H, dd), 1.20 (3H, d), 1.94-2.11 (1H, m), 2.64-2.74 (2H, m), 2.85-2.98 (2H, m), 3.05-3.15 (1H, m), 4.13-4.39 (2H, m), 7.09 (1H, d), 7.12 (2H, ddd), 7.20 (1H, ddd), 7.33-7.41 (1H, m), 7.56-7.65 (1H, m), 8.10 (1H, s). m/z: ES+ [M+H]+ 249

Preparation of (E)-methyl 3-(3,5-difluoro-4-((1R,3R)-2-((S)-3-fluoro-2-methylpropyl)-3-methyl-2,3,4,9-tetrahydro-1H-pyrido[3,4-b]indol-1-yl)phenyl)acrylate

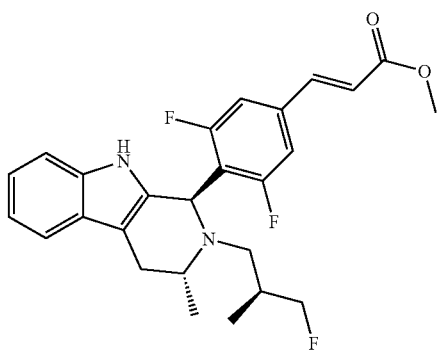 [SMILES: COC(=O)/C=C/c1cc(F)c([C@@H]2c3[nH]c4ccccc4c3C[C@@H](C)N2C[C@H](C)CF)c(F)c1]

Acetic acid (2.0 ml) was added to a solution of (S)—N—((R)-1-(1H-indol-3-yl)propan-2-yl)-3-fluoro-2-methylpropan-1-amine (273 mg, 1.10 mmol) and (E)-methyl 3-(3,5-difluoro-4-formylphenyl)acrylate (obtained as described in Example 1, preparation of starting materials) (226 mg, 1 mmol) in toluene (8.0 ml). The reaction was warmed to 95° C. for 2.5 h. The volatiles were removed under vacuum, then the residue was passed through an SCX-2 column. The column was then eluted with 7M NH$_3$/methanol to liberate the product. The filtrate was concentrated and the crude product was purified by flash silica chromatography, elution gradient 0 to 10% methanol in DCM. Pure fractions were evaporated to dryness to afford (E)-methyl 3-(3,5-difluoro-4-((1R,3R)-2-((S)-3-fluoro-2-methylpropyl)-3-methyl-2,3,4,9-tetrahydro-1H-pyrido[3,4-b]indol-1-yl)phenyl)acrylate (282 mg, 61.8%) as a pale yellow solid. $^1$H NMR (400 MHz, CDCl$_3$, 30° C.) δ 0.82 (3H, d), 1.12 (3H, d), 1.81-1.99 (1H, m), 2.24 (1H, ddd), 2.64 (1H, ddd), 2.71 (1H, dd), 2.93-3.01 (1H, ddd), 3.42 (1H, dq), 3.81 (3H, s), 4.25-4.39 (1H, m), 4.38-4.53 (1H, m), 5.20 (1H, s), 6.39 (1H, d), 6.99 (2H, m), 7.06-7.16 (2H, m), 7.21-7.25 (1H, m), 7.52 (3H, m). m/z: ES+ [M+H]+ 457.

Example 4

(E)-3-(4-((1R,3R)-2-((S)-3-fluoro-2-methylpropyl)-3-methyl-2,3,4,9-tetrahydro-1H-pyrido[3,4-b]indol-1-yl)phenyl)acrylic acid

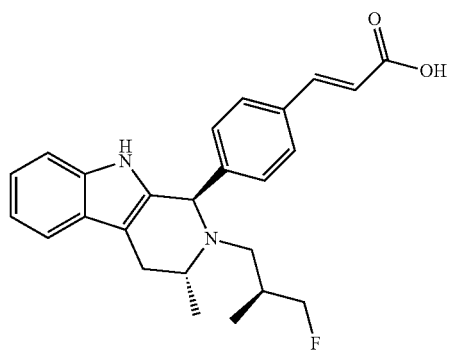 [SMILES: C[C@H](CF)CN1[C@H](c2ccc(/C=C/C(=O)O)cc2)c2[nH]c3ccccc3c2C[C@H]1C]

7.5M Sodium hydroxide solution (0.904 ml, 6.78 mmol) was added to a solution of (E)-methyl 3-(4-((1R,3R)-2-((S)-3-fluoro-2-methylpropyl)-3-methyl-2,3,4,9-tetrahydro-1H-pyrido[3,4-b]indol-1-yl)phenyl)acrylate (285 mg, 0.68 mmol) in methanol (3 ml). The mixture was stirred at 20° C. for 2 hours. The reaction mixture was purified by ion exchange chromatography, using an SCX-2 column. Fractions containing the desired product were eluted from the column using 7M NH$_3$/methanol and pure fractions were evaporated to dryness to afford a yellow solid. The crude product was purified by preparative LCMS (Phenomenex Gemini-NX axia Prep C18 OBD column, 5 μ silica, 50 mm diameter, 100 mm length), using decreasingly polar mixtures of water (containing 1% NH$_3$) and MeCN as eluents. Fractions containing the desired compound were evaporated to dryness to afford the title product (80 mg, 29.0%) as a yellow solid. $^1$H NMR (500 MHz, DMSO, 33° C.) δ 0.87 (3H, d), 1.04 (3H, d), 1.91-2.27 (2H, m), 2.50 (1H, p), 2.57-2.75 (2H, m), 3.13 (1H, s), 4.51 (2H, dd), 4.86 (1H, s), 6.47 (1H, d), 6.92-6.99 (1H, m), 7-7.09 (1H, m), 7.15-7.35 (3H, m), 7.35-7.5 (2H, m), 7.57 (2H, d), 10.64 (1H, d), CO$_2$H not observed. m/z: ES+ [M+H]+ 407.

The (E)-methyl 3-(4-((1R,3R)-2-((S)-3-fluoro-2-methylpropyl)-3-methyl-2,3,4,9-tetrahydro-1H-pyrido[3,4-b]indol-1-yl)phenyl)acrylate used as starting material was prepared as follows:—

Preparation of (E)-methyl 3-(4-((1S,3R)-3-methyl-2,3,4,9-tetrahydro-1H-pyrido[3,4-b]indol-1-yl)phenyl)acrylate

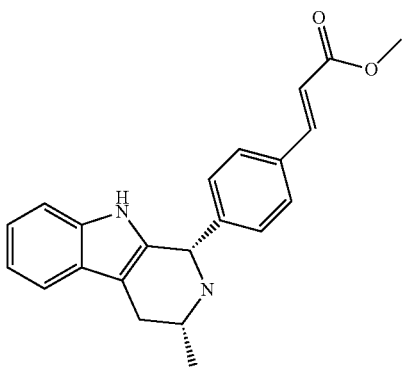 [SMILES: COC(=O)/C=C/c1ccc([C@@H]2N[C@H](C)Cc3c2[nH]c2ccccc32)cc1]

(E)-Methyl 3-(4-formylphenyl)acrylate (obtained as described in Example 2, preparation of starting materials) (18.56 g, 97.57 mmol) was added to a stirred solution of (R)-1-(1H-indol-3-yl)propan-2-amine (17 g, 97.57 mmol) in acetic acid (250 ml) at 23° C. under nitrogen. The resulting solution was stirred at 80° C. for 2 hours. The reaction mixture was evaporated to dryness and redissolved in DCM (500 ml), and washed sequentially with saturated NaHCO₃ (300 ml×2), 2M NaOH (aq) (300 ml), water (300 ml), and saturated brine (300 ml). The organic layer was dried over MgSO₄, filtered and evaporated to afford crude product. The crude product was purified by flash silica chromatography, elution gradient 1 to 7% methanol in DCM. Pure fractions were evaporated to dryness to afford (E)-methyl 3-(4-((1S,3R)-3-methyl-2,3,4,9-tetrahydro-1H-pyrido[3,4-b]indol-1-yl)phenyl)acrylate (25.1 g, 74.3%) as a beige foam. The product was mostly cis isomer, containing about 12% trans isomer which was inseparable. $^1$H NMR (400 MHz, DMSO, 30° C.) δ 1.25 (3H, d), 2.37-2.48 (1H, m), 2.74 (1H, d), 3.12 (1H, s), 3.73 (3H, s), 5.18 (1H, s), 6.64 (1H, d), 6.97 (2H, dd), 7.19 (1H, d), 7.36-7.46 (3H, m), 7.64-7.75 (3H, m), 10.19 (1H, s), no NH observed. m/z: ES+ [M+H]+ 347.

Preparation of (E)-methyl 3-(4-((1S,3R)-2-allyl-3-methyl-2,3,4,9-tetrahydro-1H-pyrido[3,4-b]indol-1-yl)phenyl)acrylate

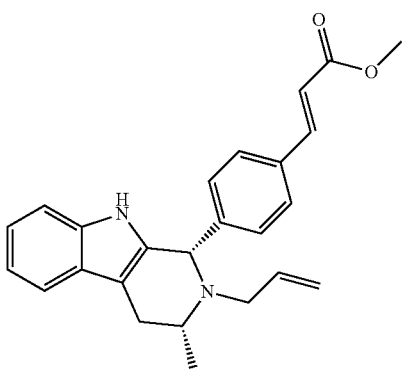 [SMILES: C=CCN1[C@@H](c2ccc(/C=C/C(=O)OC)cc2)c2[nH]c3ccccc3c2C[C@H]1C]

(E)-Methyl 3-(4-((1S,3R)-3-methyl-2,3,4,9-tetrahydro-1H-pyrido[3,4-b]indol-1-yl)phenyl)acrylate (35 g, 101.03 mmol), 3-bromoprop-1-ene (9.62 ml, 111.14 mmol) and N-ethyl-N-isopropylpropan-2-amine (19.36 ml, 111.14 mmol) were suspended in acetonitrile (160 ml), nitrogen was bubbled through for 5 min and then the mixture was sealed into a microwave tube. The reaction was heated to 140° C. for 3.5 hours in the microwave reactor and cooled to room temperature.

The reaction mixture was evaporated to dryness and redissolved in DCM (100 ml), and washed sequentially with 1M citric acid (100 ml), water (100 ml), and saturated brine (100 ml). The organic layer was dried over MgSO₄, filtered and evaporated to afford crude product. The crude product was purified by flash silica chromatography, elution gradient 0 to 20% EtOAc in heptane. Pure fractions were evaporated to dryness to afford a 50:50 mixture of (E)-methyl 3-(4-((1R,3R)-2-allyl-3-methyl-2,3,4,9-tetrahydro-1H-pyrido[3,4-b]indol-1-yl)phenyl)acrylate: (E)-methyl 3-(4-((1S,3R)-2-allyl-3-methyl-2,3,4,9-tetrahydro-1H-pyrido[3,4-b]indol-1-yl)phenyl)acrylate (10.00 g, 25.6%) as a pale yellow solid. m/z: ES+ [M+H]+ 387.

Preparation of (E)-methyl 3-(4-((1R,3R)-2-allyl-3-methyl-2,3,4,9-tetrahydro-1H-pyrido[3,4-b]indol-1-yl)phenyl)acrylate

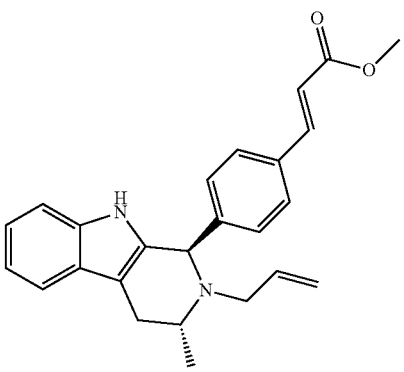 [SMILES: C=CCN1[C@H](c2ccc(/C=C/C(=O)OC)cc2)c2[nH]c3ccccc3c2C[C@H]1C]

Trifluoroacetic acid (5.59 ml, 75.29 mmol) was added to (E)-methyl 3-(4-((1S,3R)-2-allyl-3-methyl-2,3,4,9-tetrahydro-1H-pyrido[3,4-b]indol-1-yl)phenyl)acrylate (9.7 g, 25.10 mmol) in DCM (100 ml) at 20° C. under nitrogen. The resulting solution was stirred at 20° C. for 3 days. The reaction mixture was diluted cautiously with saturated NaHCO₃ solution (250 ml), and the DCM layer washed sequentially with water (250 ml) and saturated brine (250 ml). The organic layer was dried over MgSO₄, filtered and evaporated to afford crude product. The crude product was purified by flash silica chromatography, elution gradient 10 to 20% EtOAc in heptane. Fractions were evaporated to dryness to afford a 65:35 mixture of (E)-methyl 3-(4-((1R,3R)-2-allyl-3-methyl-2,3,4,9-tetrahydro-1H-pyrido[3,4-b]indol-1-yl)phenyl)acrylate: (E)-methyl 3-(4-((1S,3R)-2-allyl-3-methyl-2,3,4,9-tetrahydro-1H-pyrido[3,4-b]indol-1-yl)phenyl)acrylate (7.99 g, 82%) as a pale yellow solid. m/z: ES+ [M+H]+ 387

Preparation of (E)-methyl 3-(4-((1R,3R)-3-methyl-2,3,4,9-tetrahydro-1H-pyrido[3,4-b]indol-1-yl)phenyl)acrylate

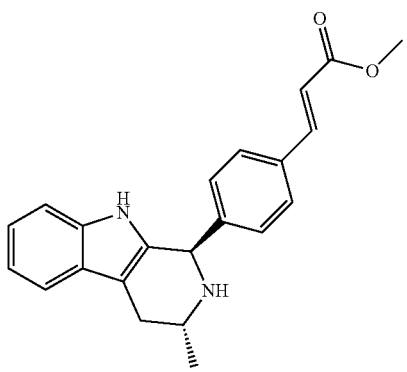 [SMILES: COC(=O)/C=C/c1ccc([C@H]2N[C@H](C)Cc3c2[nH]c2ccccc32)cc1]

7 Separate batches of 65:35 (E)-methyl 3-(4-((1R,3R)-2-allyl-3-methyl-2,3,4,9-tetrahydro-1H-pyrido[3,4-b]indol-1-yl)phenyl)acrylate: (E)-methyl 3-(4-((1S,3R)-2-allyl-3-methyl-2,3,4,9-tetrahydro-1H-pyrido[3,4-b]indol-1-yl)phenyl)acrylate (2.00 g, 5.17 mmol) were reacted as follows.

(E)-methyl 3-(4-((1R,3R)-2-allyl-3-methyl-2,3,4,9-tetrahydro-1H-pyrido[3,4-b]indol-1-yl)phenyl)acrylate (2.00 g, 5.17 mmol) and chlorotris(triphenylphosphine)rhodium(I) (Wilkinson's catalyst) (2.346 g, 2.54 mmol) were suspended in acetonitrile (12 ml) and water (2.4 ml) and nitrogen was bubbled through for 5 min before being sealed into a microwave tube. The reaction was heated to 100° C. for 60 min in the microwave reactor and cooled to room temperature. The reaction mixtures were combined and evaporated to dryness and redissolved in DCM (200 ml) and saturated NaHCO₃ solution (200 ml) added. The organic layer was washed sequentially with water (200 ml) and saturated brine (200 ml) before being dried over MgSO₄, filtered and evaporated to afford crude product. The crude product was purified by flash silica chromatography, elution gradient 0 to 5% methanol in DCM. Pure fractions were evaporated to dryness to afford (E)-methyl 3-(4-((1R,3R)-3-methyl-2,3,4,9-tetrahydro-1H-pyrido[3,4-b]indol-1-yl)phenyl)acrylate (7.02 g, 55.9%) as a pale yellow solid. ¹H NMR (400 MHz, DMSO, 30° C.) δ 1.14 (3H, d), 2.27-2.4 (1H, m), 2.81 (1H, dd), 2.94-3.05 (1H, m), 3.72 (3H, s), 5.19 (1H, s), 6.60 (1H, d), 6.94-7 (1H, m), 7.01-7.09 (1H, m), 7.26 (3H, d), 7.43 (1H, d), 7.59-7.68 (3H, m), 10.70 (1H, s), NH not observed. m/z: ES+ [M+H]+ 347

Preparation of (E)-methyl 3-(4-((1R,3R)-2-((S)-3-fluoro-2-methylpropyl)-3-methyl-2,3,4,9-tetrahydro-1H-pyrido[3,4-b]indol-1-yl)phenyl)acrylate

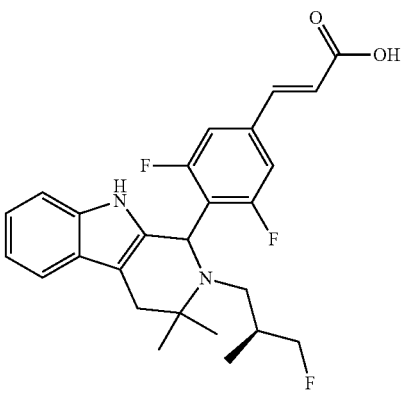 [SMILES: C[C@H](CF)CN1C(c2c(F)cc(/C=C/C(=O)O)cc2F)c2[nH]c3ccccc3c2CC1(C)C]

(S)-3-Fluoro-2-methylpropyl trifluoromethanesulfonate (obtained as described in Example 3, preparation of starting materials) (291 mg, 1.30 mmol) was added to a solution of (E)-methyl 3-(4-((1R,3R)-3-methyl-2,3,4,9-tetrahydro-1H-pyrido[3,4-b]indol-1-yl)phenyl)acrylate (300 mg, 0.87 mmol) and N,N-diisopropylethylamine (0.226 ml, 1.30 mmol) in 1,4-dioxane (5 ml). The mixture was stirred at 90° C. for 1 hour then the mixture was evaporated to dryness and the residue was partitioned between DCM (30 ml) and water (30 ml). The aqueous layer was extracted with DCM (30 ml) and the extracts combined with the organic layer. The combined extracts were filtered through a phase-separating paper and evaporated. The residue was purified by flash silica chromatography, elution solvent 15% EtOAc in heptane. Pure fractions were evaporated to dryness to afford (E)-methyl 3-(4-((1R,3R)-2-((S)-3-fluoro-2-methylpropyl)-3-methyl-2,3,4,9-tetrahydro-1H-pyrido[3,4-b]indol-1-yl)phenyl)acrylate (314 mg, 86%) as an off-white solid. ¹H NMR (400 MHz, DMSO, 30° C.) δ 0.87 (3H, d), 1.06 (3H, d), 1.9-2.28 (2H, m), 2.55-2.8 (3H, m), 2.97-3.21 (1H, m), 3.72 (3H, s), 4.31-4.69 (2H, m), 4.88 (1H, s), 6.60 (1H, dd), 6.98 (1H, t), 7.04 (1H, t), 7.17-7.35 (3H, m), 7.44 (1H, d), 7.55-7.76 (3H, m), 10.65 (1H, s). m/z: ES+ [M+H]+ 421.

Example 5

(E)-3-(3,5-difluoro-4-(2-((S)-3-fluoro-2-methylpropyl)-3,3-dimethyl-2,3,4,9-tetrahydro-1H-pyrido[3,4-b]indol-1-yl)phenyl)acrylic acid (isomer 1)*

Sodium hydroxide (184 mg, 4.61 mmol) was added to (E)-methyl 3-(3,5-difluoro-4-(2-((S)-3-fluoro-2-methylpropyl)-3,3-dimethyl-2,3,4,9-tetrahydro-1H-pyrido[3,4-b]indol-1-yl)phenyl)acrylate (isomer 1) (217 mg, 0.46 mmol) in THF (1 ml)/methanol (1 ml). The resulting solution was stirred at 20° C. for 16 hours. The reaction was diluted with water (10 ml) and the pH was adjusted to 7 by the addition of 2N HCl. The solution was extracted with EtOAc (2×20 ml). The combined organics were dried over $Na_2SO_4$ and concentrated. The crude product was purified by flash silica chromatography, elution gradient 0 to 50% EtOAc in heptane. The pure fractions were evaporated to give a crude material. The crude product was triturated using a diethyl ether/isohexane mixture to give the title product (53.0 mg, 25.2%) as a yellow solid. $^1$H NMR (400 MHz, DMSO, 27° C.) δ 0.54 (3H, d), 1.06 (3H, s), 1.34 (3H, s), 2.14 (1H, dd), 2.66 (1H, d), 2.83 (1H, d), 3.03 (1H, dd), 4.21 (1H, t), 4.33 (1H, t), 5.12 (1H, s), 6.73 (1H, d), 7.01 (2H, dtd), 7.14-7.28 (1H, m), 7.43 (1H, d), 7.54 (2H, s), 7.59 (1H, d), 10.50 (1H, s), 12.61 (1H, s), $CO_2H$ not observed. m/z: ES+ [M+H]+ 457

* Stereochemistry inferred to be (R) at the undefined centre by analogy with other examples, ie compound inferred to be: (E)-3-(3,5-difluoro-4-(1R)-(2-((S)-3-fluoro-2-methylpropyl)-3,3-dimethyl-2,3,4,9-tetrahydro-1H-pyrido[3,4-b]indol-1-yl)phenyl)acrylic acid The 3-(3,5-difluoro-4-(2-((S)-3-fluoro-2-methylpropyl)-3,3-dimethyl-2,3,4,9-tetrahydro-1H-pyrido[3,4-b]indol-1-yl)phenyl)acrylate (isomer 1) used as starting material was prepared as follows:—

Preparation of (E)-methyl 3-(4-(3,3-dimethyl-2,3,4,9-tetrahydro-1H-pyrido[3,4-b]indol-1-yl)-3,5-difluorophenyl)acrylate

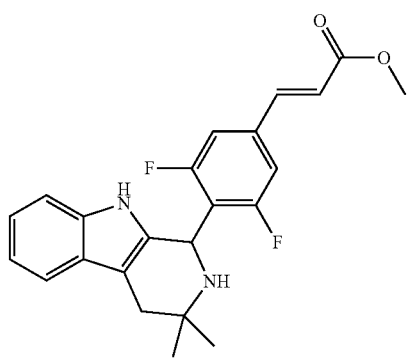 [SMILES: COC(=O)/C=C/c1cc(F)c(C2NC(C)(C)Cc3c2[nH]c2ccccc32)c(F)c1]

1-(1H-Indol-3-yl)-2-methylpropan-2-amine (807 mg, 4.29 mmol) and (E)-methyl 3-(3,5-difluoro-4-formylphenyl)acrylate (obtained as described in Example 1, preparation of starting materials) (970 mg, 4.29 mmol) were combined in acetic acid (15 ml) and the mixture heated to 80° C. for 2 hours. The reaction mixture was purified by ion exchange chromatography, using an SCX-2 column. The desired product was eluted from the column using 2M $NH_3$ in methanol and product-containing fractions were evaporated to dryness to afford (E)-methyl 3-(4-(3,3-dimethyl-2,3,4,9-tetrahydro-1H-pyrido[3,4-b]indol-1-yl)-3,5-difluorophenyl)acrylate (1610 mg, 95%) as a yellow foam. $^1$H NMR (500 MHz, DMSO, 20° C.) δ 1.15 (3H, s), 1.27 (3H, s), 2.23 (1H, s), 2.61 (2H, s), 3.75 (3H, s), 5.46 (1H, s), 6.84 (1H, d), 6.97 (2H, dtd), 7.18 (1H, d), 7.39 (1H, d), 7.58 (2H, s), 7.67 (1H, d), 10.60 (1H, s). m/z: ES– [M–H]– 395.

Preparation of (E)-methyl 3-(3,5-difluoro-4-(2-((S)-3-fluoro-2-methylpropyl)-3,3-dimethyl-2,3,4,9-tetrahydro-1H-pyrido[3,4-b]indol-1-yl)phenyl)acrylate (isomer 1)

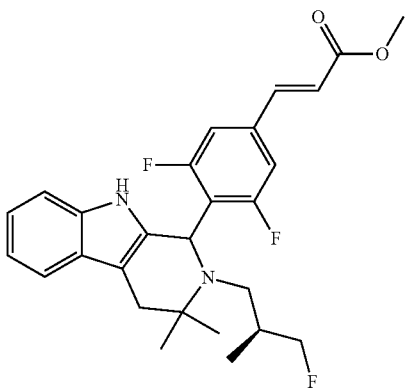 [SMILES: COC(=O)/C=C/c1cc(F)c(C2c3[nH]c4ccccc4c3CC(C)(C)N2C[C@H](C)CF)c(F)c1]

(S)-3-Fluoro-2-methylpropyl trifluoromethanesulfonate (obtained as described in Example 3, preparation of starting materials) (0.339 g, 1.51 mmol) was added to a solution of (E)-methyl 3-(4-(3,3-dimethyl-2,3,4,9-tetrahydro-1H-pyrido[3,4-b]indol-1-yl)-3,5-difluorophenyl)acrylate (0.3 g, 0.76 mmol) and N-ethyl-N-isopropylpropan-2-amine (0.458 ml, 2.65 mmol) in 1,4-dioxane (2 ml). The stirring was continued for 24 hours then the volatiles were removed under vacuum and the crude product was purified by flash silica chromatography, elution gradient 0 to 25% EtOAc in heptane. Pure fractions were evaporated to dryness to afford (E)-methyl 3-(3,5-difluoro-4-(2-((S)-3-fluoro-2-methylpropyl)-3,3-dimethyl-2,3,4,9-tetrahydro-1H-pyrido[3,4-b]indol-1-yl)phenyl)acrylate (0.202 g, 36%) as a white solid. The material was combined with another batch (0.36 g) and purified by preparative HPLC (Chiralpak IA column, 20 µm silica, 20 mm diameter, 250 mm length), Heptane:IPA 70:30 at 80 ml/min (4 injections). Fractions containing the desired compounds were evaporated to yield (E)-methyl 3-(3,5-difluoro-4-(2-((S)-3-fluoro-2-methylpropyl)-3,3-dimethyl-2,3,4,9-tetrahydro-1H-pyrido[3,4-b]indol-1-yl)phenyl)acrylate (isomer 1, first eluted, 217 mg) and (E)-methyl 3-(3,5-difluoro-4-(2-((S)-3-fluoro-2-methylpropyl)-3,3-dimethyl-2,3,4,9-tetrahydro-1H-pyrido[3,4-b]indol-1-yl)phenyl)acrylate (isomer 2, second eluted, 165 mg). Analysis was done on Chiralpak IA column, 5 µm silica, 4.6 mm diameter, 50 mm length, Heptane:IPA 70:30 at 2 ml/min.

$^1$H NMR (400 MHz, DMSO, 30° C.) δ 0.50 (3H, d), 1.02 (3H, s), 1.30 (3H, s), 2.11 (1H, dd), 2.62 (2H, d), 2.80 (1H, d), 2.99 (1H, dd), 3.74 (3H, s), 4.09-4.23 (1H, m), 4.29 (1H, d), 5.09 (1H, s), 6.81 (1H, d), 6.97 (2H, dt), 7.16 (1H, d), 7.39 (1H, d), 7.53 (2H, d), 7.64 (1H, d), 10.44 (1H, s). m/z: ES+ [M+H]+ 471.

Example 6

(E)-3-(3,5-difluoro-4-(2-(2-fluoro-2-methylpropyl)-3,3-dimethyl-2,3,4,9-tetrahydro-1H-pyrido[3,4-b]indol-1-yl)phenyl)acrylic acid (isomer 1)*

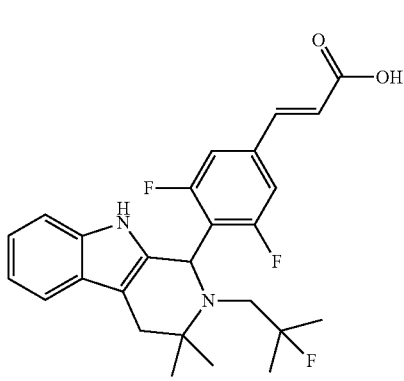 [SMILES: CC(C)(F)CN1C(c2c(F)cc(/C=C/C(=O)O)cc2F)c2[nH]c3ccccc3c2CC1(C)C]

2M Sodium hydroxide (1.6 ml, 3.20 mmol) was added to a solution of (E)-methyl 3-(3,5-difluoro-4-(2-(2-fluoro-2-methylpropyl)-3,3-dimethyl-2,3,4,9-tetrahydro-1H-pyrido[3,4-b]indol-1-yl)phenyl)acrylate (isomer 1) (148 mg, 0.31 mmol) in THF (0.8 ml)/methanol (0.8 ml). The reaction was stirred at room temperature for 3 h. EtOAc (15 ml) and water (15 ml) were added, and the pH of the aqueous was adjusted to ~7 by addition of 2N HCl. The layers were separated, and the aqueous was extracted with EtOAc (15 ml). The combined organics were dried over $Na_2SO_4$ and concentrated. The crude product was purified by flash silica chromatography, elution gradient 25 to 100% EtOAc in heptane. Pure fractions were evaporated to dryness to afford the title product (isomer 1) (124 mg, 86%) as a pale yellow solid. $^1$H NMR (400 MHz, $CDCl_3$, 30° C.) δ 1.03 (3H, d), 1.08 (3H, s), 1.16 (3H, d), 1.35 (3H, s), 2.56 (1H, dd), 2.66 (1H, d), 3.02 (1H, d), 3.17 (1H, dd), 5.24 (1H, s), 6.39 (1H, d), 7.00 (2H, d), 7.05-7.16 (2H, m), 7.20 (1H, dd), 7.28 (1H, s), 7.49 (1H, dd), 7.61 (1H, d), $CO_2H$ not observed. m/z: ES+ [M+H]+ 457.

* Stereochemistry inferred to be (R) at the undefined centre by analogy with other examples.

The (E)-methyl 3-(3,5-difluoro-4-(2-(2-fluoro-2-methylpropyl)-3,3-dimethyl-2,3,4,9-tetrahydro-1H-pyrido[3,4-b]indol-1-yl)phenyl)acrylate (isomer 1) used as starting material was prepared as follows:—

Preparation of (E)-methyl 3-(3,5-difluoro-4-(2-(2-fluoro-2-methylpropyl)-3,3-dimethyl-2,3,4,9-tetrahydro-1H-pyrido[3,4-b]indol-1-yl)phenyl)acrylate (isomer 1)

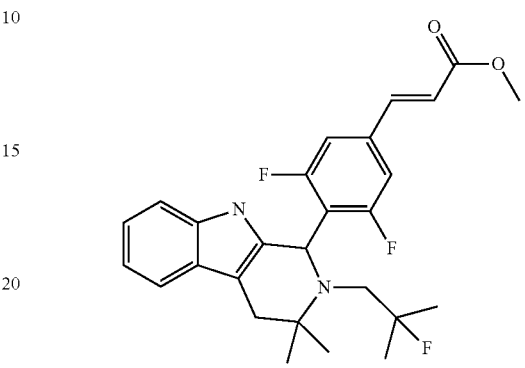

2-Fluoro-2-methylpropyl trifluoromethanesulfonate (obtained as described in Example 1, preparation of starting materials) (679 mg, 3.03 mmol) was added to a solution of (E)-methyl 3-(4-(3,3-dimethyl-2,3,4,9-tetrahydro-1H-pyrido[3,4-b]indol-1-yl)-3,5-difluorophenyl)acrylate (obtained as described in Example 5, preparation of starting materials) (600 mg, 1.51 mmol) and N-ethyl-N-isopropyl-propan-2-amine (0.915 ml, 5.30 mmol) in 1,4-dioxane (2.5 ml). The reaction was stirred at room temperature for 1 h. The reaction was then heated to 105° C. for 88 hours. The volatiles were removed under vacuum and the crude product was purified by flash silica chromatography, elution gradient 0 to 50% EtOAc in heptane. Pure fractions were evaporated to dryness to afford (E)-methyl 3-(3,5-difluoro-4-(2-(2-fluoro-2-methylpropyl)-3,3-dimethyl-2,3,4,9-tetrahydro-1H-pyrido[3,4-b]indol-1-yl)phenyl)acrylate (430 mg, 60.4%) as a white solid. The racemic product was purified by preparative HPLC (Chiralpak AD column, 20 μm silica, 50 mm diameter, 250 mm length), Heptane:Ethanol 90:10 90 ml/min. Fractions containing the desired compounds were evaporated to dryness to afford (E)-methyl 3-(3,5-difluoro-4-(2-(2-fluoro-2-methylpropyl)-3,3-dimethyl-2,3,4,9-tetrahydro-1H-pyrido[3,4-b]indol-1-yl)phenyl)acrylate (isomer 1, first eluted, 149 mg, 34.6%) and (E)-methyl 3-(3,5-difluoro-4-(2-(2-fluoro-2-methylpropyl)-3,3-dimethyl-2,3,4,9-tetrahydro-1H-pyrido[3,4-b]indol-1-yl)phenyl)acrylate (isomer 2, second eluted, 143 mg, 33.3%) as cream coloured solids. $^1$H NMR (400 MHz, $CDCl_3$, 30° C.) δ 1.01 (3H, d), 1.08 (3H, s), 1.15 (3H, d), 1.34 (3H, s), 2.55 (1H, dd), 2.66 (1H, d), 2.98-3.06 (1H, m), 3.17 (1H, dd), 3.80 (3H, s), 5.23 (1H, s), 6.38 (1H, d), 6.97 (2H, d), 7.07-7.12 (2H, m), 7.17-7.22 (1H, m), 7.32 (1H, s), 7.46-7.5 (1H, m), 7.52 (1H, d). m/z ES− [M−H]− 469.

Example 7

(E)-3-(4-(2-((S)-3-fluoro-2-methylpropyl)-3,3-dimethyl-2,3,4,9-tetrahydro-1H-pyrido[3,4-b]indol-1-yl)phenyl)acrylic acid (isomer 1)*

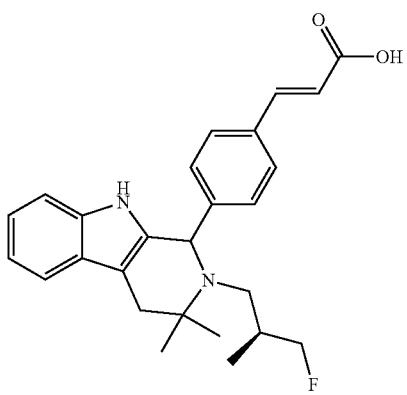 [SMILES: C[C@H](CF)CN1C(c2ccc(/C=C/C(=O)O)cc2)c2[nH]c3ccccc3c2CC1(C)C]

2M Sodium hydroxide solution (20.42 ml, 40.85 mmol) was added to a solution of (E)-methyl 3-(4-(2-((S)-3-fluoro-2-methylpropyl)-3,3-dimethyl-2,3,4,9-tetrahydro-1H-pyrido[3,4-b]indol-1-yl)phenyl)acrylate (isomer 1) (3.55 g, 8.17 mmol) in methanol (100 ml), THF (100 ml) and water (75 ml). The mixture was heated at 40° C. for 16 hours. The mixture was diluted with water (100 ml) and concentrated to a volume such that the organic solvents had been removed. The resulting aqueous solution was acidified to pH 6 with 2M HCl. The resulting aqueous suspension was extracted with DCM (500 ml) (adding brine to help separate the emulsion which formed), filtered through a phase-separating paper, dried over MgSO₄ then filtered through celite and evaporated to afford ~3.5 g of a pale yellow solid. The crude product was treated with diethyl ether/DCM (1:1, 150 ml) and sonicated. The fine suspension which formed was passed through a pad of silica (~100 g) and the silica was eluted with diethyl ether (~2 L). Product-containing fractions were combined, evaporated and dried under vacuum at 50° C. to afford the title product (2.305 g, 64.5%) as a beige solid. ¹H NMR (400 MHz, DMSO, 30° C.) δ 0.52 (3H, d), 1.03 (3H, s), 1.05-1.16 (1H, m), 1.23 (3H, s), 2.21 (1H, dd), 2.65 (1H, d), 2.84 (1H, d), 2.89 (1H, dd), 4.19 (1H, ddd), 4.31 (1H, ddd), 4.66 (1H, s), 6.50 (1H, d), 6.93 (1H, ddd), 6.98 (1H, ddd), 7.18 (1H, d), 7.38 (2H, d), 7.40 (1H, d), 7.58 (1H, d), 7.63 (2H, d), 10.18 (1H, s), 12.30 (1H, s). m/z: ES+ [M+H]+ 421.

* Stereochemistry inferred to be (R) at the undefined centre by analogy with other examples.

The product (9.0 g, 21.40 mmol) was slurried in acetonitrile (150 ml) under nitrogen in the dark for 1 hour in a stoppered 250 ml round bottomed flask. The mixture was stirred over the weekend at room temperature then filtered and washed with cold acetonitrile (60 ml) to afford a white solid which was dried under high vacuum at 40° C. for 5 hours to yield crystalline form A of the title product (7.81 g, 87%).

An XRPD trace of Crystalline form A includes the following peaks and is shown in FIG. 1.

| 2-Theta ° | % |
|---|---|
| 4.48 | 100 |
| 10.76 | 42.2 |
| 9.88 | 21.4 |
| 6.13 | 20.8 |
| 13.41 | 18.9 |
| 14.01 | 18.2 |
| 14.31 | 14.7 |
| 18.46 | 13.2 |
| 7.92 | 12.2 |
| 4.76 | 9.3 |

The (E)-methyl 3-(4-(2-((S)-3-fluoro-2-methylpropyl)-3,3-dimethyl-2,3,4,9-tetrahydro-1H-pyrido[3,4-b]indol-1-yl)phenyl)acrylate (isomer 1) used as starting material was prepared as follows:—

Preparation of (E)-methyl 3-(4-(3,3-dimethyl-2,3,4,9-tetrahydro-1H-pyrido[3,4-b]indol-1-yl)phenyl)acrylate (racemate)

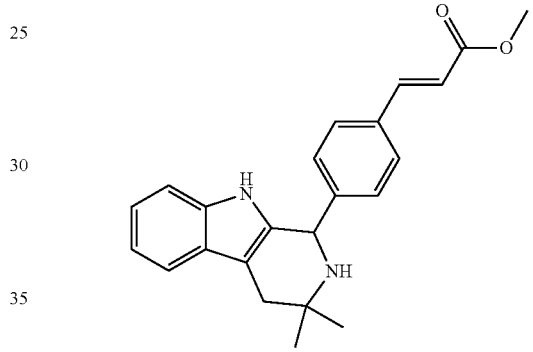

(E)-Methyl 3-(4-formylphenyl)acrylate (41.8 g, 219.62 mmol) (obtained as described in Example 2, preparation of starting materials) was added in one portion to 1-(1H-indol-3-yl)-2-methylpropan-2-amine (43.8 g, 219.62 mmol) in acetic acid (314 ml) under nitrogen. The resulting solution was stirred at 80° C. for 5 hours. The reaction mixture was concentrated in vacuo. Toluene (200 ml) was added and the residue evaporated to dryness. The azeotrope treatment was repeated twice more to give a brown solid. This was stirred in 1:1 EtOAc/heptane (500 ml) for 30 min before filtering and washing with 1:1 EtOAc/heptane. The compound was air dried to give a white solid. The crude material was suspended in 2-methyl tetrahydrofuran (750 ml), and saturated sodium bicarbonate solution was added over 10 min to the stirred mixture (effervescence), the mixture was stirred until the material dissolved and the aqueous phase remained basic. The phases were separated and the organic phase washed with brine, dried over MgSO₄, filtered and concentrated in vacuo to give a pale yellow foam (~78 g). The material was dissolved in diethyl ether (200 ml) and concentrated to dryness (repeated twice). On the second addition a proper solid was obtained. This was stirred in diethyl ether and evaporated to dryness to give (E)-methyl 3-(4-(3,3-dimethyl-2,3,4,9-tetrahydro-1H-pyrido[3,4-b]indol-1-yl)phenyl)acrylate (racemate) (73.6 g, 89%). ¹H NMR (400 MHz, CDCl₃, 30° C.) δ 1.26 (3H, s), 1.35 (3H, s), 1.42 (1H, br s), 2.69-2.82 (2H, m), 3.80 (3H, s), 5.12 (1H, s), 6.41 (1H, d), 7.06-7.16 (2H, m), 7.21 (1H, dd), 7.37 (2H, d), 7.46-7.54 (4H, m), 7.67 (1H, d). m/z: ES+ [M+H]+ 361.

Preparation of (E)-methyl 3-(4-(3,3-dimethyl-2,3,4,9-tetrahydro-1H-pyrido[3,4-b]indol-1-yl)phenyl)acrylate (isomer 1)

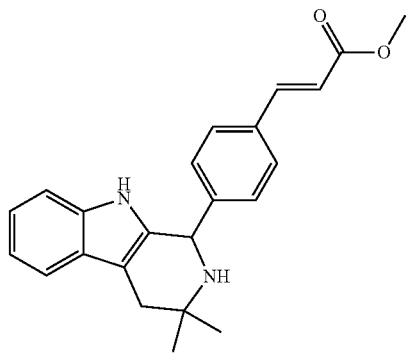 [SMILES: COC(=O)/C=C/c1ccc(C2NC(C)(C)Cc3c2[nH]c2ccccc32)cc1]

(E)-Methyl 3-(4-(3,3-dimethyl-2,3,4,9-tetrahydro-1H-pyrido[3,4-b]indol-1-yl)phenyl)acrylate (racemate) (65 g) was purified in seven injections as follows.

The racemic material was purified by preparative HPLC (Chiralpak OD column, 20 μm silica, 100 mm diameter, 250 mm length), Heptane:IPA 50:50. Fractions containing the desired compounds were evaporated to dryness to afford (E)-methyl 3-(4-(3,3-dimethyl-2,3,4,9-tetrahydro-1H-pyrido[3,4-b]indol-1-yl)phenyl)acrylate (isomer 1, first eluted, 30.3 g, 93%) and (E)-methyl 3-(4-(3,3-dimethyl-2,3,4,9-tetrahydro-1H-pyrido[3,4-b]indol-1-yl)phenyl)acrylate (isomer 2, second eluted, 28.2 g, 86%). $^1$H NMR (400 MHz, CDCl$_3$, 30° C.) δ 1.27 (3H, s), 1.36 (3H, s), 2.69-2.82 (2H, m), 3.80 (3H, s), 5.14 (1H, s), 6.43 (1H, d), 7.12 (2H, pd), 7.2-7.24 (1H, m), 7.39 (3H, d), 7.51 (3H, d), 7.68 (1H, d), NH not observed. m/z: ES+ [M+H]+ 361.

Preparation of (E)-methyl 3-(4-(2-((S)-3-fluoro-2-methylpropyl)-3,3-dimethyl-2,3,4,9-tetrahydro-1H-pyrido[3,4-b]indol-1-yl)phenyl)acrylate (isomer 1)

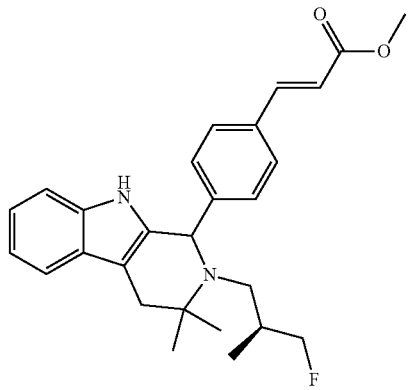 [SMILES: COC(=O)/C=C/c1ccc(C2c3[nH]c4ccccc4c3CC(C)(C)N2C[C@H](C)CF)cc1]

(S)-3-Fluoro-2-methylpropyl trifluoromethanesulfonate (obtained as described in Example 3, preparation of starting materials) (5.32 g, 21.36 mmol) was added to a solution of (E)-methyl 3-(4-(3,3-dimethyl-2,3,4,9-tetrahydro-1H-pyrido[3,4-b]indol-1-yl)phenyl)acrylate (isomer 1) (3.5 g, 9.71 mmol) and N-ethyl-N-isopropylpropan-2-amine (6.34 ml, 36.41 mmol) in 1,4-dioxane (17.5 ml). The mixture was stirred at 22° C. for 3 days. The mixture was evaporated and the residue was partitioned between DCM (150 ml) and water (150 ml). The aqueous layer was extracted with DCM (50 ml) and the extracts combined with the organic layer. The combined extracts were filtered through a phase-separating paper and evaporated. The residue was purified by flash silica chromatography, elution solvent 15% EtOAc in heptane. Fractions containing significant amounts of product began to form crystals; the tubes were agitated to encourage further crystallisation. The crystals were collected by filtration and washed with a small amount of 15% EtOAc in heptane to afford (E)-methyl 3-(4-(2-((S)-3-fluoro-2-methylpropyl)-3,3-dimethyl-2,3,4,9-tetrahydro-1H-pyrido[3,4-b]indol-1-yl)phenyl)acrylate (isomer 1) (2.91 g, 69.0%) as a white crystalline solid. Liquors from the crystallisation and other product-containing fractions were combined and evaporated. The residue was recrystallised from EtOAc/heptane to afford more 3-(4-(2-((S)-3-fluoro-2-methylpropyl)-3,3-dimethyl-2,3,4,9-tetrahydro-1H-pyrido[3,4-b]indol-1-yl)phenyl)acrylate (isomer 1) as a white crystalline solid (635 mg, 15.1%). $^1$H NMR (400 MHz, CDCl$_3$, 30° C.) δ 0.53 (3H, d), 0.95-1.07 (1H, m), 1.09 (3H, s), 1.32 (3H, s), 2.16 (1H, dd), 2.66 (1H, d), 2.94 (1H, d), 2.97 (1H, d), 3.80 (3H, s), 4.14 (1H, ddd), 4.31 (1H, ddd), 4.59 (1H, s), 6.42 (1H, d), 7.05-7.11 (2H, m), 7.13 (1H, s), 7.17 (1H, dd), 7.35 (2H, d), 7.45 (2H, d), 7.50 (1H, dd), 7.67 (1H, d). m/z: ES+ [M+H]+ 435.

Example 8

(E)-3-(4-(2-(2-fluoro-2-methylpropyl)-3,3-dimethyl-2,3,4,9-tetrahydro-1H-pyrido[3,4-b]indol-1-yl)phenyl)acrylic acid (isomer 1)*

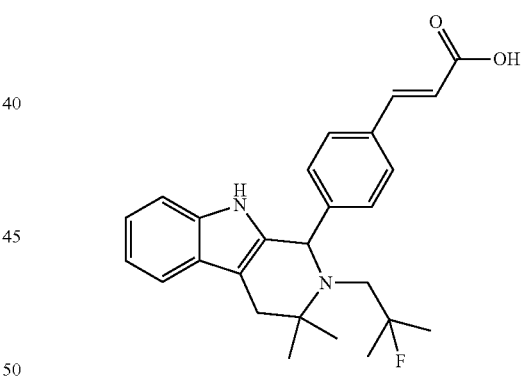

2M Sodium hydroxide solution (0.782 ml, 1.56 mmol) was added to a solution of (E)-methyl 3-(4-(2-(2-fluoro-2-methylpropyl)-3,3-dimethyl-2,3,4,9-tetrahydro-1H-pyrido [3,4-b]indol-1-yl)phenyl)acrylate (isomer 1) (68 mg, 0.16 mmol) in methanol (5 ml), THF (5.00 ml) and water (5.00 ml) and the mixture stirred for 40 hours at 22° C. The mixture was concentrated to a volume such that all of the organic solvent had been removed and was acidified to pH6 with 2M HCl. Concentrated aqueous ammonia (2 drops) was added, followed by methanol (~2 ml), giving a pale yellow solution. The crude product was purified by preparative HPLC (Waters XBridge Prep C18 OBD column, 5 silica, 50 mm diameter, 100 mm length), using decreasingly polar mixtures of water (containing 1% NH$_3$) and MeCN as eluents. Fractions containing the desired compound were evaporated to dryness to afford the title product (isomer 1)

(50.0 mg, 76%) as a yellow solid. $^1$H NMR (500 MHz, DMSO, 30° C.) δ 0.93 (3H, s), 1.19 (3H, d), 1.23 (3H, s), 1.51 (3H, d), 2.56-2.64 (2H, m), 2.75 (1H, d), 3.04 (1H, dd), 5.06 (1H, s), 6.40 (1H, d), 7.03 (1H, ddd), 7.09-7.15 (2H, m), 7.35 (1H, dd), 7.44-7.51 (5H, m), 10.87 (1H, s), $CO_2H$ not observed. m/z: ES+ [M+H]+ 421.

* Stereochemistry inferred to be (R) at the undefined centre by analogy with other examples.

The (E)-methyl 3-(4-(2-(2-fluoro-2-methylpropyl)-3,3-dimethyl-2,3,4,9-tetrahydro-1H-pyrido[3,4-b]indol-1-yl) phenyl)acrylate (isomer 1) used as starting material was prepared as follows:—

Preparation of (E)-methyl 3-(4-(2-(2-fluoro-2-methylpropyl)-3,3-dimethyl-2,3,4,9-tetrahydro-1H-pyrido[3,4-b]indol-1-yl)phenyl)acrylate (isomer 1)

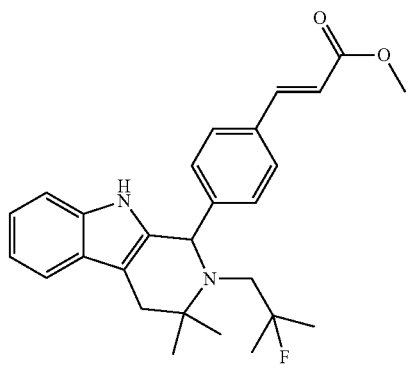 [SMILES: COC(=O)/C=C/c1ccc(C2c3[nH]c4ccccc4c3CC(C)(C)N2CC(C)(C)F)cc1]

2-Fluoro-2-methylpropyl trifluoromethanesulfonate (obtained as described in Example 1, preparation of starting materials) (389 mg, 1.73 mmol) was added to a solution of (E)-methyl 3-(4-(3,3-dimethyl-2,3,4,9-tetrahydro-1H-pyrido[3,4-b]indol-1-yl)phenyl)acrylate (racemate) (obtained as described in Example 7, preparation of starting materials) (250 mg, 0.69 mmol) and N,N-diisopropylethylamine (0.453 ml, 2.60 mmol) in 1,4-dioxane (1.25 ml). The mixture was stirred at 95° C. for 64 hours and then partitioned between DCM (30 ml) and water (30 ml). The aqueous layer was extracted with DCM (20 ml) and the extracts combined with the organic layer. The combined extracts were filtered through a phase-separating paper and evaporated. The residue was purified by flash silica chromatography, elution solvent 15% EtOAc in heptane. Pure fractions were evaporated to dryness to afford (E)-methyl 3-(4-(2-(2-fluoro-2-methylpropyl)-3,3-dimethyl-2,3,4,9-tetrahydro-1H-pyrido[3,4-b]indol-1-yl)phenyl)acrylate (racemate) (178 mg, 59.1%) as a beige solid. The racemic product was purified by preparative HPLC (Chiralpak AD column, 20 μm silica, 50 mm diameter, 250 mm length), Heptane:Ethanol: 80:20. Fractions containing the desired compounds were evaporated to dryness to afford (E)-methyl 3-(4-(2-(2-fluoro-2-methylpropyl)-3,3-dimethyl-2,3,4,9-tetrahydro-1H-pyrido[3,4-b]indol-1-yl)phenyl)acrylate (isomer 1, first eluted, 70 mg) and (E)-methyl 3-(4-(2-(2-fluoro-2-methylpropyl)-3,3-dimethyl-2,3,4,9-tetrahydro-1H-pyrido[3,4-b]indol-1-yl)phenyl)acrylate (isomer 2, second eluted, 66 mg). $^1$H NMR (400 MHz, CDCl$_3$, 30° C.) δ 1.00 (3H, s), 1.13 (3H, d), 1.20 (3H, s), 1.44 (3H, d), 2.57-2.78 (3H, m), 2.93 (1H, dd), 3.80 (3H, s), 5.05 (1H, s), 6.41 (1H, d), 7.13 (1H, ddd), 7.18 (1H, ddd), 7.32 (1H, d), 7.43 (2H, d), 7.51 (2H, d), 7.54 (1H, d), 7.64 (1H, s), 7.67 (1H, d). m/z: ES+ [M+H]+ 435.

Example 9

(E)-3-(3-fluoro-4-(2-((S)-3-fluoro-2-methylpropyl)-3,3-dimethyl-2,3,4,9-tetrahydro-1H-pyrido[3,4-b]indol-1-yl)phenyl)acrylic acid (isomer 1)*

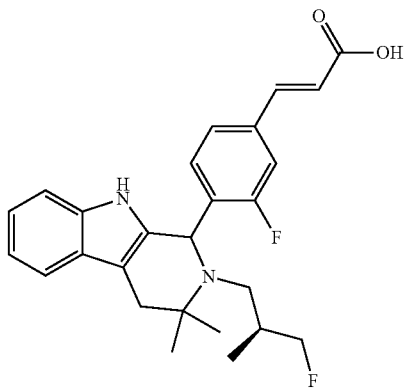 [SMILES: C[C@H](CF)CN1C(c2ccc(/C=C/C(=O)O)cc2F)c2[nH]c3ccccc3c2CC1(C)C]

2M Sodium hydroxide (3.31 ml, 6.63 mmol) was added to a solution of (E)-methyl 3-(3-fluoro-4-(2-((S)-3-fluoro-2-methylpropyl)-3,3-dimethyl-2,3,4,9-tetrahydro-1H-pyrido[3,4-b]indol-1-yl)phenyl)acrylate (600 mg, 1.33 mmol) (mixture of diastereoisomers) in methanol (5 ml), and THF (20 ml) and the mixture stirred at ambient temperature for 4 hours. The mixture was concentrated to a volume such that all of the organic solvent had been removed, diluted with water (50 ml), acidified with dilute HCl to pH 6 and extracted with ethyl acetate (2×50 ml). The extracts were combined and evaporated under reduced pressure. The residue was purified by preparative HPLC (Chiralpak IA column, 20 μm silica, 20 mm diameter, 250 mm length), Heptane:IPA 90:10, 0.2% acetic acid at 80 ml/min. Fractions containing the desired compounds were combined and analysed to yield (E)-3-(3-fluoro-4-(2-((S)-3-fluoro-2-methylpropyl)-3,3-dimethyl-2,3,4,9-tetrahydro-1H-pyrido[3,4-b]indol-1-yl)phenyl)acrylic acid (isomer 1, first eluted, 130 mg, 22.36%) and (E)-3-(3-fluoro-4-(2-((S)-3-fluoro-2-methylpropyl)-3,3-dimethyl-2,3,4,9-tetrahydro-1H-pyrido[3,4-b]indol-1-yl)phenyl)acrylic acid (isomer 2, second eluted, 30.0 mg, 5.16%).

$^1$H NMR (500 MHz, DMSO, 30° C.) δ 0.49 (3H, d), 1.03 (3H, s), 1.14-1.21 (1H, m), 1.28 (3H, s), 2.17 (1H, dd), 2.59-2.71 (1H, m), 2.8-2.99 (2H, m), 4.09-4.34 (2H, m), 4.99 (1H, s), 6.59 (1H, d), 6.86-7.07 (2H, m), 7.1-7.19 (1H, m), 7.18-7.29 (1H, m), 7.36-7.49 (2H, m), 7.49-7.66 (2H, m), 10.31 (1H, s), $CO_2H$ not observed. m/z: ES+ [M+H]+ 439.

* Stereochemistry inferred to be (R) at the undefined centre by analogy with other examples.

The (E)-methyl 3-(3-fluoro-4-(2-((S)-3-fluoro-2-methylpropyl)-3,3-dimethyl-2,3,4,9-tetrahydro-1H-pyrido[3,4-b]indol-1-yl)phenyl)acrylate (mixture of diastereomers) used as starting material was prepared as follows:—

Preparation of (E)-methyl 3-(3-fluoro-4-formylphenyl)acrylate

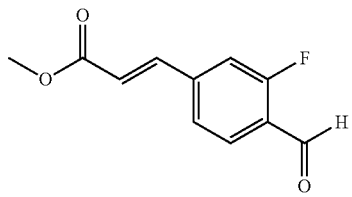

4-Bromo-2-fluorobenzaldehyde (20.88 g, 102.87 mmol) and methyl acrylate (13.98 ml, 154.30 mmol) were taken up in thoroughly degassed DMA (150 ml) and tri-o-tolylphosphine (3.13 g, 10.29 mmol), palladium(II) acetate (1.155 g, 5.14 mmol) and triethylamine (28.7 ml, 205.74 mmol) added. The reaction was stirred and heated to 100° C. for 16 hours. More tri-o-tolylphosphine (3.13 g, 10.29 mmol) and palladium(II) acetate (1.155 g, 5.14 mmol) were added and the reaction mixture was heated to 110° C. for a further 2 hours. Water (1 L) was added and the reaction mixture extracted with DCM (2×500 ml). Combined organics were dried (MgSO$_4$), filtered and evaporated to give a brown solid. The crude product was purified by flash silica chromatography, elution gradient 0 to 25% EtOAc in heptane. Pure fractions were evaporated to dryness to afford (E)-methyl 3-(3-fluoro-4-formylphenyl)acrylate (15.20 g, 71.0%) as a yellow solid.

$^1$H NMR (400 MHz, CDCl$_3$, 30° C.) δ 3.83 (3H, s), 6.53 (1H, d), 7.31 (1H, dd), 7.41 (1H, d), 7.65 (1H, d), 7.79-8 (1H, m), 10.25-10.41 (1H, m). No mass ion observed in LCMS.

Preparation of (E)-methyl 3-(4-(3,3-dimethyl-2,3,4,9-tetrahydro-1H-pyrido[3,4-b]indol-1-yl)-3-fluorophenyl)acrylate (racemate)

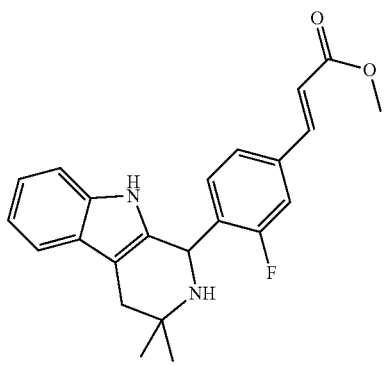 [SMILES: COC(=O)/C=C/c1ccc(C2NC(C)(C)Cc3c2[nH]c2ccccc32)c(F)c1]

1-(1H-Indol-3-yl)-2-methylpropan-2-amine (1 g, 5.31 mmol) and (E)-methyl 3-(3-fluoro-4-formylphenyl)acrylate (1.106 g, 5.31 mmol) in acetic acid (15 ml) were stirred at 80° C. for 2 hours under nitrogen. The crude product was purified by ion exchange chromatography, using an SCX-2 column. The desired product was eluted from the column using 7M NH$_3$/methanol and pure fractions were evaporated to dryness to afford (E)-methyl 3-(4-(3,3-dimethyl-2,3,4,9-tetrahydro-1H-pyrido[3,4-b]indol-1-yl)-3-fluorophenyl)acrylate (racemate) (2.000 g, 99%). $^1$H NMR (400 MHz, DMSO, 30° C.) δ 1.14 (3H, s), 1.27 (3H, s), 2.52-2.74 (2H, m), 3.74 (3H, s), 5.12 (1H, s), 6.69 (1H, d), 6.86-7.05 (2H, m), 7.20 (1H, d), 7.25-7.33 (2H, m), 7.39 (1H, d), 7.73 (1H, d), 7.85 (1H, t), 10.29 (1H, s), NH not observed. m/z: ES+ [M+H]+ 379.

Preparation of (E)-methyl 3-(3-fluoro-4-(2-((S)-3-fluoro-2-methylpropyl)-3,3-dimethyl-2,3,4,9-tetrahydro-1H-pyrido[3,4-b]indol-1-yl)phenyl)acrylate (mixture of diastereomers)

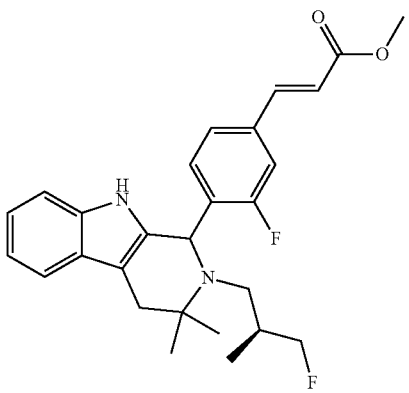 [SMILES: COC(=O)/C=C/c1ccc(C2c3[nH]c4ccccc4c3CC(C)(C)N2C[C@H](C)CF)c(F)c1]

(S)-3-Fluoro-2-methylpropyl trifluoromethanesulfonate (obtained as described in Example 3, preparation of starting materials) (1.259 g, 5.62 mmol) was added to a solution of (E)-methyl 3-(4-(3,3-dimethyl-2,3,4,9-tetrahydro-1H-pyrido[3,4-b]indol-1-yl)-3-fluorophenyl)acrylate (racemate) (850 mg, 2.25 mmol) and N-ethyl-N-isopropylpropan-2-amine (1.467 ml, 8.42 mmol) in 1,4-dioxane (5 ml). The mixture was heated at 60° C. for 4 hours, then stirred at ambient temperature for 12 hours. The mixture was partitioned between ethyl acetate (25 ml) and water (25 ml). The aqueous layer was extracted with ethyl acetate (2×25 ml) and the extracts combined with the organic layer. The combined extracts were evaporated under vacuum. The residue was purified by flash silica chromatography, elution solvent 10% EtOAc in heptane. Pure fractions were evaporated to dryness to afford (E)-methyl 3-(3-fluoro-4-(2-((S)-3-fluoro-2-methylpropyl)-3,3-dimethyl-2,3,4,9-tetrahydro-1H-pyrido[3,4-b]indol-1-yl)phenyl)acrylate (mixture of diastereoisomers) (600 mg, 59.0%). m/z: ES+ [M+H]+ 453.

Example 10

(E)-3-[4-[(1R,3R)-1-deuterio-2-(2-fluoro-2-methyl-propyl)-3-methyl-4,9-dihydro-3H-pyrido[3,4-b]indol-1-yl]-3,5-difluoro-phenyl]prop-2-enoic acid

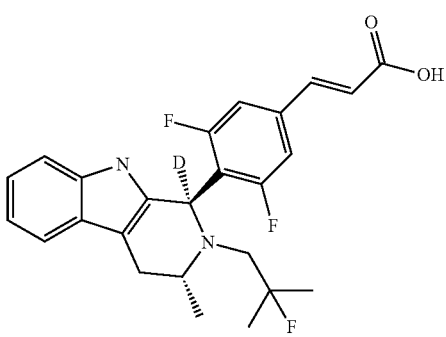 [SMILES: [2H][C@@]1(c2c(F)cc(/C=C/C(=O)O)cc2F)c2[nH]c3ccccc3c2C[C@@H](C)N1CC(C)(C)F]

Methyl (E)-3-[4-[(1R,3R)-1-deuterio-2-(2-fluoro-2-methyl-propyl)-3-methyl-4,9-dihydro-3H-pyrido[3,4-b]indol-1-yl]-3,5-difluoro-phenyl]prop-2-enoate (4.70 g, 10.27 mmol) was dissolved in iPrOH (42.8 ml) and 5M sodium hydroxide solution (6.16 ml, 30.82 mmol) was added in one portion, the reaction was then stirred at room temperature for 4 hours. Water was added (100 ml) and the pH was brought to ~5 by addition of 2N HCl. The solution was extracted with EtOAc (×2) and the combined organics were dried (MgSO$_4$) and concentrated in vacuo. The residue was passed through a silica plug, eluting first with DCM, then up to 5% MeOH in DCM. Fractions containing product were evaporated to a yellow solid (~4.2 g). The residue (4.2 g) was dissolved in EtOH (20 ml) and warmed to 35° C. Water (30 ml) was added slowly over ~40 mins. The mixture was then stirred for another 30 minutes, then slowly cooled to room temperature. Additional water (30 ml) was added, and the reaction was then cooled to 0° C. The mixture was filtered and the solids were washed with water before being dried under vacuum at 35° C. overnight to afford (E)-3-[4-[(1R,3R)-1-deuterio-2-(2-fluoro-2-methyl-propyl)-3-methyl-4,9-dihydro-3H-pyrido[3,4-b]indol-1-yl]-3,5-difluoro-phenyl]prop-2-enoic acid (3.34 g, 73.3%) as a pale yellow solid. $^1$H NMR (400 MHz, CDCl$_3$, 30° C.) 1.12 (3H, d), 1.19 (3H, d), 1.26 (3H, d), 2.43 (1H, dd), 2.63 (1H, dd), 2.87 (1H, dd), 3.07 (1H, dd), 3.65 (1H, q), 6.41 (1H, d), 7.02 (2H, d), 7.06-7.16 (2H, m), 7.19-7.25 (1H, m), 7.41 (1H, s), 7.48-7.57 (1H, m), 7.63 (1H, d), CO$_2$H not observed. m/z: ES+ [M+H]+ 444.

This compound could alternatively be named (E)-3-[4-[(1R,3R)-1-deuterio-2-(2-fluoro-2-methyl-propyl)-3-methyl-4,9-dihydro-3H-pyrido[3,4-b]indol-1-yl]-3,5-difluoro-phenyl]acrylic acid.

Preparation of (4-bromo-2,6-difluoro-phenyl)-dideuterio-methanol

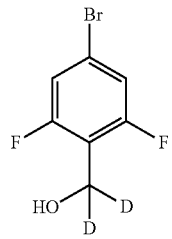 [SMILES: [2H]C([2H])(O)c1c(F)cc(Br)cc1F]

Lithium borodeuteride (0.497 g, 17.25 mmol) was added portionwise to a solution of methyl 4-bromo-2,6-difluorobenzoate (2.89 g, 11.5 mmol) in THF (46.0 ml). The reaction was heated to 50° C. for 2 hours. After cooling, (30 ml) 2N HCl was carefully added. The layers were separated, and the aqueous was extracted with EtOAc (2×50 ml). The combined organics were washed with brine, dried (MgSO$_4$) and concentrated to afford (4-bromo-2,6-difluoro-phenyl)-dideuterio-methanol (2.250 g, 87%) as a white solid. $^1$H NMR (400 MHz, CDCl$_3$, 30° C.) 1.96 (1H, s), 7.07-7.13 (2H, m).

Preparation of 4-bromo-2,6-difluoro-1-deuterobenzaldehyde

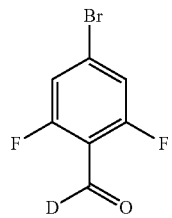 [SMILES: [2H]C(=O)c1c(F)cc(Br)cc1F]

Dess-Martin reagent (4.98 g, 11.73 mmol) was added to (4-bromo-2,6-difluoro-phenyl)-dideuterio-methanol (2.20 g, 9.78 mmol) in DCM (39.1 ml) at room temperature. The reaction was stirred for 1 hour, then was quenched by addition of (50 ml) sat. NaHCO$_3$ containing 10% sodium thiosulfate. The layers were separated and the aqueous phase was extracted with DCM (2×50 ml). The organics were dried (MgSO$_4$) and concentrated, then the crude product was purified by flash silica chromatography, elution gradient 0 to 25% EtOAc in heptane. Pure fractions were evaporated to dryness to afford 4-bromo-2,6-difluoro-1-deuterobenzaldehyde (2.040 g, 94%) as a white solid. $^1$H NMR (400 MHz, CDCl$_3$, 30° C.) 7.18-7.25 (2H, m). No mass ion observed.

Preparation of methyl (E)-3-(4-deuteriocarbonyl-3,5-difluoro-phenyl)prop-2-enoate

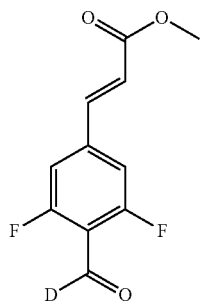 [SMILES: [2H]C(=O)c1c(F)cc(/C=C/C(=O)OC)cc1F]

4-Bromo-2,6-difluoro-1-deuterobenzaldehyde (3.33 g, 15.0 mmol), triethylamine (4.18 ml, 30.00 mmol), palladium (II) acetate (0.168 g, 0.75 mmol) and tritolylphosphine (0.457 g, 1.50 mmol) were dissolved in DMF (36.6 ml), which was degassed. Methyl acrylate (2.026 ml, 22.50 mmol) was then added and the reaction was heated to 80° C. for 4 hours. After cooling, the mixture was added to water (150 ml) and extracted with EtOAc (2×150 ml). The combined organics were washed with 2N HCl (100 ml) then brine (100 ml), then dried (MgSO$_4$) and concentrated. The crude product was purified by flash silica chromatography, elution gradient 0 to 40% EtOAc in heptane. Pure fractions were evaporated to dryness to afford methyl (E)-3-(4-deuteriocarbonyl-3,5-difluoro-phenyl)prop-2-enoate (2.93 g, 86%) as a yellow solid. 1H NMR (400 MHz, CDCl$_3$, 30° C.) 3.83 (3H, d), 6.51 (1H, d), 7.12 (2H, m), 7.57 (1H, d). m/z (ES+), [M+H]+=228.

(R)—N-(1-(1H-indol-3-yl)propan-2-yl)-2-fluoro-2-methylpropan-1-amine

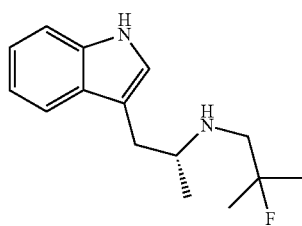 [SMILES: C[C@H](Cc1c[nH]c2ccccc12)NCC(C)(C)F]

(2R)-1-(1H-indol-3-yl)propan-2-amine (3.81 kg, 21.21 moles) was added to a 100 L glass lined jacketed vessel under an atmosphere of nitrogen. 1,4-dioxane (23 L) was added, and the agitator was switched on. Diisopropylethylamine (5.55 L; 31.82 moles) was added to the stirred suspension followed by (2-fluoro-2-methyl-propyl)trifluoromethanesulfonate (5.55 kg, 23.77 moles). 1,4-Dioxane (4 L) was added to the vessel, and the mixture was heated to 75° C. Heating was continued for 24 hours before cooling the mixture to 25° C. Water (30.5 L) was added to the vessel, followed by toluene (30.5 L). After 40 minutes the agitator was switched off and the layers were allowed to separate. The aqueous layer was removed and water (30.5 L) was added to the organic solution. The mixture was agitated for 15 minutes before allowing the layers to separate. The aqueous layer was removed from the vessel. The organic solution was concentrated by vacuum distillation (jacket temperature 65° C., 110 mbar pressure) until approximately 27 L of distillate had been removed. The remaining solution in the vessel was cooled to afford (R)—N-(1-(1H-indol-3-yl)propan-2-yl)-2-fluoro-2-methylpropan-1-amine as a solution in toluene (33% w/w) (15.4 Kg, 97%). 1H NMR (500 MHz, DMSO, 27° C.) 0.98 (3H, d), 1.26 (3H, d), 1.30 (3H, d), 2.57-2.75 (3H, m), 2.81 (1H, dd), 2.84-2.92 (1H, m), 6.97 (1H, t), 7.06 (1H, t), 7.11-7.22 (1H, multiplet obscured by toluene signals), 7.34 (1H, d), 7.52 (1H, d), 10.80 (1H, s).

Preparation of methyl (E)-3-[4-1[(1R,3R)-1-deuterio-2-(2-fluoro-2-methyl-propyl)-3-methyl-4,9-dihydro-3H-pyrido[3,4-b]indol-1-yl]-3,5-difluoro-phenyl]prop-2-enoate

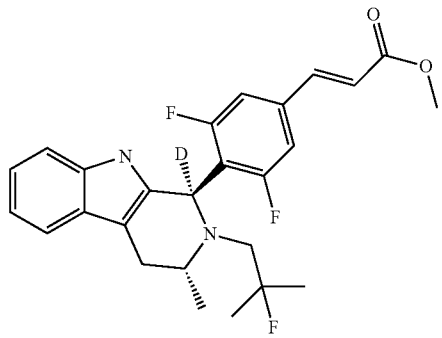 [SMILES: [2H][C@@]1(c2c(F)cc(/C=C/C(=O)OC)cc2F)c2[nH]c3ccccc3c2C[C@@H](C)N1CC(C)(C)F]

(R)—N-(1-(1H-indol-3-yl)propan-2-yl)-2-fluoro-2-methylpropan-1-amine [33% w/w in toluene] (11.26 g, 14.97 mmol) and (E)-3-(4-deuteriocarbonyl-3,5-difluoro-phenyl)prop-2-enoate (3.40 g, 14.97 mmol) were heated in toluene (55.6 ml)/acetic acid (4.28 ml, 74.83 mmol) at 80° C. for 5 hr. After cooling, the volatiles were removed under vacuum. The residue was taken-up in DCM (200 ml) and washed with sat. NaHCO$_3$ solution (200 ml). The aqueous phase was extracted with DCM (100 ml) then the combined organics were washed with brine, dried and concentrated in vacuo. The crude material was loaded to an SCX-2 column, eluting with methanol to remove unreacted aldehyde. The column was then eluted with 7M NH$_3$-MeOH to liberate the product. The basic filtrate was evaporated and the crude product was purified by flash silica chromatography, elution gradient 0 to 40% EtOAc in heptane. Pure fractions were evaporated to dryness to afford methyl (E)-3-[4-[(1R,3R)-1-deuterio-2-(2-fluoro-2-methyl-propyl)-3-methyl-4,9-dihydro-3H-pyrido[3,4-b]indol-1-yl]-3,5-difluoro-phenyl]prop-2-enoate (4.70 g, 68.6%) as a pale yellow solid.

$^1$H NMR (400 MHz, CDCl$_3$, 30° C.) 1.11 (3H, d), 1.19 (3H, d), 1.25 (3H, d), 2.42 (1H, dd), 2.62 (1H, dd), 2.87 (1H, dd), 3.07 (1H, dd), 3.65 (1H, q), 3.81 (3H, s), 6.39 (1H, d), 6.99 (2H, d), 7.06-7.17 (2H, m), 7.23 (1H, dd), 7.45 (1H, s), 7.49-7.6 (2H, m). m/z: ES+[M+H]+ 458.

Example 11

Preparation of (1R,3R)-1-{4-[(E)-2-carboxyethenyl]-2,6-difluorophenyl}-2-(2-fluoro-2-methylpropyl)-3-methyl-2,3,4,9-tetrahydro-1H-beta-carbolin-2-ium maleate

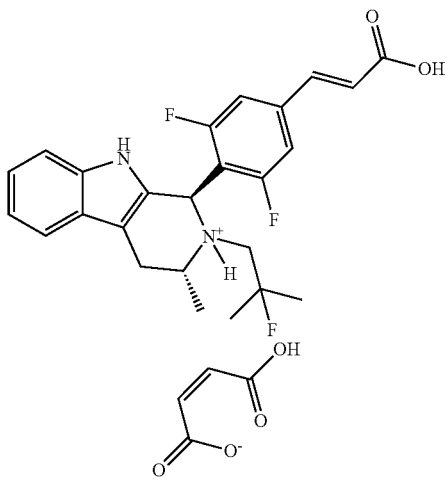

A solution of maleic acid (1.31 g, 11.29 mmol) in acetone (15 ml) was stirred under nitrogen. A solution of (E)-3-(3,5-difluoro-4-((1R,3R)-2-(2-fluoro-2-methylpropyl)-3-methyl-2,3,4,9-tetrahydro-1H-pyrido[3,4-b]indol-1-yl)phenyl)acrylic acid (Example 1) (5.00 g, 11.3 mmol) in acetone (25 ml) was added to the maleic acid solution to give a yellow solution. The reaction vessel was covered in foil to protect from light and purged with a stream of nitrogen gas overnight until the solvent evaporated. A solid was obtained which was dried in vacuo for 2 hours to give the title compound as a cream solid (6.23 g, 98%). $^1$H NMR (500 MHz, DMSO, 27° C.) 0.95-1.34 (9H, m), 2.24-2.45 (1H, m), 2.54-2.66 (1H, m), 2.8-2.99 (2H, m), 3.52 (1H, s), 5.22 (1H, s), 6.26 (2H, s), 6.67 (1H, d), 6.89-7.07 (2H, m), 7.19 (1H, d), 7.39-7.51 (3H, m), 7.55 (1H, d), 10.59 (1H, s).

Figure 8:
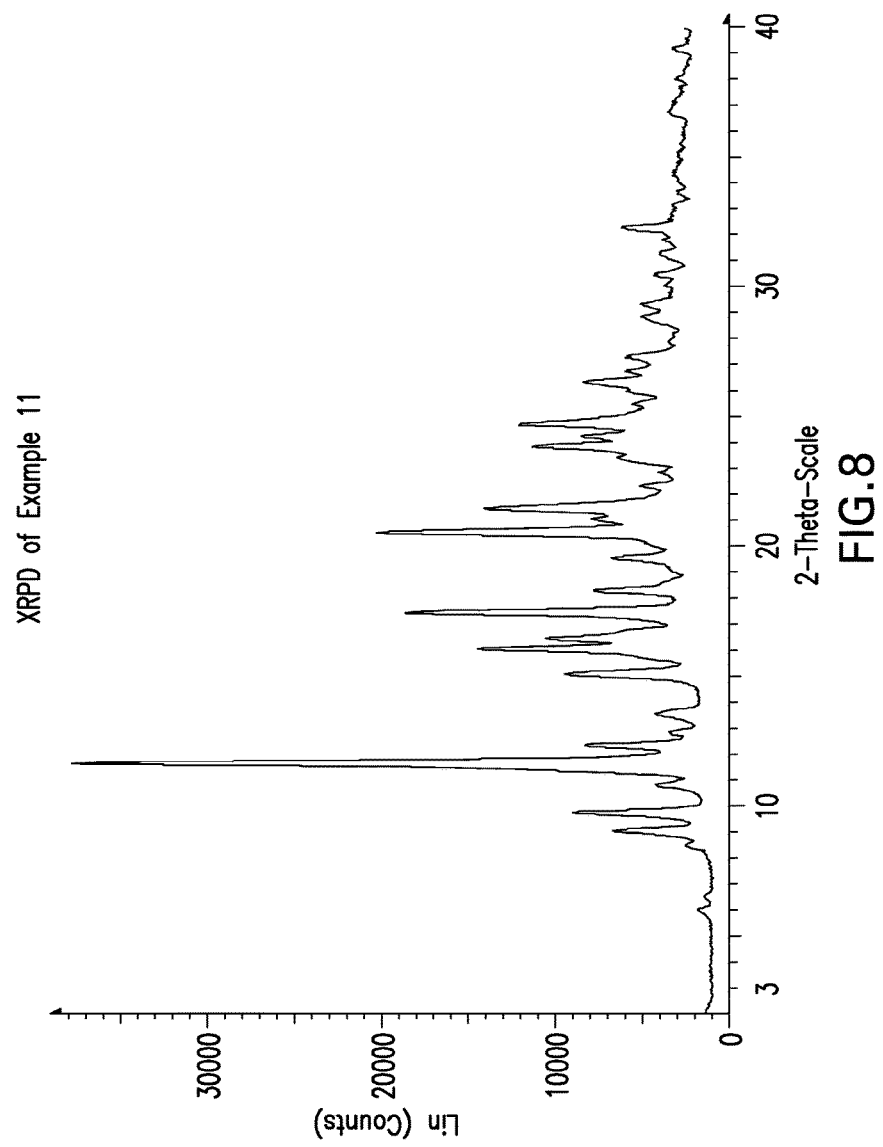
FIG. 8 shows an X-Ray Powder Diffraction Pattern of Example 11
Figure 9:
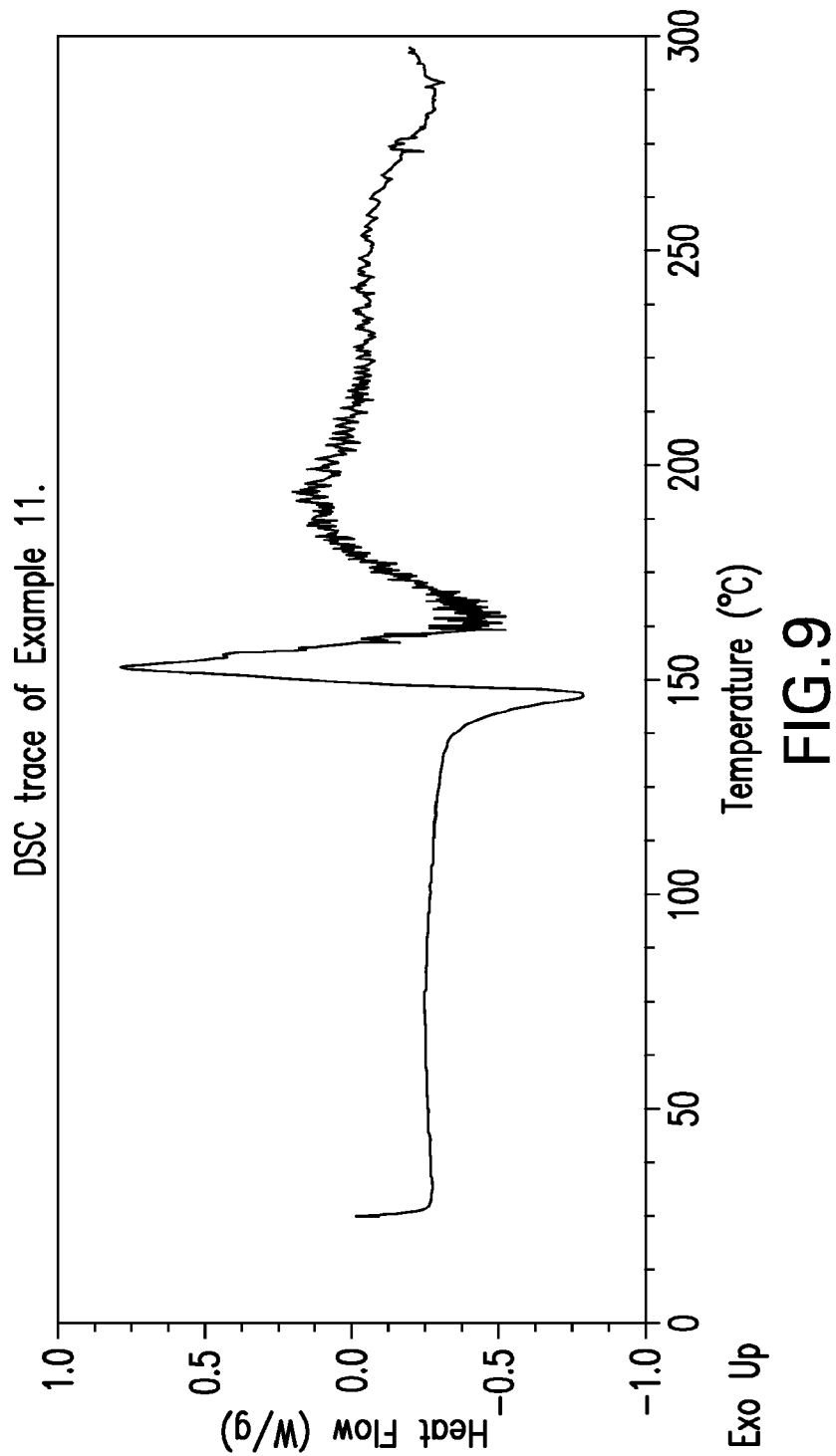
FIG. 9 shows a DSC trace of Example 11.
Figure 10:
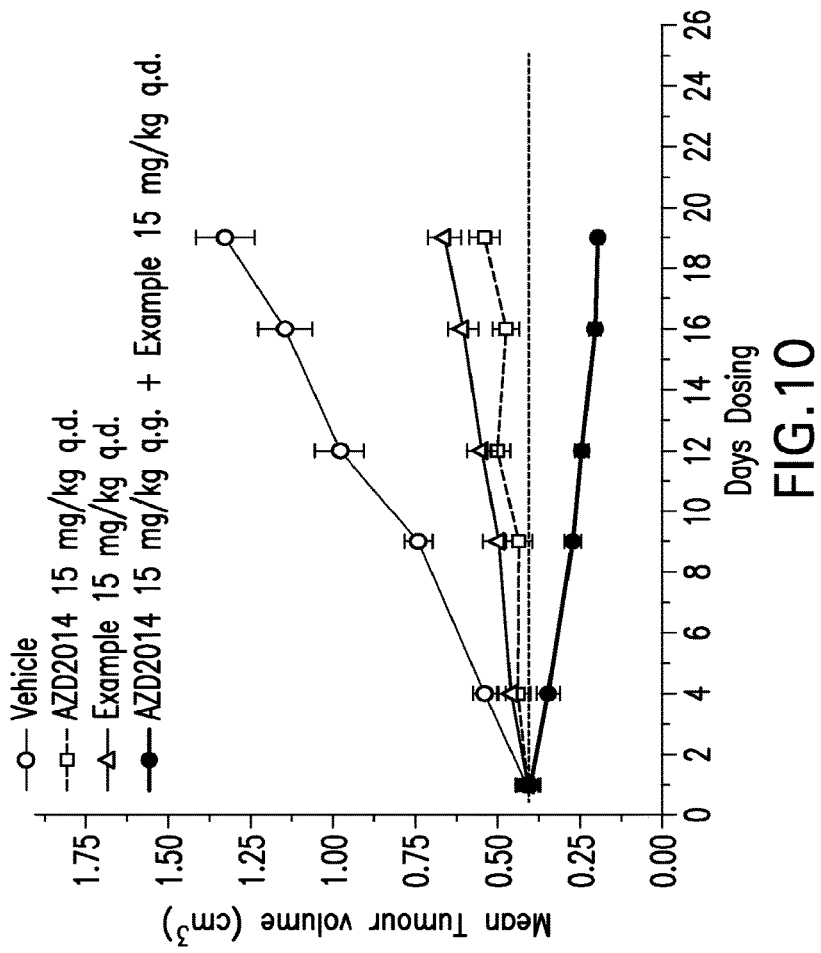
FIG. 10 shows the results of an MCF-7 xenograft study with Example 1 and AZD2014.
Figure 11:
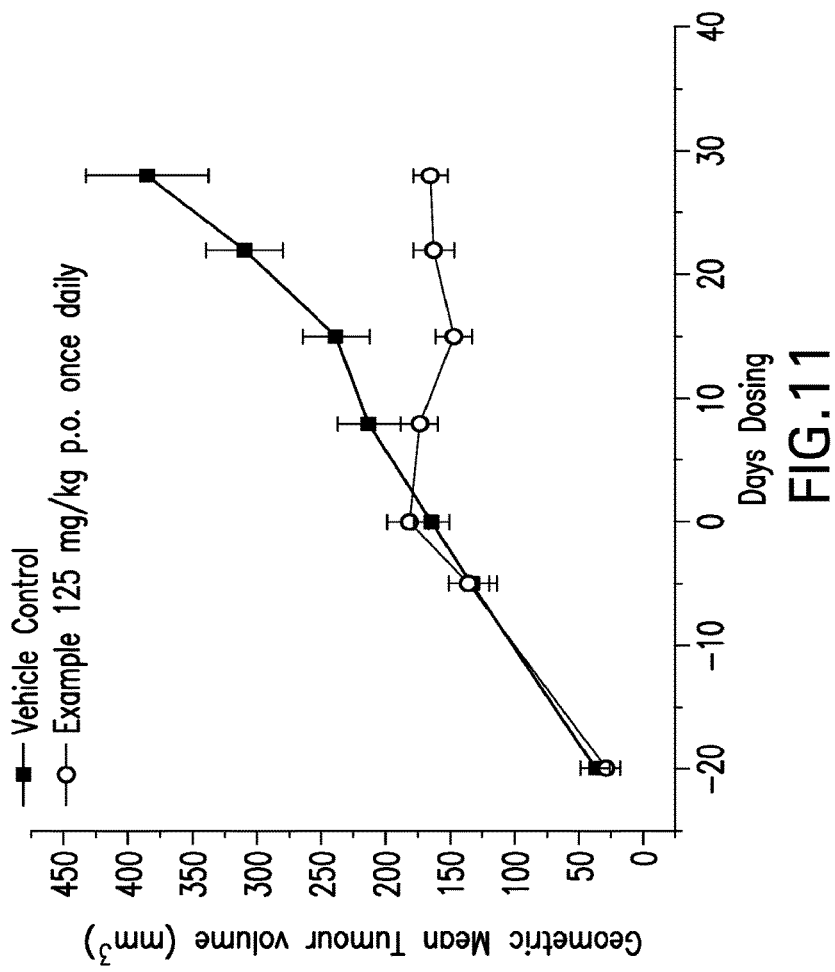

An XRPD trace of this maleate salt is shown in FIG. 8 and a DSC trace shown in FIG. 9.

Example 12

Exemplary compositions of Example 1 were manufactured at the 75 g scale using a wet granulation process. The active ingredient, mannitol, microcrystalline cellulose and sodium starch glycolate were weighed in the quantities tabulated below and transferred to a Diosna P1-6 mixer-granulator and mixed (with chopping) at 600 rpm for 6 minutes. For Composition A, mixing was continued while 30 mL water was added in two aliquots at a rate of approximately 1 mL per second, pausing mixing in between aliquots, while for Composition B a solution prepared by stirring the required amounts of EDTA and ascorbic acid with 20 mL water at 50° C. for 20 minutes (protected from light) was added using an analogous process, the second aliquot in this case comprising approximately 10 mL of rinse liquor. Wet mixing was continued for a total of 1.5 minutes. The wet granules were passed through a 1.5 mm screen then dried under vacuum at 50-60° C. to a moisture content of <2% w/w. The resulting granules were milled using a 1 mm screen then mixed with the lubricant for 5 minutes at 32 rpm using a Turbula blender. Tablets containing 10 mg of the active ingredient were formed by compressing the granules to a nominal 100 mg compression weight using a Riva Mini-press equipped with 6 mm normal concave tooling.

| Component | Function | Composition A % w/w | Composition A Amount (g) | Composition B % w/w | Composition B Amount (g) |
|---|---|---|---|---|---|
| Example 1 Form B | Active ingredient | 10.0 | 7.50 | 10.0 | 7.50 |
| EDTA | Chelating agent | Not present | | 0.1 | 0.075 |
| Ascorbic acid | Anti-oxidant | Not present | | 0.5 | 0.375 |
| Mannitol | Diluent | 68.0 | 51.00 | 67.4 | 50.55 |
| Microcrystalline cellulose | Diluent | 15.0 | 11.25 | 15.0 | 11.25 |
| Sodium starch glycolate | Disintegrant | 5.0 | 3.75 | 5.0 | 3.75 |
| Stearic acid | Lubricant | 2.0 | 1.50 | 2.0 | 1.50 |
| Total | | 100 | 75.00 | 100 | 75.00 |

The stability of Compositions A and B with regard to degradant formation (wherein "degradant" means (R,E)-3-(3,5-difluoro-4-(2-(2-fluoro-2-methylpropyl)-3-methyl-4,9-dihydro-3H-pyrido[3,4-b]indol-2-ium-1-yl)phenyl)acrylate) was evaluated for tablets packed in induction sealed 75 cc HDPE bottles or exposed to the atmosphere in petri dishes, stored in the dark, under controlled temperature and humidity as tabulated below. It is apparent that Composition B, which contains both a chelating agent and anti-oxidant, is more stable to chemical degradation than Composition A which is a standard tablet formulation.

Stability of exemplary compositions with regard to Degradant formation (%)

| Formulation | Initial Time Point | 4 Week Time Point (storage condition) (5° C., packed) | (25° C./ 60% RH, packed) | (25° C./ 60% RH, exposed) | (40° C./ 75% RH, exposed) |
|---|---|---|---|---|---|
| Composition A | 0.05 | 0.06 | 0.08 | 0.27 | 0.28 |
| Composition B | ND | <0.05 | <0.05 | 0.05 | 0.11 |

ND Not detected (<0.02% w/w)

Example 13

(E)-3-[3,5-difluoro-4-[(3R)-2-(2-fluoro-2-methyl-propyl)-3-methyl-4,9-dihydro-3H-pyrido[3,4-b]indol-2-ium-1-yl]phenyl]prop-2-enoate

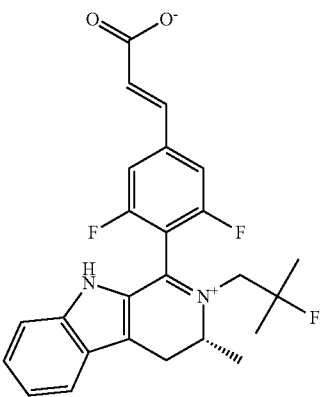 [SMILES: C[C@@H]1Cc2c([nH]c3ccccc23)C(c2c(F)cc(/C=C/C(=O)[O-])cc2F)=[N+]1CC(C)(C)F]

(E)-3-(3,5-Difluoro-4-((1R,3R)-2-(2-fluoro-2-methylpropyl)-3-methyl-2,3,4,9-tetrahydro-1H-pyrido[3,4-b]indol-1-yl)phenyl)acrylic acid (200 mg, 0.45 mmol) was added to a solution of cerium ammonium nitrate (248 mg, 0.45 mmol) in acetonitrile (6 ml)/water (1.500 ml) at room temperature. The reaction was stirred for 2 hr and further cerium ammonium nitrate (248 mg, 0.45 mmol) was added. The solution was stirred at 25° C. for a further 15 minutes. The reaction mixture was acidified with 2M HCl (3 ml) and extracted with DCM (2×10 ml). The organics were then concentrated in vacuo and the crude product was purified by preparative HPLC (Waters SunFire column, 5. silica, 50 mm diameter, 100 mm length), using decreasingly polar mixtures of water (containing 0.1% formic acid) and MeCN as eluents. Fractions containing the desired compound were evaporated to dryness to afford (R,E)-3-(3,5-difluoro-4-(2-(2-fluoro-2-methylpropyl)-3-methyl-4,9-dihydro-3H-pyrido[3,4-b]indol-2-ium-1-yl)phenyl)acrylate (35.0 mg, 17.58%) as an orange glass. 1H NMR (500 MHz, DMSO, 30° C.) 1.27 (3H, d), 1.43-1.55 (6H, m), 3.51 (1H, d), 3.72 (1H, dd), 3.96 (1H, dd), 4.18-4.32 (1H, m), 4.67 (1H, s), 6.59 (1H, s), 7.09-7.3 (2H, m), 7.42 (1H, t), 7.52-7.73 (3H, m), 7.78 (1H, d), NH not observed. HRMS (ESI): [M+H]$^+$, found 441.17831, $C_{23}H_{24}F_2N_2O_2$ requires 441.17844.

Preparation of (E)-3-[3,5-difluoro-4-[2-(2-fluoro-2-methyl-propyl)-3-methyl-9H-pyrido[3,4-b]indol-2-ium-1-yl]phenyl]prop-2-enoate

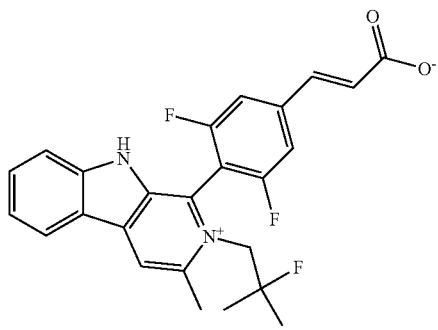 [SMILES: Cc1cc2c([nH]c3ccccc32)c(-c2c(F)cc(/C=C/C(=O)[O-])cc2F)[n+]1CC(C)(C)F]

(E)-3-(3,5-Difluoro-4-((1R,3R)-2-(2-fluoro-2-methylpropyl)-3-methyl-2,3,4,9-tetrahydro-1H-pyrido[3,4-b]indol-1-yl)phenyl)acrylic acid (0.500 g, 1.13 mmol) was dissolved in DMSO (10 mL) and heated to 120° C. in air and light for 16 h. The reaction was then heated to 180° C. for 2.5 h. The reaction mixture was cooled and purified by preparative HPLC (Waters XBridge Prep C18 OBD column, 5 μ silica, 50 mm diameter, 100 mm length), using decreasingly polar mixtures of water (containing 1% NH$_3$) and MeCN as eluents. Fractions containing the desired compound were evaporated to dryness to afford (E)-3-[3,5-difluoro-4-[2-(2-fluoro-2-methyl-propyl)-3-methyl-9H-pyrido[3,4-b]indol-2-ium-1-yl]phenyl]prop-2-enoate (0.047 g, 9.40%) as an orange solid. 1H NMR (400 MHz, DMSO, 27° C.) 1.27 (3H, s), 1.33 (3H, d), 3.09 (3H, s), 4.59-4.8 (1H, m), 5.14-5.37 (1H, m), 6.54 (1H, d), 7.19 (1H, d), 7.39 (1H, t), 7.63 (2H, d), 7.74 (1H, t), 7.91 (1H, d), 8.45 (1H, d), 8.88 (1H, s), 10.79 (1H, s). m/z: ES+ [M+H]+ 439.

Example 14A

Preparation of (E)-3-[3,5-difluoro-4-[(1R,3R)-2-(2-fluoro-3-hydroxy-2-methyl-propyl)-3-methyl-1,3,4,9-tetrahydropyrido[3,4-b]indol-1-yl]phenyl]prop-2-enoic acid (Isomer 1)

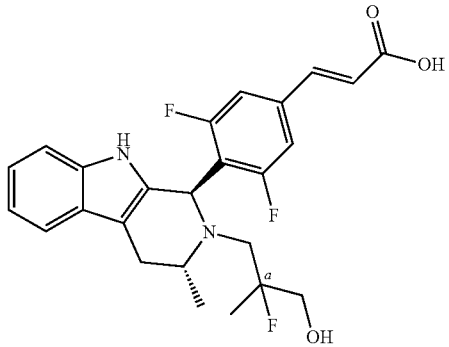

a = unknown absolute
ISOMER 1

2M Sodium hydroxide (1.27 mL, 2.54 mmol) was added to a solution of (E)-methyl 3-(3,5-difluoro-4-((1R,3R)-2-(2-fluoro-3-hydroxy-2-methylpropyl)-3-methyl-2,3,4,9-tetrahydro-1H-pyrido[3,4-b]indol-1-yl)phenyl)acrylate-Isomer 1 (120 mg, 0.25 mmol) in THF (0.635 mL)/methanol (0.635 mL). The reaction was stirred at room temperature for 1 h, then diluted with EtOAc and water. The aqueous was adjusted to pH 6 by addition of 2M HCl, and the layers were separated. The aqueous layer was extracted with EtOAc, then the combined organics were dried (MgSO$_4$) and concentrated in vacuo. The crude product was purified by flash silica chromatography, elution gradient 0 to 10% MeOH in DCM. Pure fractions were evaporated to dryness to afford (E)-3-(3,5-difluoro-4-((1R,3R)-2-(2-fluoro-3-hydroxy-2-methylpropyl)-3-methyl-2,3,4,9-tetrahydro-1H-pyrido[3,4-b]indol-1-yl)phenyl)acrylic acid-Isomer 1 (85 mg, 72.9%) as a beige solid. 1H NMR (400 MHz, DMSO, 27° C.) 0.97 (3H, d), 1.05 (3H, d), 2.32-2.4 (1H, m), 2.44-2.54 (1H, m), 2.73-2.93 (3H, m), 3-3.14 (2H, m), 3.32-3.49 (2H, m), 4.73 (1H, s), 5.14 (1H, s), 6.58 (1H, s), 6.82-6.96 (2H, m), 7.10 (1H, d), 7.33 (1H, d), 7.36 (1H, d), 7.45 (1H, d), 10.49 (1H, s). m/z (ES+), [M+H]+=459.

Example 14B

Preparation of (E)-3-[3,5-difluoro-4-[(1R,3R)-2-(2-fluoro-3-hydroxy-2-methyl-propyl)-3-methyl-1,3,4,9-tetrahydropyrido[3,4-b]indol-1-yl]phenyl]prop-2-enoic acid (Isomer 2)

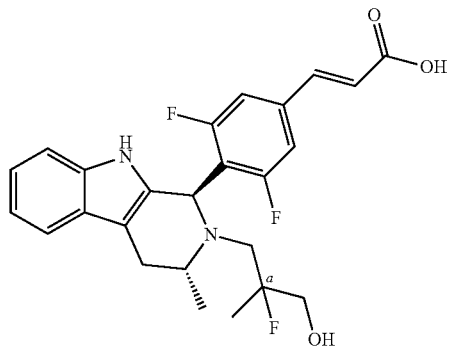

a = unknown absolute
ISOMER 2

2M Sodium hydroxide (1.27 mL, 2.54 mmol) was added to a solution of (E)-methyl 3-(3,5-difluoro-4-((1R,3R)-2-(2-fluoro-3-hydroxy-2-methylpropyl)-3-methyl-2,3,4,9-tetrahydro-1H-pyrido[3,4-b]indol-1-yl)phenyl)acrylate-Isomer 2 (110 mg, 0.23 mmol) in THF (0.529 mL)/methanol (0.529 mL). The reaction was stirred at room temperature for 1 h, then diluted with EtOAc and water. The aqueous was adjusted to pH 6 by addition of 2M HCl, and the layers were separated. The aqueous layer was extracted with EtOAc, then the combined organics were dried (MgSO$_4$) and concentrated in vacuo. The crude product was purified by flash silica chromatography, elution gradient 0 to 10% MeOH in DCM. Pure fractions were evaporated to dryness to afford (E)-3-(3,5-difluoro-4-((1R,3R)-2-(2-fluoro-3-hydroxy-2-methylpropyl)-3-methyl-2,3,4,9-tetrahydro-1H-pyrido[3,4-b]indol-1-yl)phenyl)acrylic acid-Isomer 2 (81 mg, 76%) as a beige solid. 1H NMR (400 MHz, DMSO, 27° C.) 1.02 (2H, s), 1.05 (3H, d), 1.23 (1H, s), 1.90 (3H, s), 2.28-2.46 (1H, m), 2.53-2.7 (1H, m), 2.86-3.03 (2H, m), 3.56 (1H, d), 4.83 (1H, s), 5.17 (1H, s), 6.66 (1H, d), 6.86-7.08 (2H, m), 7.17 (1H, d), 7.40 (1H, d), 7.44 (2H, d), 7.53 (1H, d), 10.54 (1H, s). m/z (ES+), [M+H]+=459.

The (E)-methyl 3-(3,5-difluoro-4-((1R,3R)-2-(2-fluoro-3-hydroxy-2-methylpropyl)-3-methyl-2,3,4,9-tetrahydro-1H-pyrido[3,4-b]indol-1-yl)phenyl)acrylate (Isomer 1 and 2) used as starting materials were prepared as follows:—

2-Fluoro-2-methylpropane-1,3-diol

LiAlH$_4$ (0.741 g, 19.25 mmol) was added portionwise to a cooled solution of diethyl 2-fluoro-2-methylmalonate (1.345 g, 7.00 mmol) in THF (35.0 ml). The reaction was allowed to warm to room temperature over 1 h. After cooling to 0° C., the reaction was quenched by addition of water (0.75 mL), 15% NaOH (0.75 mL), then water (1.5 mL). The suspension was stirred for 30 min, then filtered and the solids were washed with THF. The filtrate was evaporated to afford 2-fluoro-2-methylpropane-1,3-diol (0.745 g, 98%) as a colourless oil. 1H NMR (400 MHz, CDCl$_3$, 27° C.) 1.34 (3H, d), 2.12-2.27 (2H, m), 3.75 (4H, d).

3-(((R)-1-(1H-Indol-3-yl)propan-2-yl)amino)-2-fluoro-2-methylpropan-1-ol

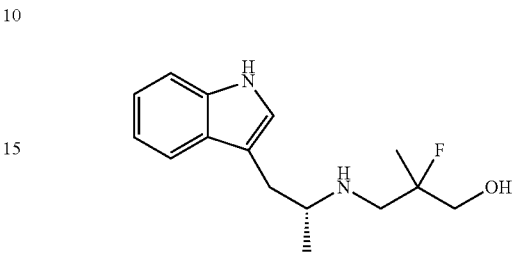

Trifluoromethanesulfonic anhydride (1.151 ml, 6.80 mmol) was added to a solution of 2-fluoro-2-methylpropane-1,3-diol (0.70 g, 6.47 mmol) in DCM (17.85 ml) at 0° C., followed by 2,6-lutidine (0.908 ml, 7.77 mmol). The reaction was allowed to warm to room temperature over 30 min, then was washed with 2M HCl. The organic phase was passed through a phase separator cartridge and concentrated in vacuo. The residue was dissolved in dioxane (12 mL), then (R)-1-(1H-indol-3-yl)propan-2-amine (1.128 g, 6.47 mmol) and DIPEA (1.678 ml, 9.71 mmol) were added and the reaction was heated to 90° C. for 2 h. After cooling, the reaction was diluted with DCM and washed with water. The aqueous was extracted with DCM, then the organics were concentrated in vacuo. The crude product was purified by flash silica chromatography, elution gradient 0 to 10% MeOH in DCM. Pure fractions were evaporated to dryness to afford 3-(((R)-1-(1H-indol-3-yl)propan-2-yl)amino)-2-fluoro-2-methylpropan-1-ol (0.815 g, 47.6%) as a brown gum. m/z (ES+), [M+H]+=265.

(E)-methyl 3-(3,5-difluoro-4-((1R,3R)-2-(2-fluoro-3-hydroxy-2-methylpropyl)-3-methyl-2,3,4,9-tetrahydro-1H-pyrido[3,4-b]indol-1-yl)phenyl)acrylate (Isomer 1 and 2)

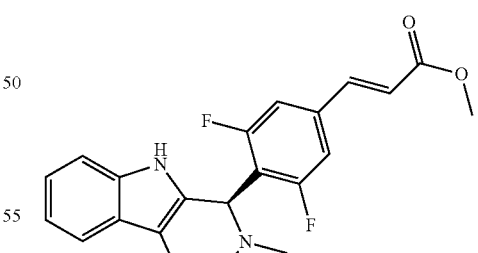

AND
Enantiomer a = unknown absolute
ISOMER 1 and 2

(E)-methyl 3-(3,5-difluoro-4-formylphenyl)acrylate (565 mg, 2.50 mmol) was added to a suspension of 3-(((R)-1-(1H-indol-3-yl)propan-2-yl)amino)-2-fluoro-2-methylpropan-1-ol (661 mg, 2.50 mmol) in toluene (11.3 ml)/acetic acid (1.25 ml). The reaction was heated to 90° C. for 5 h. After cooling, the volatiles were removed under vacuum, then the residue was passed through an SCX-2 column, eluting with methanol to remove unreacted aldehyde. The column was then eluted with $NH_3$/MeOH to liberate the products. The basic filtrate was evaporated then the crude product was purified by flash silica chromatography, elution gradient 0 to 50% EtOAc in heptane. Pure fractions were evaporated to dryness to afford (E)-methyl 3-(3,5-difluoro-4-((1R,3R)-2-(2-fluoro-3-hydroxy-2-methylpropyl)-3-methyl-2,3,4,9-tetrahydro-1H-pyrido[3,4-b]indol-1-yl)phenyl)acrylate (Isomer 1-122 mg, 10.3%) as a yellow solid and (E)-methyl 3-(3,5-difluoro-4-((1R,3R)-2-(2-fluoro-3-hydroxy-2-methylpropyl)-3-methyl-2,3,4,9-tetrahydro-1H-pyrido[3,4-b]indol-1-yl)phenyl)acrylate (Isomer 2-129 mg, 11% as a yellow/orange solid. Isomer 1-1H NMR (400 MHz, $CDCl_3$, 27° C.) 1.10 (3H, d), 1.14 (3H, d), 2.54 (1H, dd), 2.62-2.73 (1H, m), 3.06-3.3 (2H, m), 3.40 (1H, dd), 3.56 (1H, t), 3.80 (3H, s), 3.87-4.08 (1H, m), 4.27 (1H, s), 5.16 (1H, s), 6.37 (1H, d), 7.01 (2H, d), 7.07-7.15 (2H, m), 7.14-7.24 (1H, m), 7.42-7.56 (2H, m), 7.71 (1H, s). m/z (ES+), [M+H]+=473. Isomer 2-1H NMR (400 MHz, CDCl3, 27° C.) 1.15 (3H, d), 1.20 (3H, d), 2.65 (1H, dd), 2.79 (1H, t), 2.93-3.09 (2H, m), 3.57 (1H, dt), 3.70 (1H, dd), 3.78 (3H, s), 4.2-4.67 (1H, m), 5.42 (1H, s), 6.32 (1H, d), 6.94 (2H, d), 7.06-7.15 (2H, m), 7.19-7.27 (2H, m), 7.42 (1H, s), 7.51 (1H, dd), 8.02 (1H, s). m/z (ES+), [M+H]+=473.

Reference Example 1

1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one

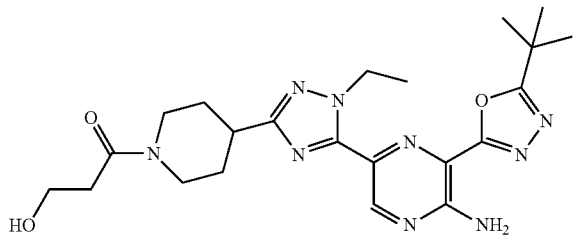 [SMILES: CCn1nc(C2CCN(C(=O)CCO)CC2)nc1-c1cnc(N)c(-c2nnc(C(C)(C)C)o2)n1]

Pyridine 4-methylbenzenesulfonate (11.62 g, 46.24 mmol) was added to a suspension of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-(tetrahydro-2H-pyran-2-yloxy)propan-1-one (128 g, 231.19 mmol) in methanol (1 L) under nitrogen. The mixture was stirred at 60° C. for 1.5 hours. The mixture was soluble after 5 minutes. The mixture was held at 50° C. overnight during which time a precipitate formed. The solid material was isolated by filtration and washed with water and acetonitrile. This material still contained minor impurities from the previous stage and required further purification. The material was dissolved in dichloromethane and purified by flash chromatography on silica gel (0% methanol/DCM to 10% methanol/DCM). The desired product, 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one (Reference Example 1) (92 g, 85%), was thus isolated as a cream solid (Form A): $^1$H NMR Spectrum: (DMSO-$d_6$) 1.4-1.51 (12H, m), 1.51- 1.78 (2H, m), 1.89-2.05 (2H, m), 2.72-2.86 (1H, m), 2.91-3.05 (1H, m), 3.12-3.24 (1H, m), 3.64 (2H, q), 3.83-4.01 (1H, m), 4.29-4.41 (1H, m), 4.47 (1H, t), 4.58 (2H, q), 8.26 (2H, s), 8.85 (1H, s); Mass Spectrum [M+H]+=470.

1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-(tetrahydro-2H-pyran-2-yloxy)propan-1-one was prepared as follows:

1,8-Diazabicyclo[5.4.0]undec-7-ene (76 mL, 511.14 mmol) was added to a suspension of tert-butyl 4-(5-(5-amino-6-(5-tert-butyl-1,3,4-oxadiazol-2-yl)pyrazin-2-yl)-1H-1,2,4-triazol-3-yl)piperidine-1-carboxylate (150 g, 319.46 mmol) in 2-methyl THF (1.2 L). Iodoethane (46 mL, 575.03 mmol) was added and the mixture was stirred for 16 hours at 35° C. Further iodoethane (46 mL, 575.03 mmol) and 1,8-diazabicyclo[5.4.0]undec-7-ene (76 mL, 511.14 mmol) were added and stirring was continued for 24 hours at 35° C. The mixture was poured into water and the insoluble material was isolated by filtration, washed with water and MTBE and dried in vacuo to afford tert-butyl 4-(5-(5-amino-6-(5-tert-butyl-1,3,4-oxadiazol-2-yl)pyrazin-2-yl)-1-ethyl-1H-1,2,4-triazol-3-yl)piperidine-1-carboxylate (116 g, 73.0%) as a yellow solid. The filtrate was extracted with DCM and the organic solution was dried with magnesium sulfate, filtered, and concentrated under reduced pressure. The residue was purified by flash column chromatography on silica using gradient elution (30% MTBE/heptane to 100% MTBE). A second crop of the desired product (12 g, 24.12 mmol, 7.55%), was thus isolated as a yellow solid which was later combined with the first crop: $^1$H NMR Spectrum: (DMSO-$d_6$) 1.41 (9H, s), 1.44 (9H, s), 1.48 (3H, t), 1.52-1.69 (2H, m), 1.87-2.04 (2H, m), 2.79-3.03 (3H, m), 3.86-4.03 (2H, m), 4.59 (2H, q), 7.89 (2H, s), 8.85 (1H, s); Mass Spectrum [M+H]+=498.

A suspension of tert-butyl 4-(5-(5-amino-6-(5-tert-butyl-1,3,4-oxadiazol-2-yl)pyrazin-2-yl)-1-ethyl-1H-1,2,4-triazol-3-yl)piperidine-1-carboxylate (3009.5 g, 6.05 mol) in DCM (9 L) was cooled to 5-10° C. under $N_2$. TFA (9 L) was added portionwise to the suspension whilst maintaining the temperature <30° C. The reaction mixture was stirred at room temperature for 1 h. The mixture was concentrated, the resulting residue was dissolved in water (30 L) and added slowly to a 35% aqueous ammonia solution (12 L) at 0-5° C. The suspension was stirred for 30 min then the product was filtered off and washed with water (2×6 L). The product was dried at 50° C. in vacuo for 2 days. to afford 3-(5-tert-butyl-1,3,4-oxadiazol-2-yl)-5-(1-ethyl-3-(piperidin-4-yl)-1H-1,2,4-triazol-5-yl)pyrazin-2-amine ((2496 g): $^1$H NMR Spectrum: (DMSO-$d_6$) 1.4-1.52 (12H, m), 1.57-1.73 (2H, m), 1.83-1.93 (2H, m), 2.57-2.7 (2H, m), 2.71-2.84 (1H, m), 2.96-3.09 (2H, m), 4.58 (2H, q), 8.06 (2H, s), 8.84 (1H, s); Mass Spectrum [M+H]+=398.

To a solution of 3-(tetrahydro-2H-pyran-2-yloxy) propanoic acid (HATU, 48.80 g 0.2774 mol) and N-ethyl-N-isopropylpropan-2-amine (86.96 mL, 0.4993 mol) in THF (552 mL) was added O-(7-Azabenzotriazol-1-yl)-N,N,N',N'-tetramethyluronium hexafluorophosphate (115.73 g, 0.3051 mol) portionwise at RT under nitrogen. The resulting mixture was stirred for 20 min then 3-(5-tert-butyl-1,3,4-oxadiazol-2-yl)-5-(1-ethyl-3-(piperidin-4-yl)-1H-1,2,4-triazol-5-yl)pyrazin-2-amine (122.5 g (110.25 g active), 0.2774 mol) was added portionwise over 1 h. After 3.5 h, the mixture was concentrated and the residue was slurried in MeCN (275 mL) for 15 min at room temperature. The product was filtered off, washed with MeCN (3×110 mL) and dried overnight at 50° C. in vacuo. This gave 1-(4-(5-(5-amino-6-(5-tert-butyl-1,3,4-oxadiazol-2-yl)pyrazin-2- yl)-1-ethyl-1H-1,2,4-triazol-3-yl)piperidin-1-yl)-3-(tetrahydro-2H-pyran-2-yloxy)propan-1-one (131.9 g, 96%). $^1$H NMR Spectrum: (DMSO-d$_6$) 1.29-1.48 (16H, m), 1.48-1.75 (4H, m), 1.83-1.99 (2H, m), 2.48-2.68 (2H, m), 2.68-2.79 (1H, m), 2.87-2.99 (1H, m), 3.07-3.19 (1H, m), 3.32-3.42 (1H, m), 3.47-3.6 (1H, m), 3.64-3.75 (1H, m), 3.75-3.84 (1H, m), 3.84-3.95 (1H, m), 4.24-4.39 (1H, m), 4.47-4.6 (3H, m), 7.84 (2H, s), 8.79 (1H, s): Mass Spectrum [M+Na]$^+$ =577.

Alternative Preparation of Reference Example 1

To a suspension of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-(tetrahydro-2H-pyran-2-yloxy)propan-1-one (131.9 g, 0.2382 mol) in methanol (1045 mL) was added pyridinium p-toluenesulfonate (11.97 g, 47.7 mmol) under N$_2$. The reaction mixture was stirred at 60° C. for 5.5 h then at 50° C. overnight. The reaction mixture was cooled to 0° C. and the solid was filtered off. The product was slurried in water (250 mL) for 20 min at room temperature, filtered off, washed with water (3×40 mL) and dried at 50° C. in vacuo. This gave 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one (21.4 g) as Form A (see below).

The methanol liquors were concentrated and the resulting solid was slurried in water (0.6 L) for 20 min at room temperature. The solid was isolated by filtration and washed with water (3×100 mL). The filter cake was slurried for a second time in water (0.5 L) for a further 20 minutes. The product was isolated by filtration, washed with water (100 mL) and dried at 50° C. in vacuo. This gave 81.9 g 1-(4-(5-(5-amino-6-(5-tert-butyl-1,3,4-oxadiazol-2-yl) pyrazin-2-yl)-1-ethyl-H-1,2,4-triazol-3-yl)piperidin-1-yl)-3-hydroxypropan-1-one (81.9 g) as Form A.

Both crops were combined (103.3 g), seeded with Form B (16.68 g) and slurried in MeCN (826 mL) at room temperature overnight. This gave 117.4 g of 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one as a pale yellow solid (117.4 g), Form B (see below). This material was further purified by slurrying in heptane (7.5 rel vols) for 1 hour. The mixture was filtered, pulled dry on the filter, and dried at 50° C. in a vacuum oven overnight to afford 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one (102.5 g) as Form B.

Form B may also be made by slurrying Form A in MeCN without seeding.

Form A or B may also be converted to Form C as follows:

A suspension of 1-(4-(5-(5-amino-6-(5-tert-butyl-1,3,4-oxadiazol-2-yl)pyrazin-2-yl)-1-ethyl-1H-1,2,4-triazol-3-yl) piperidin-1-yl)-3-hydroxypropan-1-one (eg Form B made by the processes outlined above) in IPA (12 vol) was heated at reflux until the solid dissolved. The solution was hot filtered then cooled to room temperature. This gave 1-(4-(5-(5-amino-6-(5-tert-butyl-1,3,4-oxadiazol-2-yl)pyrazin-2-yl)-1-ethyl-1H-1,2,4-triazol-3-yl)piperidin-1-yl)-3-hydroxypropan-1-one as a pale yellow solid (99.3 g, 97%) as Form C.

Form C may also be converted to Form B as follows:

In a 10 L flange flask, Form C (377.8 g portion 1) in MIBK (7900 mL) was heated to 110-115° C. to give a solution. The solution was allowed to cool to 97-103° C. and immediately polish filtered into a 50 L vessel containing a seed of Form B (0.8 g) in acetonitrile (8220 mL) stirring at −15° C. During the addition the temperature in the 50 L vessel was maintained between −15 and 25° C. by means of jacket cooling. Three further portions of the compound dissolved in MIBK were added by a similar method. To the resulting slurry was added a seed of form B (0.8 g) and the mixture was then stirred at 10-20° C. overnight. In-process analysis confirmed the desired form (Form B) with no Form C or amorphous visible. The mixture was filtered and washed with acetonitrile (3340 mL). The solid was oven dried for 2 days (solid was broken up during the drying to a powder and a mixture of small lumps ~1 mm to ~3-4 mm size) until constant weight was obtained. Yield=1532.8 g (93.5%)

3-(Tetrahydro-2H-pyran-2-yloxy)propanoic acid was prepared as follows:

To a stirred solution of methanol (2.4 L) and concentrated sulfuric acid (44.4 mL, 832.61 mmol) at 0° C. under nitrogen was added, dropwise, beta-propiolactone (175 mL, 2.78 mol). This solution was allowed to stir at room temperature for 2 days. The reaction mixture was cooled to 10° C. before adding, portionwise, sodium bicarbonate (145 g, 1.72 mol), the resulting suspension was left to stir at room temperature for 75 minutes. This solution was filtered, the filter-cake was washed with methanol (800 mL). The filtrate was evaporated to an oil which was redissolved in dichloromethane (1.2 L) and stirred for 60 minutes before refiltering. This solution was filtered before evaporating to give methyl 3-hydroxypropanoate (219 g, 76%) as an oil. $^1$H NMR Spectrum: (CDCl$_3$) 2.50 (2H, t), 3.63 (3H, s), 3.78 (2H, t).

Pyridinium p-toluenesulfonate (7.65 g, 30.45 mmol) was added to a clear solution of methyl 3-hydroxypropanoate (63.4 g, 609.00 mmol) and 3,4-dihydro-2H-pyran (78 mL, 852.60 mmol) in dichloromethane (650 mL) at room temperature under nitrogen to give a cloudy solution. This was allowed to stir at room temperature overnight. The reaction mixture was washed with water (250 mL) and brine (250 mL) before drying (MgSO$_4$) and evaporating to an oil. This crude product was purified by flash silica chromatography, elution gradient 15 to 30% EtOAc in heptane. Pure fractions were evaporated to dryness to afford methyl 3-(tetrahydro-2H-pyran-2-yloxy)propanoate (67.7 g, 59.0%) as a colourless oil: $^1$H NMR Spectrum: (CDCl$_3$) 1.47 (4H, dddd), 1.55-1.84 (2H, m), 2.55 (2H, t), 3.33-3.53 (1H, m), 3.53-3.7 (4H, m), 3.78 (1H, ddd), 3.93 (1H, dt), 4.42-4.72 (1H, m); Mass Spectrum [MH]$^+$=189.

Sodium hydroxide (2M, 349 mL, 697.58 mmol) was added to a solution of methyl 3-(tetrahydro-2H-pyran-2-yloxy)propanoate (67.68 g, 359.58 mmol) in THF (680 mL) at room temperature. The reaction mixture was stirred at room temperature for 3 hours. The THF was removed in vacuo, the aqueous layer was then washed with ethyl acetate (260 mL), before cooling to 0° C. and careful acidification to pH 5 by the addition of hydrochloric acid (2M). The product was extracted with ethyl acetate (3×250 mL) before drying (MgSO$_4$) and evaporation to give 3-(tetrahydro-2H-pyran-2-yloxy)propanoic acid (57.0 g, 91%) as a clear oil. This material was dissolved in ethyl acetate (750 mL) then washed with water (3×250 mL) and brine (250 mL) to remove remaining acetic acid. The organic solution was dried (MgSO$_4$) and evaporated to give 3-(tetrahydro-2H-pyran-2-yloxy)propanoic acid (45.67 g, 72.9%) as a colourless oil: $^1$H NMR (CDCl$_3$) 1.43-1.67 (4H, m), 1.65-1.95 (2H, m), 2.68 (2H, t), 3.48-3.58 (1H, m), 3.73 (1H, dt), 3.88 (1H, ddd), 4.02 (1H, dt), 4.59-4.7 (1H, m); Mass Spectrum [M−H]$^−$=173.

The tert-butyl 4-(5-(5-amino-6-(5-tert-butyl-1,3,4-oxadiazol-2-yl)pyrazin-2-yl)-1H-1,2,4-triazol-3-yl)piperidine-1-carboxylate was prepared as follows:

Hydrazine hydrate (23.59 mL, 480.75 mmol) was added dropwise to a stirred mixture of methyl 3-amino-6-bromopyrazine-2-carboxylate (100 g, 418.04 mmol) in EtOH (2 L). The mixture was heated at 50° C. under nitrogen. The resulting thick suspension was stirred at 50° C. for 16 hours. Further hydrazine (2.5 mL) was added in one portion and the suspension was stirred at 50° C. for a further 24 hours. Ethanol (500 mL) was charged to the thick reaction mixture and the mixture was allowed to cool to room temperature. The resulting suspension was filtered and the solid washed with ethanol (1 L) and dried in vacuo to give 3-amino-6-bromopyrazine-2-carbohydrazide (98 g, quantitative) as a cream solid: $^1$H NMR Spectrum; (DMSO-$d_6$) 4.52 (2H, s), 7.59 (2H, s), 8.30 (1H, s), 9.74 (1H, s); Mass Spectrum [M+H]$^+$=232.

Pivalic anhydride (165 mL, 815.38 mmol) was added to a stirred mixture of 3-amino-6-bromopyrazine-2-carbohydrazide (172 g, 741.26 mmol) in acetonitrile (1.8 L) and the mixture was heated at 80° C. for 1 hour. The reaction was left to stir for 16 hours. The required yellow solid material was isolated by filtration. The filtrate was partitioned between EtOAc (2 L) and aqueous sodium bicarbonate (2 L). The organic layer was washed with saturated brine and dried over MgSO$_4$. The solution was filtered and concentrated to give an orange sticky solid which was triturated with MTBE (250 mL). The insoluble yellow solid was isolated by filtration and this material was shown to be identical to the first solid. The combined solids were dried in the vacuum oven at 50° C. for 3 days to afford 3-amino-6-bromo-N'-pivaloylpyrazine-2-carbohydrazide (224 g, 96%) as a yellow solid: $^1$H NMR Spectrum: (DMSO-$d_6$) 1.17 (9H, s), 7.62 (2H, s), 8.37 (1H, s), 9.42-9.56 (1H, m), 10.09-10.23 (1H, m); Mass Spectrum [M+H]$^+$=318.

To 3-amino-6-bromo-N'-pivaloylpyrazine-2-carbohydrazide (2301 g, 7.28 mol) in MeCN (10.8 L) was added DIPEA (3.044 L, 17.48 mol) and p-toluenesulfonyl chloride (1665 g, 8.73 mol) portion-wise (~280 g×6) at 50° C. over a period of 30 mins. The reaction temperature was maintained between 65-70° C. by controlling the rate of addition. After the addition was complete, the reaction mixture was stirred at 70° C. for 1 h. The mixture was cooled to room temperature and quenched with 5% NaHCO$_3$ (aqueous, 24.2 L). The resulting suspension was stirred for 30 min then filtered. The product was washed with water (14.8 L), pulled dry and dried at 50° C. for 16 h. The product was dissolved in DCM (12 L) and the phases separated. The organic phase was loaded onto a silica pad (6 kg) and the product was eluted with 20% EtOAc/DCM (8×10 L). Concentration of the product containing fractions gave 1987 g (92% yield) with a purity of 99.8% by HPLC of 5-bromo-3-(5-tert-butyl-1,3,4-oxadiazol-2-yl)pyrazin-2-amine (36 g, 17%): $^1$H NMR Spectrum: (DMSO-$d_6$) 1.43 (9H, s), 7.70 (2H, s), 8.39 (1H, s); Mass Spectrum [M+H]$^+$=298.

A stream of nitrogen gas was passed through a solution of 5-bromo-3-(5-tert-butyl-1,3,4-oxadiazol-2-yl)pyrazin-2-amine (89.35 g, 239.75 mmol) in DMA (1.2 L) for 20 minutes. Dicyclohexyl(2',4',6'-triisopropylbiphenyl-2-yl)phosphine (11.43 g, 23.98 mmol), tris(dibenzylideneacetone)dipalladium(0) (5.49 g, 5.99 mmol), zinc (1.568 g, 23.98 mmol) and dicyanozinc (16.89 g, 143.85 mmol) were added sequentially to the stirred mixture. The mixture was heated to 100° C. and stirred for 1 hour. The mixture was cooled and partitioned between DCM (3 L) and water (1 L). The black mixture was filtered through celite and the organic layer was separated. The solution was washed with water then brine. The solution was dried with magnesium sulfate and concentrated under reduced pressure. The residue was triturated with MTBE and isolated by filtration, washing with MTBE. The filter cake was dried in vacuo to afford 5-amino-6-(5-tert-butyl-1,3,4-oxadiazol-2-yl)pyrazine-2-carbonitrile (55.7 g, 95%) as a pale orange solid: $^1$H NMR Spectrum: (DMSO-$d_6$) 1.46 (9H, s), 6.02 (1H, s), 8.38 (2H, s); Mass Spectrum [M–H]$^-$=242.

Hydrazine hydrate (82 mL, 1.69 mol) was added to 5-amino-6-(5-tert-butyl-1,3,4-oxadiazol-2-yl)pyrazine-2-carbonitrile (55 g, 225.18 mmol) in IPA (200 mL) and the mixture was heated at 50° C. under nitrogen for 16 hours. The mixture was cooled in an ice bath. The resulting precipitate was collected by filtration, washed with IPA and diethyl ether and dried to a constant weight to afford (Z)-5-amino-6-(5-tert-butyl-1,3,4-oxadiazol-2-yl)pyrazine-2-carbohydrazonamide (49.2 g, 79%) as a yellow solid: $^1$H NMR Spectrum: (DMSO-$d_6$) 1.45 (9H, s), 5.26 (2H, s), 5.58 (2H, s), 7.56 (2H, s), 8.75 (1H, s); Mass Spectrum [M+H]$^+$=277.

O-(7-Azabenzotriazol-1-yl)-N,N,N',N'-tetramethyluronium hexafluorophosphate (74.3 g, 195.44 mmol) was added to a solution of N-Boc-isonipecotic acid (41.1 g, 179.15 mmol) and 4-methylmorpholine (35.9 mL, 325.74 mmol) in DMA (800 mL). The mixture was stirred for 10 minutes then (Z)-5-amino-6-(5-tert-butyl-1,3,4-oxadiazol-2-yl)pyrazine-2-carbohydrazonamide (45 g, 162.87 mmol) was added to the solution in one portion (exotherm observed from 22° C. to 27° C.). After a few minutes the product crystallised from the reaction mixture. The reaction mixture was removed from the vessel and filtered through a sinter. Additional DMA was added to wash product from the sides of the vessel (150 mL) and this was poured onto the filter cake. Isopropanol (600 mL) was added to the vessel and the remainder of the product in the vessel was suspended in this solvent using vigorous agitation. The isopropanol suspension was used to wash the filter cake once the DMA had been removed by suction. The filter cake was sucked dry then washed with MTBE and sucked dry once again. The filter cake was dried in vacuo to afford (Z)-tert-butyl 4-(2-(amino(5-amino-6-(5-tert-butyl-1,3,4-oxadiazol-2-yl)pyrazin-2-yl)methylene)hydrazinecarbonyl)piperidine-1-carboxylate (76 g, 95%) as a yellow solid: $^1$H NMR Spectrum: (DMSO-$d_6$) 1.40 (9H, s), 1.46 (9H, s), 1.63-1.9 (2H, m), 2.33-2.6 (2H, m, obscured by DMSO signal), 2.63-3.03 (2H, m), 3.18-3.48 (4H, m, obscured by water signal), 3.88-4.11 (2H, m), 6.43 (2H, s), 7.76 (2H, br), 8.84 (0.5H, s), 8.87 (0.5H, s), 9.85 (1H, s); Mass Spectrum [M+H]$^+$=488

In an alternative preparation, the N-Boc-isonipecotic acid may be made in situ as follows: Isonipecotic acid (858 g, 3.74 mol) was dissolved in DMA (25.3 L) and 4-methylmorpholine (393 mL, 3.74 mol) added. Stirred for 5 mins and isobutyl chloroformate (489 mL, 3.74 mol) added. The reaction mixture was stirred at 25° C. for 2 h and cooled to 15° C. before (Z)-5-amino-6-(5-tert-butyl-1,3,4-oxadiazol-2-yl)pyrazine-2-carbohydrazonamide (940 g, 3.4 mol) was added portionwise over 10 mins. The reaction mixture was stirred for 1-2 h at 15° C. Water (20.5 L) was added portionwise over 1 h and stirred for a further 1 h before being filtered. The filtercake was then washed with water (4×4 L) and pulled dry on the filter before being dried in a vacuum oven at 50° C. until dry to give the desired product.

Acetic acid (200 mL) was added to dioxane (500 mL) in a 3 L fixed double jacketed vessel and the solution was heated to 70° C. under nitrogen. (Z)-tert-butyl 4-(2-(amino(5-amino-6-(5-tert-butyl-1,3,4-oxadiazol-2-yl)pyrazin-2-yl)

methylene)hydrazinecarbonyl)-piperidine-1-carboxylate (74.5 g, 152.80 mmol) was added portionwise to the warm mixture. After 10 minutes the temperature was increased to 100° C. (slight reflux). The reaction mixture was stirred at 100° C. for 1.5 hours (suspension) then held at 80° C. overnight (solution formed after overnight hold). The resulting solution was concentrated under reduced pressure, then diluted with toluene, evaporated to dryness, taken up with toluene and concentrated again. The residual oil was mixed with some ethyl acetate and concentrated to dryness. A solid crystallised from solution which was triturated with MTBE (200 mL) and isolated by filtration. The filter cake was washed with water and MTBE to afford tert-butyl 4-(5-(5-amino-6-(5-tert-butyl-1,3,4-oxadiazol-2-yl)pyrazin-2-yl)-1H-1,2,4-triazol-3-yl)piperidine-1-carboxylate (50 g, 70%) as a grey solid.

The filtrate was concentrated under reduced pressure to give a yellow solid. This material was triturated with MTBE and filtered. The filter cake was washed with ethyl acetate and then MTBE to give a second crop as a pale yellow solid (4.93 g, 7%). This material was identical to the first crop: $^1$H NMR Spectrum: (DMSO-$d_6$) 1.17 (9H, s), 1.22 (9H, s), 1.29-1.47 (2H, m), 1.67-1.78 (2H, m), 2.57-2.87 (3H, m), 3.57-3.92 (2H, m), 7.56 (2H, br), 8.56 (1H, s), 13.47 (2H, br s); Mass Spectrum [M+H]+=470.

The invention claimed is:

1. A method for the treatment of a cancer selected from breast cancer and a gynecological cancer in a warm blooded animal, such as man, in need of such treatment which comprises administering to said animal an effective amount of the compound (E)-3-(3,5-Difluoro-4-((1R,3R)-2-(2-fluoro-2-methylpropyI)-3-methyl-2,3,4,9-tetrahydro-1H-pyrido[3,4-b]indol-1-yl)phenyl)acrylic acid, or a pharmaceutically acceptable salt thereof.

2. The method according to claim 1, wherein the compound is (E)-3-(3,5-Difluoro-4-((1R,3R)-2-(2-fluoro-2-methylpropyI)-3-methyl-2,3,4,9-tetrahydro-1H-pyrido [3,4-b]indol-1-yl)phenyl)acrylic acid.

3. The method according to claim 1, wherein the compound is the maleic acid salt of (E)-3-(3,5-Difluoro-4-((1R,3R)-2-(2-fluoro-2-methylpropyl)-3-methyl-2,3,4,9-tetrahydro-1H-pyrido[3,4-b]indol-1-yl)phenyl)acrylic acid.

4. The method according to claim 1, wherein the cancer is breast cancer.

5. The method according to claim 1, wherein the breast cancer is ER+ve breast cancer.

6. A method for the treatment of a cancer selected from breast cancer and a gynecological cancer in a warm-blooded animal, such as man, in need of such treatment which comprises administering to said animal an effective amount of the compound (E)-3-(3,5-Difluoro-4-((1R,3R)-2-(2-fluoro-2-methylpropyl)-3-methyl-2,3,4,9-tetrahydro-1H-pyrido[3,4-b]indol-1-yl)phenyl)acrylic acid or a pharmaceutically acceptable salt thereof, in combination with another anti-tumour agent.

7. The method according to claim 6, wherein the compound is (E)-3-(3,5-Difluoro-4-((1R,3R)-2-(2-fluoro-2-methylpropyl)-3-methyl-2,3,4,9-tetrahydro-1H-pyrido [3,4-b]indol-1-yl)phenyl)acrylic acid.

8. The method according to claim 6, wherein the compound is the maleic acid salt of (E)-3-(3,5-Difluoro-4-((1R,3R)-2-(2-fluoro-2-methylpropyl)-3-methyl-2,3,4,9-tetrahydro-1H-pyrido[3,4-b]indol-1-yl)phenyl)acrylic acid.

9. The method according to claim 6, wherein the another anti-tumour agent is palbociclib.

10. The method according to claim 6, wherein the cancer is breast cancer.

11. The method according to claim 6, wherein the breast cancer is ER+ve breast cancer.

12. The method according to claim 6, wherein the another anti-tumour agent is selected from an mTOR inhibitor or a cyclin dependent kinase inhibitor.

13. The method according to claim 6, wherein the another anti-tumour agent is AZD2014.

* * * * *